US007635563B2

(12) United States Patent
Horvitz et al.

(10) Patent No.: US 7,635,563 B2
(45) Date of Patent: Dec. 22, 2009

(54) HIGH THROUGHPUT METHODS RELATING TO MICRORNA EXPRESSION ANALYSIS

(75) Inventors: H. Robert Horvitz, Auburndale, MA (US); Eric A. Miska, Cambridge (GB); Ezequiel A. Alvarez-Saavedra, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 220 days.

(21) Appl. No.: 11/171,175

(22) Filed: Jun. 30, 2005

(65) Prior Publication Data

US 2006/0019286 A1 Jan. 26, 2006

Related U.S. Application Data

(60) Provisional application No. 60/584,381, filed on Jun. 30, 2004, provisional application No. 60/607,531, filed on Sep. 7, 2004.

(51) Int. Cl.
*C12Q 1/68* (2006.01)
*C12P 19/34* (2006.01)
(52) U.S. Cl. .......................................... 435/6; 435/91.2
(58) Field of Classification Search ........................ None
See application file for complete search history.

(56) References Cited

U.S. PATENT DOCUMENTS

| | | | |
|---|---|---|---|
| 5,736,330 | A | 4/1998 | Fulton |
| 5,802,327 | A | 9/1998 | Hawley et al. |
| 5,837,832 | A | 11/1998 | Chee et al. |
| 5,981,180 | A | 11/1999 | Chandler et al. |
| 6,046,807 | A | 4/2000 | Chandler |
| 6,057,107 | A | 5/2000 | Fulton |
| 6,139,800 | A | 10/2000 | Chandler |
| 6,268,222 | B1 | 7/2001 | Chandler et al. |
| 6,366,354 | B1 | 4/2002 | Chandler |
| 6,411,904 | B1 | 6/2002 | Chandler |
| 6,436,665 | B1 | 8/2002 | Kuimelis |
| 6,449,562 | B1 | 9/2002 | Chandler et al. |
| 6,514,295 | B1 | 2/2003 | Chandler et al. |
| 6,524,793 | B1 | 2/2003 | Chandler et al. |
| 6,528,165 | B2 | 3/2003 | Chandler |
| 6,599,331 | B2 | 7/2003 | Chandler et al. |
| 6,632,526 | B1 | 10/2003 | Chandler et al. |
| 6,649,414 | B1 | 11/2003 | Chandler et al. |
| 6,658,357 | B2 | 12/2003 | Chandler |
| 6,696,265 | B1 | 2/2004 | Spain |
| 6,696,304 | B1 | 2/2004 | Davies |
| 6,773,812 | B2 | 8/2004 | Chandler et al. |
| 6,905,766 | B2 | 6/2005 | Chandler |
| 6,916,661 | B2 | 7/2005 | Chandler et al. |
| 6,939,720 | B2 | 9/2005 | Chandler et al. |
| 2004/0152112 | A1* | 8/2004 | Croce et al. ..................... 435/6 |
| 2008/0171667 | A1* | 7/2008 | Brown et al. ................... 506/16 |

FOREIGN PATENT DOCUMENTS

WO    WO 95/25116    9/1995

OTHER PUBLICATIONS

Angevine et al., "Autoradiographic study of cell migration during histogenesis of cerebral cortex in the mouse," *Nature* 192:766-768 (1961).
Benton et al., "Screening λgt recombinant clones by hybridization to single plaques in situ," *Science* 196:180-182 (1977).
Breslauer et al., "Predicting DNA duplex stability from the base sequence," *Proc. Natl. Acad. Sci. USA* 83:3746-3750 (1986).
Chen et al., "Developmental remodeling of the retinogeniculate synapse," *Neuron* 28:955-966 (2000).
de Hoon et al., "Open source clustering software," *Bioinformatics* 20:1453-1454 (2004).
Dostie et al., "Numerous microRNPs in neuronal cells containing novel microRNAs," *RNA* 9:180-186 (2003).
Duggan et al., "Expression profiling using cDNA Microarrays," *Nat. Genet.* 21(1 Supp.):10-14 (1999).
Eisen et al., "Cluster analysis and display of genome-wide expression patterns," *Proc. Natl. Acad. Sci. USA* 95:14863-14868 (1998).
Ge, H., "UPA, a universal protein array system for quantitative detection of protein-protein, protein-DNA, protein-RNA and protein-ligand interactions," *Nucleic Acids Res.* 28:e3 (2000).
Griffiths-Jones et al., "Rfam: an RNA family database," *Nucleic Acids Res.* 31:439-441 (2003).
Grunstein et al., "Colony hybridization: a method for the isolation of cloned DNAs that contain a specific gene," *Proc. Natl. Acad. Sci. USA* 72:3961-3965 (1975).
Gupta et al., "Directly labeled mRNA produces highly precise and unbiased differential gene expression data," *Nucleic Acids Res.* 31:e13 (2003).
Heller et al., "Discovery and analysis of inflammatory disease-related genes using cDNA microarrays," *Proc. Nat. Acad. Sci. USA* 94:2150-2155 (1997).
Kim et al., "Identification of many microRNAs that copurify with polyribosomes in mammalian neurons," *Proc. Natl. Acad. Sci. USA* 101:360-365 (2004).
Kimmel, A.R., "Identification and characterization of specific clones: strategy for confirming the validity of presumptive clones," *Methods Enzymol.* 152:507-511 (1987).

(Continued)

*Primary Examiner*—James Martinell
(74) *Attorney, Agent, or Firm*—Clark & Elbing LLP; Kristina Bieker-Brady

(57) ABSTRACT

The invention relates to methods and compositions for microRNA expression analysis using microarrays.

51 Claims, 29 Drawing Sheets

OTHER PUBLICATIONS

Krichevsky et al., "A microRNA array reveals extensive regulation of microRNAs during brain development," *RNA* 9:1274-1281 (2003).

Lagos-Quintana et al., "Identification of tissue-specific microRNAs from mouse," *Curr. Biol.* 12:735-739 (2002).

Lagos-Quintana et al., "Identification of novel genes coding for small expressed RNAs," *Science* 294:853-858 (2001).

Lau et al., "An abundant class of tiny RNAs with probable regulatory roles in *Caenorhabditis elegans*," *Science* 294:858-862 (2001).

Lee et al., "An extensive class of small RNAs in *Caenorhabditis elegans*," *Science* 294:862-864 (2001).

Lewis et al., "Prediction of mammalian microRNA targets," *Cell* 115:787-798 (2003).

Lim et al., "The microRNAs of *Caenorhabditis elegans*," *Genes Dev.* 17:991-1008 (2003).

Lim et al., "Vertebrate microRNA genes," *Science* 299:1540 (2003).

Lockhart et al., "Expression monitoring by hybridization to high-density oligonucleotide arrays," *Nat. Biotechnol.* 14:1675-1680 (1996).

Lu et al, "MicroRNA expression profiles classify human cancers," *Nature* 435:834-838 (2005).

Macbeath et al., "Printing proteins as microarrays for high-throughput function determination," *Science* 289:1760-1763 (2000).

Miska et al., "Microarray analysis of microRNA expression in the developing mammalian brain," *Genome Biol.* 5:R68 (2004).

Nimmakayalu et al., "Simple method for preparation of fluor/hapten-labeled dUTP," *Biotechniques* 28:518-522 (2000).

Rakic, P., "Specification of cerebral cortical areas," *Science* 241:170-176 (1988).

Schena et al., "Quantitative monitoring of gene expression patterns with a complementary DNA microarray," *Science* 270:467-470 (1995).

Schena et al., "Parallel human genome analysis: microarray-based expression monitoring of 1000 genes," *Proc. Natl. Acad. Sci. USA* 93:10614-10619 (1996).

Sempere et al., "Expression profiling of mammalian microRNAs uncovers a subset of brain-expressed microRNAs with possible roles in murine and human neuronal differentiation," *Genome Biol.* 5:R13 (2004).

Taniguchi et al., "Quantitative assessment of DNA microarrays-comparison with northern blot analyses" *Genomics* 71:34-39 (2001).

Wahl et al., "Molecular hybridization of immobilized nucleic acids: theoretical concepts and practical Considerations," *Methods Enzymol.* 152:399-407 (1987).

Zhu et al., "Analysis of yeast protein kinases using protein chips," *Nat. Genet.* 26:283-289 (2000).

Zuker, M., "Mfold web server for nucleic acid folding and hybridization prediction," *Nucleic Acids Res.* 31:3406-3415 (2003).

\* cited by examiner mmu-let-7a-1 *Mus musculus* let-7a-1 precursor RNA

>gi|34874105|ref|NW_047490.1|Rn17_2012 *Rattus norvegicus* chromosome 17 WGS supercontig

```
Mouse:        1  ttcactgtgggatgaggtagtaggttgtatagttttagggtcacacccaccactgggaga  60
                 ||||||||||||||||||||||||||||||||||||||||||||||||||||||||||||
Rat:    3523419  ttcactgtgggatgaggtagtaggttgtatagttttagggtcacacccaccactgggaga  3523478

Mouse:       61  taactatacaatctactgtctttcctaaggtgat  94
                 ||||||||||||||||||||||||||||||||||
Rat:    3523479  taactatacaatctactgtctttcctaaggtgat  3523512
``` mmu-let-7a-2 *Mus musculus* let-7a-2 precursor RNA

>gi|34865068|ref|NW_047799.1|Rn8_2323 *Rattus norvegicus* chromosome 8 WGS supercontig

```
Mouse:        3  gcatgttcccaggttgaggtagtaggttgtatagtttagagttacatcaagggagataac  62
                 ||||| ||||||| ||||||||||||||||||||||||||||||||  ||||||||||||
Rat:   14144995  gcatgctcccaggctgaggtagtaggttgtatagtttagagttacaacaagggagataac  14145054

Mouse:       63  tgtacagcctcctagctttccttgggacttgcac  96
                 ||||||||||||||||||||||||||||||||||
Rat:   14145055  tgtacagcctcctagctttccttgggacttgcac  14145088
``` mmu-let-7b *Mus musculus* let-7b precursor RNA

>gi|34934010|ref|NW_047783.1|Rn7_2307 *Rattus norvegicus* chromosome 7 WGS supercontig

```
Mouse:        4  gggtgaggtagtaggttgtgtggtttcagggcagtgatgttgcccctccgaagataacta  63
                 |||||||||||||||||||||||||||||||||||||||| |||||||||||||||||||
Rat:    1610759  gggtgaggtagtaggttgtgtggtttcagggcagtgatgtcgcccctccgaagataacta  1610818

Mouse:       64  tacaacctactgccttccctga  85
                 ||||||||||||||||||||||
Rat:    1610819  tacaacctactgccttccctga  1610840
``` mmu-let-7c-1 *Mus musculus* let-7c-1 precursor RNA

>gi|34933964|ref|NW_047354.1|Rn11_1874 *Rattus norvegicus* chromosome 11 WGS supercontig

```
Mouse:        1  tgtgtgcatccgggttgaggtagtaggttgtatggtttagagttacaccctgggagttaa  60
                 ||||||||||||||||||||||||||||||||||||||||||||||||||||||||||||
Rat:   16398264  tgtgtgcatccgggttgaggtagtaggttgtatggtttagagttacaccctgggagttaa  16398323

Mouse:       61  ctgtacaaccttctagctttccttggagcacact  94
                 ||||||||||||||||||||||||||||||||||
Rat:   16398324  ctgtacaaccttctagctttccttggagcacact  16398357
``` mmu-let-7c-2 *Mus musculus* let-7c-2 precursor RNA

>gi|34934010|ref|NW_047783.1|Rn7_2307 *Rattus norvegicus* chromosome 7 WGS supercontig

```
Mouse:        1  acggcctttgggtgaggtagtaggttgtatggttttggctctgccccgctctgcggta  60
                 ||||||||||||||||||||||||||||||||||||||||||||||||||||||||||
Rat:    1610341  acggcctttgggtgaggtagtaggttgtatggttttggctctgccccgctctgcggta  1610400

Mouse:       61  actatacaatctactgtctttcctgaagtggccgc  95
                 |||||||||||||||||||||||||||||||||||
Rat:    1610401  actatacaatctactgtctttcctgaagtggccgc  1610435
``` mmu-let-7e *Mus musculus* let-7e precursor RNA

>gi|34854887|ref|NW_047555.1|Rn1_2077 *Rattus norvegicus* chromosome 1 WGS supercontig

```
Mouse:        1  cgcgccccccgggctgaggtaggaggttgtatagttgaggaagacacccgaggagatcac  60
                 ||||||||||||||||||||||||||||||||||||||||||||||||||||||||||||
Rat:    1805450  cgcgccccccgggctgaggtaggaggttgtatagttgaggaagacacccgaggagatcac  1805509

Mouse:       61  tatacggcctcctagctttccccaggctgcgcc  93
                 |||||||||||||||||||||||||||||||||
```

Figure 1A

Rat:      1805510 tatacggcctcctagctttccccaggctgcgcc 1805542 hsa-let-7i Homo sapiens let-7i precursor RNA

>gi|34865737|ref|NW_047776.1|Rn7_2300 *Rattus norvegicus* chromosome 7 WGS
           supercontig Mouse:   1        ctggctgaggtagtagtttgtgctgttggtcgggttgtgacattgcccgctgtggagata 60
                  ||||||||||||||||||||||||||||||||||||||||||||||||||||||||||||
Rat:     3609065  ctggctgaggtagtagtttgtgctgttggtcgggttgtgacattgcccgctgtggagata 3609006

Mouse:   61       actgcgcaagctactgccttgcta 84
                  ||||||||||||||||||||||||
Rat:     3609005  actgcgcaagctactgccttgcta 3608982 mmu-mir-7-1 Mus musculus miR-7-1 precursor RNA

>gi|34873863|ref|NW_047487.1|Rn17_2009 *Rattus norvegicus* chromosome 17 WGS
           supercontig Mouse:   1        ttggatgttggcctagttctgtgtggaagactagtgattttgttgttttagataactaa 60
                  ||||||||||||||||||||||||||||||||||||||||||||||||||||||||||||
Rat:     6715460  ttggatgttggcctagttctgtgtggaagactagtgattttgttgttttagataactaa 6715519

Mouse:   61       aacgacaacaaatcacagtctgccatatggcacaggccacctctacag 108
                  |||||||||||||||||||||||||||||||||||||||||||||||
Rat:     6715520  gacgacaacaaatcacagtctgccatatggcacaggccacctctacag 6715567 mmu-mir-7-2 Mus musculus miR-7-2 precursor RNA

>gi|34857743|ref|NW_047560.1|Rn1_2082 *Rattus norvegicus* chromosome 1 WGS
           supercontig Mouse:   8        ccagccccgtttggaagactagtgattttgttgttgtgtctctgtatccaacaacaagtc 67
                  ||||||| ||  |||||||||||||||||||||||||||||||  |||   |||||||||||||
Rat:     14956730 ccagccctgtctggaagactagtgattttgttgttgtgtctgtgt--ccaacaacaagtc 14956787

Mouse:   68       ccagtctgccacatggtgctggtca 92
                  ||||||||||||||||||| ||||||
Rat:     14956788 ccagtctgccacatggtgttggtca 14956810 mmu-mir-9-1 Mus musculus miR-9-1 precursor RNA

>gi|34858271|ref|NW_047626.1|Rn2_2148 *Rattus norvegicus* chromosome 2 WGS
           supercontig Mouse:   1        cggggttggttgttatctttggttatctagctgtatgagtggtgtggagtcttcataaag 60
                  ||||||||||||||||||||||||||||||||||||||||||||||||||||||||||||
Rat:     6714042  cggggttggttgttatctttggttatctagctgtatgagtggtgtggagtcttcataaag 6714101

Mouse:   61       ctagataaccgaaagtaaaaataaccccca 89
                  ||||||||||||||||||||||||||||||
Rat:     6714102  ctagataaccgaaagtaaaaataaccccca 6714130 mmu-mir-9-3 Mus musculus miR-9-3 precursor RNA

>gi|34857743|ref|NW_047560.1|Rn1_2082 *Rattus norvegicus* chromosome 1 WGS
           supercontig Mouse:   1        ggaggcccgtttctctctttggttatctagctgtatgagtgccacagagccgtcataaag 60
                  ||||||||||||||||||||||||||||||||||||||||||||||||||||||||||||
Rat:     15603655 ggaggcccgtttctctctttggttatctagctgtatgagtgccacagagccgtcataaag 15603714

Mouse:   61       ctagataaccgaaagtagaaatgactct 88
                  ||||||||||||||||||||||||||||
Rat:     15603715 ctagataaccgaaagtagaaatgactct 15603742

Figure 1A mmu-mir-9-2 Mus musculus miR-9-2 precursor RNA

>gi|34853324|ref|NW_047616.1|Rn2_2138 *Rattus norvegicus* chromosome 2 WGS
           supercontig Mouse:   1        gttgttatctttggttatctagctgtatgagtgtattggtcttcataaagctagataacc 60
                  ||||||||||||||||||||||||||||||||||||||||||||||||||||||||||||
Rat:     6903262  gttgttatctttggttatctagctgtatgagtgtattggtcttcataaagctagataacc 6903203

```
Mouse: 61        gaaagtaaaaac 72
                 ||||||||||||
Rat:   6903202   gaaagtaaaaac 6903191
``` mmu-mir-16-2 *Mus musculus* miR-16-2 precursor RNA

>gi|34857808|ref|NW_047625.1|Rn2_2147 *Rattus norvegicus* chromosome 2 WGS supercontig

```
Mouse: 5         cttgttccactctagcagcacgtaaatattggcgtagtgaaataaatattaaacaccaat 64
                 ||||||||  |||||||||||||||||||||||||||||||||||||||||||||||||
Rat:   45354558  cttgttccgctctagcagcacgtaaatattggcgtagtgaaataaatattaaacaccaat 45354617

Mouse: 65        attattgtgctgctttagtgtgacagggata 95
                 |||||||||||||||||||||||||||||||
Rat:   45354618  attattgtgctgctttagtgtgacagggata 45354648
``` mmu-mir-24-1 *Mus musculus* miR-24-1 precursor RNA

>gi|34873863|ref|NW_047487.1|Rn17_2009 *Rattus norvegicus* chromosome 17 WGS supercontig

```
Mouse: 1         ctccggtgcctactgagctgatatcagttctcatttcacacactggctcagttcagcagg 60
                 ||||||||||||||||||||||||||||||||||||||||||||||||||||||||||||
Rat:   1862421   ctccggtgcctactgagctgatatcagttctcatttcacacactggctcagttcagcagg 1862362

Mouse: 61        aacaggag 68
                 ||||||||
Rat:   1862361   aacaggag 1862354
``` mmu-mir-24-2 *Mus musculus* miR-24-2 precursor RNA

>gi|34851559|ref|NW_047534.1|Rn19_2056 *Rattus norvegicus* chromosome 19 WGS supercontig

```
Mouse: 1         gcctctctccgggctccgcctccgtgcctactgagctgaaacagttgattccagtgcac 60
                 |||||||  ||||||||||||| |||||||||||||||||||||||||||||||||||||
Rat:   10919959  gcctctccctgggctccgcctcctgtgcctactgagctgaaacagttgattccagtgcac 10919900

Mouse: 61        tggctcagttcagcaggaacaggagtccagccccc-taggagctggca 107
                 |||||||||||||||||||||||||||||||||||  ||||||||||
Rat:   10919899  tggctcagttcagcaggaacaggagtccagcccccataggagctggca 10919852
``` mmu-mir-26b *Mus musculus* miR-26b precursor RNA

>gi|34877332|ref|NW_047816.1|Rn9_2340 *Rattus norvegicus* chromosome 9 WGS supercontig

```
Mouse: 1         tgcccgggacccagttcaagtaattcaggataggttgtggtgctgaccagcctgttctcc 60
                 |||||||||||||||||||||||||||||||||||||||||||| |||||||||||||||
Rat:   17163277  tgcccgggacccagttcaagtaattcaggataggttgtggtgctggccagcctgttctcc 17163336

Mouse: 61        attacttggctcgggggccggtgcc 85
                 |||||||||||||||||||||||||
Rat:   17163337  attacttggctcgggggccggtgcc 17163361
``` mmu-mir-28 *Mus musculus* miR-28 precursor RNA

>gi|34869631|ref|NW_047356.1|Rn11_1876 *Rattus norvegicus* chromosome 11 WGS supercontig

```
Mouse: 1         ggtccctaccttcaaggagctcacagtctattgagttgcctttctgattctcccactaga 60
                 |||||||||  |||||||||||||||||||||||||| ||||||||||||||||||||||
Rat:   31535044  ggtccctacccgcaaggagctcacagtctattgagttccttttctgattctcccactaga 31534985

Mouse: 61        ttgtgagctgctggagggcaggcact 86
                 |||||||||  |||||||||||||||
Rat:   31534984  ttgtgagctcctggagggcaggcact 31534959
```

Figure 1A mmu-mir-29a *Mus musculus* miR-29a precursor RNA

>gi|34855362|ref|NW_047689.1|Rn4_2212 *Rattus norvegicus* chromosome 4 WGS supercontig

```
Mouse: 1         accccttagaggatgactgatttcttttggtgttcagagtcaatagaattttctagcacc 60
```

```
Rat:   28825083 acccttagaggatgactgatttcttttggtgttcagagtcaatagaattttctagcacc 28825024

Mouse:    61    atctgaaatcggttataatgattgggga 88
Rat:   28825023 atctgaaatcggttataatgattgggga 28824996
```

**mmu-mir-29c *Mus musculus* miR-29c precursor RNA**

>gi|34881453|ref|NW_047404.1|Rn13_1926 *Rattus norvegicus* chromosome 13 WGS supercontig

```
Mouse:     1    atctcttacacaggctgaccgatttctcctggtgttcagagtctgttttgtctagcacc 60
Rat:   2146548 atctcttacacaggctgaccgatttctcctggtgttcagagtctgttttgtctagcacc 2146607

Mouse:    61    atttgaaatcggttatgatgtaggggga 88
Rat:   2146608 atttgaaatcggttatgatgtaggggga 2146635
```

**mmu-mir-29b-1 *Mus musculus* miR-29b-1 precursor RNA**

>gi|34855362|ref|NW_047689.1|Rn4_2212 *Rattus norvegicus* chromosome 4 WGS supercontig

```
Mouse:     1    aggaagctggtttcatatggtggtttagatttaaatagtgattgtctagcaccatttgaa 60
Rat:   28825451 aggaagctggtttcatatggtggtttagatttaaatagtgattgtctagcaccatttgaa 28825392

Mouse:    61    atcagtgttct 71
Rat:   28825391 atcagtgttct 28825381
```

**mmu-mir-29b-2 *Mus musculus* miR-29b-2 precursor RNA**

>gi|34881453|ref|NW_047404.1|Rn13_1926 *Rattus norvegicus* chromosome 13 WGS supercontig

```
Mouse:     1    cttctggaagctggtttcacatggtggcttagattttccatctttgtatctagcaccat 60
Rat:   2146020 cttctggaagctggtttcacatggtggcttagattttccatctttgtatctagcaccat 2146079

Mouse:    61    ttgaaatcagtgttttaggag 81
Rat:   2146080 ttgaaatcagtgttttaggag 2146100
```

**mmu-mir-30b *Mus musculus* miR-30b precursor RNA**

>gi|34867094|ref|NW_047780.1|Rn7_2304 *Rattus norvegicus* chromosome 7 WGS supercontig

```
Mouse:     1    atgtaaacatcctacactcagctgtcatacatgcgttggctgggatgtggatgtttacgt 60
Rat:    418464 atgtaaacatcctacactcagctgtcatacatgagttggctgggatgtggatgtttacgt 418405
```

**mmu-mir-30c-1 *Mus musculus* miR-30c-1 precursor RNA**

>gi|34871316|ref|NW_047719.1|Rn5_2243 *Rattus norvegicus* chromosome 5 WGS supercontig

```
Mouse:     1    accatgttgtagtgtgtgtaaacatcctacactctcagctgtgagctcaaggtggctggg 60
Rat:   2519905 accatgttgtagtgtgtgtaaacatcctacactctcagctgtgagctcaaggtggctggg 2519846

Mouse:    61    agagggttgtttactccttctgccatgga 89
Rat:   2519845 agagggttgtttactccttctgccatgga 2519817
```

Figure 1A

**mmu-mir-30c-2 *Mus musculus* miR-30c-2 precursor RNA**

>gi|34875263|ref|NW_047813.1|Rn9_2337 *Rattus norvegicus* chromosome 9 WGS supercontig

```
Mouse:     1    gagtgacagatattgtaaacatcctacactctcagctgtgaaaagtaagaaagctgggag 60
```

Rat:     22164044 gagtgacagatactgtaaacatcctacactctcagctgtgaaaagtaagaaagctgggag 22164103

Mouse:   61       aaggctgtttactctctctgcctt 84
                  ||||||||||||||||||||||||
Rat:     22164104 aaggctgtttactctctctgcctt 22164127 mmu-mir-92-2 *Mus musculus* miR-92-2 precursor RNA

>gi|34881658|ref|NW_048049.1|RnX_2574 *Rattus norvegicus* chromosome X WGS
             supercontig Mouse:   1       tgcccattcatccacaggtggggattggtggcattacttgtgttagatataaagtattgc 60
                 |||||||||||||||||||||||||||| ||| ||||||||||||||||||| |||||||
Rat:     2017453 tgcccattcatccacaggtggggattagtgccattacttgtgttagataaaaagtattgc 2017394

Mouse:   61      acttgtcccggcctgaggaagaaa 84
                 ||||||||||||||||||||||||
Rat:     2017393 acttgtcccggcctgaggaagaaa 2017370 mmu-mir-93 *Mus musculus* miR-93 precursor RNA

>gi|34871632|ref|NW_047369.1|Rn12_1890 *Rattus norvegicus* chromosome 12 WGS
             supercontig Mouse:   1       agtcatgggggctccaaagtgctgttcgtgcaggtagtgtaattacctgacctactgctg 60
                 ||||||||||||||||||||||||||||||||||||||||| | || ||||||||||||
Rat:     5549656 agtcatgggggctccaaagtgctgttcgtgcaggtagtgca-ttgcctgacctactgctg 5549598

Mouse:   61      agctagcacttcccgagcccccaggaca 88
                 ||||||||||||||||||||||||||||
Rat:     5549597 agctagcacttcccgagcccccaggaca 5549570 mmu-mir-99a *Mus musculus* miR-99a precursor RNA

>gi|34933964|ref|NW_047354.1|Rn11_1874 *Rattus norvegicus* chromosome 11 WGS
             supercontig Mouse:   1        cataaacccgtagatccgatcttgtggtgaagtggaccgcgcaagctcgtttctatgggt 60
                  |||||||||||||||||||||||||||||||||||||||| |||||||||||||||||||
Rat:     16397552 cataaacccgtagatccgatcttgtggtgaagtggaccgcacaagctcgtttctatgggt 16397611

Mouse:   61       ctgtg 65
                  |||||
Rat:     16397612 ctgtg 16397616 mmu-mir-99b *Mus musculus* miR-99b precursor RNA

>gi|34854887|ref|NW_047555.1|Rn1_2077 *Rattus norvegicus* chromosome 1 WGS
             supercontig Mouse:   1       ggcacccacccgtagaaccgaccttgcggggccttcgccgcacacaagctcgtgtctgtg 60
                 ||||||||||||||||||||||||||||||||||||||||||||||||||||||||||||
Rat:     1805285 ggcacccacccgtagaaccgaccttgcggggccttcgccgcacacaagctcgtgtctgtg 1805344

Mouse:   61      ggtccgtgtc 70
                 ||||||||||
Rat:     1805345 ggtccgtgtc 1805354 mmu-mir-103-1 *Mus musculus* miR-103-1 precursor RNA

>gi|34872015|ref|NW_047334.1|Rn10_1854 *Rattus norvegicus* chromosome 10 WGS
             supercontig Mouse:   1       ttcttactgccctcggcttctttacagtgctgccttgttgcatatggatcaagcagcatt 60
                 ||||||||||||||||||||||||||||||||||||||||||||||||||||||||||||
Rat:     7519813 ttcttactgccctcggcttctttacagtgctgccttgttgcatatggatcaagcagcatt 7519872

Mouse:   61      gtacagggctatgaaggcattgagac 86
                 ||||||||||||||||||||||||||
Rat:     7519873 gtacagggctatgaaggcattgagac 7519898

Figure 1A mmu-mir-103-2 *Mus musculus* miR-103-2 precursor RNA

>gi|34859757|ref|NW_047658.1|Rn3_2180 *Rattus norvegicus* chromosome 3 WGS
             supercontig

```
Mouse:  1        gtcttcgtgctttcagcttctttacagtgctgccttgtagcattcaggtcaagcagcatt  60
                 ||||||||||||||||||||||||||||||||||||||||||||||||||||||||||||
Rat:    9173953  gtcttcgtgctttcagcttctttacagtgctgccttgtagcattcaggtcaagcagcatt  9174012

Mouse:  61       gtacagggctatgaaagaaccaagaa  86
                 ||||||||||||||||||||||||||
Rat:    9174013  gtacagggctatgaaagaaccaagaa  9174038
``` mmu-mir-124a-1 *Mus musculus* miR-124a-1 precursor RNA

>gi|34875912|ref|NW_047454.1|Rn15_1976 *Rattus norvegicus* chromosome 15 WGS
            supercontig

```
Mouse:  1         aggcctctctctccgtgttcacagcggaccttgatttaaatgtccatacaattaaggcac  60
                  ||||||||||||||||||||||||||||||||||||||||||||||||||||||||||||
Rat:    15806503  aggcctctctctccgtgttcacagcggaccttgatttaaatgtccatacaattaaggcac  15806562

Mouse:  61        gcggtgaatgccaagaatgggctg  85
                  ||||||||||||||||||||||||
Rat:    15806563  gcggtgaatgccaagaatgggctg  15806587
``` mmu-mir-124a-2 *Mus musculus* miR-124a-2 precursor RNA

>gi|34855621|ref|NW_047624.1|Rn2_2146 *Rattus norvegicus* chromosome 2 WGS
            supercontig

```
Mouse:  1        atcaagatcagagactctgctctccgtgttcacagcggaccttgatttaatgtcatacaa  60
                 ||||||||||||||||||||||||||||||||||||||||||||||||||||||||||||
Rat:    7685115  atcaagatcagagactctgctctccgtgttcacagcggaccttgatttaatgtcatacaa  7685174

Mouse:  61       ttaaggcacgcggtgaatgccaagagcggagcctacggctgcacttgaa  109
                 |||||||||||||||||||||||||||||||||||||||||||||||||
Rat:    7685175  ttaaggcacgcggtgaatgccaagagcggagcctacggctgcacttgaa  7685223
``` mmu-mir-124a-3 *Mus musculus* miR-124a-3 precursor RNA

>gi|34861141|ref|NW_047667.1|Rn3_2189 *Rattus norvegicus* chromosome 3 WGS
            supercontig

```
Mouse:  1       ctctgcgtgttcacagcggaccttgatttaatgtctatacaattaaggcacgcggtgaat  60
                ||||||||||||||||||||||||||||||||||||||||||||||||||||||||||||
Rat:    505484  ctctgcgtgttcacagcggaccttgatttaatgtctatacaattaaggcacgcggtgaat  505543

Mouse:  61      gccaagag  68
                ||||||||
Rat:    505544  gccaagag  505551
``` mmu-mir-125a *Mus musculus* miR-125a precursor RNA

>gi|34854887|ref|NW_047555.1|Rn1_2077 *Rattus norvegicus* chromosome 1 WGS
            supercontig

```
Mouse:  1        ctgggtccctgagacccttttaacctgtgaggacgtccagggtcacaggtgaggttcttgg  60
                 ||||||||||||||||||||||||||||||||||||||||||||||||||||||||||||
Rat:    1805905  ctgggtccctgagacccttttaacctgtgaggacgtccagggtcacaggtgaggttcttgg  1805964

Mouse:  61       gagcctgg  68
                 ||||||||
Rat:    1805965  gagcctgg  1805972
``` mmu-mir-125b-2 *Mus musculus* miR-125b-2 precursor RNA

>gi|34933964|ref|NW_047354.1|Rn11_1874 *Rattus norvegicus* chromosome 11 WGS
            supercontig

```
Mouse:  2         cctagtccctgagaccctaacttgtgaggtatttagtaacatcacaagtcaggttcttg  61
                  |||||||||||||||||||||||||||||||||||||||||||||||||||| |||||
Rat:    16443677  cctagtccctgagaccctaacttgtgaggtatttagtaacatcacaagtcaggctcttg  16443736

Mouse:  62        ggacctaggc  71
                  ||||||||||
Rat:    16443737  ggacctaggc  16443746
``` mmu-mir-125b-1 *Mus musculus* miR-125b-1 precursor RNA

Figure 1A

```
Mouse:  1          tgcgctcccctcagtccctgagaccctaacttgtgatgtttaccgtttaaatccacggt 60
                   |||||||||||||||||||||||||||||||||||||||||||||||||||||||||||
Rat:    14189379   tgcgctcccctcagtccctgagaccctaacttgtgatgtttaccgtttaaatccacggt 14189438

Mouse:  61         taggctcttgggagctg 77
                   |||||||||||||||||
Rat:    14189439   taggctcttgggagctg 14189455
``` mmu-mir-127 *Mus musculus* miR-127 precursor RNA

>gi|34935858|ref|NW_047762.1|Rn6_2286 *Rattus norvegicus* chromosome 6 WGS
           supercontig

```
Mouse:  1          ccagcctgctgaagctcagagggctctgattcagaaagatcatcggatccgtctgagctt 60
                   ||||||||||||||||||||||||||||||||||||||||||||||||||||||||||||
Rat:    29527445   ccagcctgctgaagctcagagggctctgattcagaaagatcatcggatccgtctgagctt 29527504

Mouse:  61         ggctggtcgg 70
                   ||||||||||
Rat:    29527505   ggctggtcgg 29527514
``` mmu-mir-128a *Mus musculus* miR-128a precursor RNA

>gi|34933508|ref|NW_047394.1|Rn13_1916 *Rattus norvegicus* chromosome 13 WGS
           supercontig

```
Mouse:  1          gttggattcggggccgtagcactgtctgagaggtttacatttctcacagtgaaccggtct 60
                   ||||||||||||||||||||||||||||||||||||||||||||||||||||||||||||
Rat:    1019804    gttggattcggggccgtagcactgtctgagaggtttacatttctcacagtgaaccggtct 1019863

Mouse:  61         cttttcagc 70
                   ||||||||||
Rat:    1019864    cttttcagc 1019873
``` mmu-mir-128b *Mus musculus* miR-128b precursor RNA

>gi|34866469|ref|NW_047802.1|Rn8_2326 *Rattus norvegicus* chromosome 8 WGS
           supercontig

```
Mouse:  1          cagtgggaaggggggccgatgcactgtaagagagtgagtagcaggtctcacagtgaaccg 60
                   ||||||||||||||||||||||||||||||||||||||||||||||||||||||||||||
Rat:    3171003    cagtgggaaggggggccgatgcactgtaagagagtgagtagcaggtctcacagtgaaccg 3170944

Mouse:  61         gtctctttccctactg 76
                   ||||||||||||||||
Rat:    3170943    gtctctttccctactg 3170928
``` mmu-mir-130a *Mus musculus* miR-130a precursor RNA

>gi|34857850|ref|NW_047657.1|Rn3_2179 *Rattus norvegicus* chromosome 3 WGS
           supercontig

```
Mouse:  1          gagctcttttcacattgtgctactgtcta-acgtgtaccgagcagtgcaatgttaaaagg 59
                   |||||||||||||||||||||||||||||| |||||||||||||||||||||||||||||
Rat:    9350850    gagctcttttcacattgtgctactgtctacacgtgtaccgagcagtgcaatgttaaaagg 9350791

Mouse:  60         gcatc 64
                   |||||
Rat:    9350790    gcatc 9350786
``` mmu-mir-132 *Mus musculus* miR-132 precursor RNA

>gi|34873416|ref|NW_047336.1|Rn10_1856 *Rattus norvegicus* chromosome 10 WGS
           supercontig

```
Mouse:  1          gggcaaccgtggctttcgattgttactgtgggaaccggaggtaacagtctacagccatgg 60
                   ||||||||||||||||||||||||||||||||||||||||||||||||||||||||||||
Rat:    3479949    gggcaaccgtggctttcgattgttactgtgggaaccggaggtaacagtctacagccatgg 3480008

Mouse:  61         tcgccc 66
                   ||||||
Rat:    3480009    tcgccc 3480014
```

Figure 1A mmu-mir-136 *Mus musculus* miR-136 precursor RNA

>gi|34935858|ref|NW_047762.1|Rn6_2286 Rattus norvegicus chromosome 6 WGS
          supercontig

```
Mouse:      1    gaggactccatttgttttgatgatggattcttaagctccatcatcgtctcaaatgagtct   60
                 ||||||||||||||||||||||||||||||||||||||||||||||||||||||||||||
Rat:    29530106 gaggactccatttgttttgatgatggattcttaagctccatcatcgtctcaaatgagtct   29530165

Mouse:     61    tc   62
                 ||
Rat:    29530166 tc   29530167
``` mmu-mir-138-1 *Mus musculus* miR-138-1 precursor RNA

>gi|34866724|ref|NW_047804.1|Rn8_2328 Rattus norvegicus chromosome 8 WGS
          supercontig

```
Mouse:      1    ctctagcatggtgttgtgggacagctggtgttgtgaatcaggccgttgccaatcagagaa   60
                 |||| |||||||||||||||||||||||||||||||||||||||||||||||||||||||
Rat:     156597 ctctggcatggtgttgtgggacagctggtgttgtgaatcaggccgttgccaatcagagaa   156656

Mouse:     61    cggctacttcacaacaccaggccacactgcactgca   97
                 |||||||||||||||||||||| | |||||||||||
Rat:     156657 cggctacttcacaacaccagggtctcactgcactgca   156693
``` mmu-mir-138-2 *Mus musculus* miR-138-2 precursor RNA

>gi|34851309|ref|NW_047531.1|Rn19_2053 Rattus norvegicus chromosome 19 WGS
          supercontig

```
Mouse:      1    cagctggtgttgtgaatcaggccgacgagcagcgcatcctcttacccggctatttcacga   60
                 |||||||||||||||||||||||||||||||||| |||||||||||||||||||||||||
Rat:    11119560 cagctggtgttgtgaatcaggccgacgagcaacgcatcctcttacccggctatttcacga   11119501

Mouse:     61    caccagggttg   71
                 |||||||||||
Rat:    11119500 caccagggttg   11119490
``` mmu-mir-139 *Mus musculus* miR-139 precursor RNA

>gi|34860310|ref|NW_047562.1|Rn1_2084 Rattus norvegicus chromosome 1 WGS
          supercontig

```
Mouse:      1    gtgtattctacagtgcacgtgtctccagtgtggctcggaggctggagacgcggccctgtt   60
                 ||||||||||||||||||||||||||||||||||||||||||||||||||||||||||||
Rat:     1586714 gtgtattctacagtgcacgtgtctccagtgtggctcggaggctggagacgcggccctgtt   1586773

Mouse:     61    ggagtaac   68
                 ||||||||
Rat:     1586774 ggagtaac   1586781
``` mmu-mir-142 *Mus musculus* miR-142 precursor RNA

>gi|34873416|ref|NW_047336.1|Rn10_1856 Rattus norvegicus chromosome 10 WGS
          supercontig

```
Mouse:      1    acccataaagtagaaagcactactaacagcactggagggtgtagtgtttcctactttatg   60
                 ||||||||||||||||||||||||||||||||||||||||||||||||||||||||||||
Rat:    17049244 acccataaagtagaaagcactactaacagcactggagggtgtagtgtttcctactttatg   17049303

Mouse:     61    gatg   64
                 ||||
Rat:    17049304 gatg   17049307
``` mmu-mir-145 *Mus musculus* miR-145 precursor RNA

>gi|34932227|ref|NW_047514.1|Rn18_2036 Rattus norvegicus chromosome 18 WGS
          supercontig

```
Mouse:      1    ctcacggtccagttttcccaggaatcccttggatgctaagatggggattcctggaaatac   60
                 ||||||||||||||||||||||||||||||||||||||||||||||||||||||||||||
Rat:     3665639 ctcacggtccagttttcccaggaatcccttggatgctaagatggggattcctggaaatac   3665580

Mouse:     61    tgttcttgag   70
                 ||||||||||
Rat:     3665579 tgttcttgag   3665570
```

Figure 1A mmu-mir-146 *Mus musculus* miR-146 precursor RNA

\>gi|34872015|ref|NW_047334.1|Rn10_1854 *Rattus norvegicus* chromosome 10 WGS supercontig

```
Mouse:  1         agctctgagaactgaattccatgggttatatcaatgtcagacctgtgaaattcagttctt  60
                  ||||||||||||||||||||||||||||||||| ||||||||||||||| |||||||||||
Rat:    15301237  agctctgagaactgaattccatgggttatagcaatgtcagacctgtgaagttcagttctt  15301178

Mouse:  61        cagct  65
                  ||||
Rat:    15301177  tagct  15301173
``` mmu-mir-150 *Mus musculus* miR-150 precursor RNA

```
Mouse:  1         ccctgtctcccaacccttgtaccagtgctgtgcctcagaccctggtacaggcctggggga  60
                  ||||||||||||||||||||||||||||||||||||||||||||||||||||||||||||
Rat:    4552248   ccctgtctcccaacccttgtaccagtgctgtgcctcagaccctggtacaggcctggggga  4552307

Mouse:  61        taggg  65
                  ||||
Rat:    4552308   caggg  4552312
``` mmu-mir-154 *Mus musculus* miR-154 precursor RNA

```
Mouse:  1         gaagataggttatccgtgttgccttcgctttattcgtgacgaatcatacacggttgacct  60
                  ||||||||||||||||||||||||||||||||||||||||||||||||||||||||||||
Rat:    29762799  gaagataggttatccgtgttgccttcgctttattcgtgacgaatcatacacggttgacct  29762858

Mouse:  61        attttt  66
                  ||||||
Rat:    29762859  attttt  29762864
``` mmu-mir-185 *Mus musculus* miR-185 precursor RNA

\>gi|34869997|ref|NW_047358.1|Rn11_1878 *Rattus norvegicus* chromosome 11 WGS supercontig

```
Mouse:  1         agggattggagagaaaggcagttcctgatggtcccctcccagggggctggctttcctctgg  60
                  ||||||||||||||||||||||||||||||||||||||||||||||||||||||||||||
Rat:    2687772   agggattggagagaaaggcagttcctgatggtcccctcccagggggctggctttcctctgg  2687831

Mouse:  61        tcctt  65
                  |||||
Rat:    2687832   tcctt  2687836
``` mmu-mir-191 *Mus musculus* miR-191 precursor RNA

\>gi|34866469|ref|NW_047802.1|Rn8_2326 *Rattus norvegicus* chromosome 8 WGS supercontig

```
Mouse:  1         agcgggcaacggaatcccaaaagcagctgttgtctccagagcattccagctgcacttgga  60
                  ||||||||||||||||||||||||||||||||||||||||||||||||||||||||||||
Rat:    58055     agcgggcaacggaatcccaaaagcagctgttgtctccagagcattccagctgcacttgga  58114

Mouse:  61        tttcgttccctgct  74
                  ||||||||||||||
Rat:    58115     tttcgttccctgct  58128
``` mmu-mir-213 *Mus musculus* miR-213 precursor RNA

\>gi|34880444|ref|NW_047396.1|Rn13_1918 *Rattus norvegicus* chromosome 13 WGS supercontig

```
Mouse:  1         ggttgcttcagtgaacattcaacgctgtcggtgagtttggaattcaaataaaaaccatcg  60
                  ||||||||||||||||||||||||||||||||||||||||||||||||||||||||||||
Rat:    1976067   ggttgcttcagtgaacattcaacgctgtcggtgagtttggaattcaaataaaaaccatcg  1976126

Mouse:  61        accgttgattgtaccctatagctaacc  87
                  |||||||||||||||||||||||||||
Rat:    1976127   accgttgattgtaccctatagctaacc  1976153
``` mmu-mir-300 *Mus musculus* miR-300 precursor RNA

Figure 1A

```
>gi|34935858|ref|NW_047762.1|Rn6_2286 Rattus norvegicus chromosome 6 WGS
                supercontig Mouse: 1         gctacttgaagagaggttatcctttgtgtgtttgctttacgcgaaatgaatatgcaaggg 60
                 ||||||||||||||||||||||||||||||||||||||||||||||||||||||||||||
Rat:   29748356  gctacttgaagagaggttatcctttgtgtgtttgctttacgcgaaatgaatatgcaaggg 29748415

Mouse: 61        caagctctcttcgaggagc 79
                 |||||||||||||||||||
Rat:   29748416  caagctctcttcgaggagc 29748434
```

Figure 1A

| Rat microRNA | Predicted folding Energy(kcal/mole) | Predicted stem loop precursor |
|---|---|---|
| rno-let-7a-2 | dG = -38.9 | ```
       10         20        30        40
  --|  UGC       CU    G    U              UAGAGUUACA
      GCA  UCCCAGG GAG UAG AGGUUGUAUAGUU              \
      CGU  AGGGUUC UUC AUC UCCGACAUGUCAA              A
   CA^ UC-       CU    G    C              UAGAGGGAAC
       90        80        70        60         50
``` |
| rno-let-7b | dG = -44.0 | ```
  ---| U                       -  -----    CA      A
      GGG GAGGUAGUAGGUUGUGUGGUU UC    AGGG  GUG    U
      CCC UUCCGUCAUCCAACAUAUCAA AG    UCCC  CGC    G
   AGU^  -                      U    AAGCC  --     U
``` |
| rno-mir-7-1 | dG = -46.8 | ```
   U--|  U  U    A U       A    A     U       --     A
       UGGA GU GGCCU GU CUGUGUGG AGACU GUGAUUU GUUGUU   UUUAG U
       AUCU CA CCGGA CA GGUAUACC UCUGA CACUAAA CAACAG   GAAUC A
    GAC^   C  -    - C        G  -     -       CA      A
``` |
| rno-mir-7-2 | dG = -29.1 | ```
   ---| C   C   A   AGU    U     UG C
       CCAGC CUGU UGG AGACU   GAUUU GUUGUU U U
       GGUUG GGUA ACC UCUGA   CUGAA CAACAAC G G
    ACU^   U   C   G   CC-    -      CU U
``` |
| rno-mir-16-2 | dG = -36.9 | ```
   ----|   UC   CU        UA      C  AG    AAU
        CUUGU CGCU AGCAGCACG AAUAUGG GU UGA  A
        GGACA GUGA UCGUCGUGU UUAUAACC CA AUU  A
     AUAG^   GU   UU        UA      A  A-   AUA
``` |
| rno-mir-24-2 | dG = -53.5 | ```
   -|  U-    CU---     CCGC      G    A       AA    UG U
      GCC CUCC     GGGCU    CUCCUGU CCU CUGAGCUGA  CAGU AU C
      CGG GAGG     CCCGA    GAGGACA GGA GACUUGACU  GUCA UG C
    A^    UC    AUACC     CCU-     A    C       CG    CG A
``` |
| rno-mir-26b | dG = -42.6 | ```
   U|  -    GA   -  U        UC       UG     G
       GC CCGG CCC AGU CAAGUAAU AGGAUAGGU UGGU C
       CG GGCC GGG UCG GUUCAUUA UCUUGUCCG ACCG U
    C^   U   GG   C   -        CC       --    G
``` |
| rno-mir-28 | dG = -41.2 | ```
    |  C  A   GCA                UU--   U-   CUU
      GGU CCU CCC  AGGAGCUCACAGUCUA   GAG UC     \
      UCA GGA GGG  UCCUCGAGUGUUAGAU   CUC AG   U
    ^   C  C   AGG                CACC   UU   UCU
``` |
| rno-mir-30b | dG = -28.1 | ```
    |                U  -           -- U
      AUGUAAACAUCC ACA CUCAGCUG  UCA A
      UGCAUUUGUAGG UGU GGGUCGGU  AGU C
    ^                -   A        UG A
``` |
| rno-mir-30c-2 | dG = -28.0 | ```
      GAGUGA|  UACU     U  ACA      GUGAAA
              CAGA  GUAAACA CCU  CUCUCAGCU    A
              GUCU  CAUUUGU GGA  GAGGGUCGA    G
      UUCC--^  CUCU     C   A--      AAGAAU
``` |
| rno-mir-92-2 | dG = -36.5 | ```
      UGCCCA|  A   A   G    U    CAU     GUGUU
              UUC UCC CAGGU GGGAU AGUGC    UACUU    A
              AAG AGG GUCCG CCCUG UCACG    AUGAA    G
      A-----^  A   A   G    U     UU-     AAAUA
``` |
| rno-mir-93 | dG = -48.2 | ```
      A|  A        CA-      -    U  G   UG UU
         GUC UGGGGGCUC   AAGUGCU GUUCG GCAG UAG  CA   \
         CAG ACCCCCGAG   UUCACGA CGAGU CGUC AUC  GU   G
       A^   G        CCC      U    -   -    CA CC
``` |

Figure 1B

| | | |
|---|---|---|
| rno-mir-99a | dG = -29.5 | ` ⎜   A           UC  U      G  AAG`<br>`CAUA ACCCGUAGA   CGA CUUGUG UG    U`<br>`GUGU UGGGUAUCU   GCU GAACAC GC    G`<br>`   ^    C         UU  C      -  CAG` |
| rno-mir-125b-2 | dG = -33.3 | `-⎜    UC  UG   C    A          GG-   U`<br>`CCUAG   CC  AGA CCU ACUUGUGA     UAU U`<br>`GGAUC   GG  UCU GGA UGAACACU    ,AUG U`<br>`C^      CA  GU   C    C          ACA  A` |
| rno-mir-130a | dG = -24.7 | `GA-⎜        C     UG  A  GUC ⎜ A`<br>`   GCUCUUUU ACAUG  CU  CU    UAC  C`<br>`   CGGGAAAA UGUAAC GA  GA    AUG  G`<br>`CUA^        U     GU   C  GCC ⎜ U` |
| rno-mir-138-1 | dG = -50.6 | `CUCUG⎜ UG    U        AG              UCA       GCCAA`<br>`     GCA  GUGU  GUGGGAC   CUGGUGUUGUGAA    GGCCGUU     \`<br>`     CGU  CACG  CACUCUG   GACCACAACACUU    UCGGCAA      U`<br>`A----^ --    U        G-              CA-       GAGAC` |
| rno-mir-138-2 | dG = -29.1 | `CAG--⎜          UCA       AC---    CAAC`<br>`     CUGGUGUUGUGAA    GGCCG       GAG      \`<br>`     GACCACAGCACUU    UCGGC       CUC       G`<br>`GUUGG^          UA-       CCAUU    CUAC` |
| rno-mir-146 | dG = -29.3 | ` ⎜   CU           C      --  G`<br>`AGCU  GAGAACUGAAUU CAUGGGUU  AUA C`<br>`UCGA  UUCUUGACUUGA GUGUCCAG  UGU A`<br>` ^    U-           A      AC  A` |

Figure 1B dG = -33.9 rno-miR-B

```
ref|NW_048043.1|RnX_2568 Rattus norvegicus chromosome X WGS supercontig

R. norvegicus  NW_048043.1    3077508 CACACTGTAGGCCTCATTCATTAAATGTTTGTTGAATGAAAAAATGAATCATCAACAGACATTAATTGGGCGCCCTGCTCTGTG 3077429
H. sapiens     AC004386.1        5060 CACATTGTAGGCCTCATTCATTAAATGTTGTTGAATGAAAAATGAATCATCAACAGACATTAATTGGGCGCCTGCTCTGTG    4982
M. musculus    AL683845.15      39424 CACATTGTAGGCCTCATTAAAATGTTTGTTGAATGAAAAATGAATCATCAACAGACATTAATTGGGCGCCCTGCTCTGTG     39346
```

Figure 2B mmu-miR-B, hsa-miR-B smallRNA-1

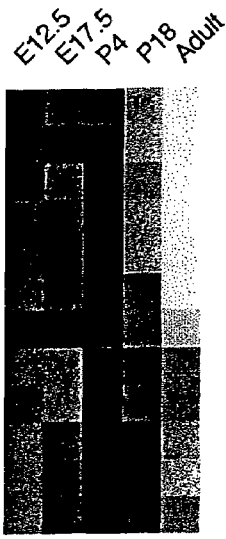

| microRNA | oligo | oligo sequence | |
|---|---|---|---|
| mmu-miR-23b | EAM261 | GTGGTAATCCCTGGCAATGTGAT | |
| mmu-miR-139 | EAM206 | AGACACGTGCACTGTAGA | |
| mmu-miR-29b | EAM119 | AACACTGATTTCAAATGGTGCTA | miR-29 family |
| mmu-miR-29c | EAM279 | TAACCGATTTCAAATGGTGCTA | |
| mmu-miR-29a | EAM268 | AACCGATTTCAGATGGTGCTAG | |
| mmu-miR-132 | EAM137 | CCGACCATGGCTGTAGACTGTTA | |
| mmu-miR-125b | EAM105 | TCACAAGTTAGGGTCTCAGGGA | |
| mmu-miR-129 | EAM289 | AACAAGCCCAGACCGCAAAAAG | |
| mmu-miR-22 | EAM255 | ACAGTTCTTCAACTGGCAGCTT | |
| mmu-let-7h[14] | EAM182 | AACTGTACACACTACTACCTCA | |
| mmu-miR-128b | EAM195 | GAAAGAGACCGGTTCACTGTGA | miR-128 family |
| mmu-miR-128a | EAM194 | AAAAGAGACCGGTTCACTGTGA | |

Figure 8A

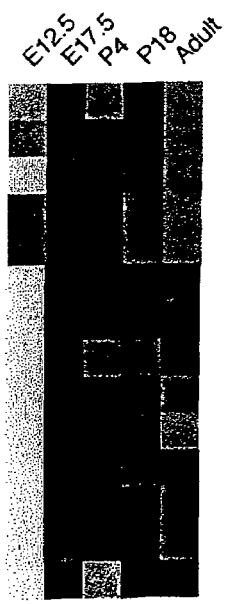

| microRNA | oligo | oligo sequence | |
|---|---|---|---|
| hsa-miR-199b | EAM235 | GAACAGATAGTCTAAACACTGGG | miR-199 family |
| mmu-miR-199b | EAM282 | GAACAGGTAGTCTAAACACTGGG | |
| mmu-miR-130a | EAM159 | ATGCCCTTTTAACATTGCACTG | |
| mmu-miR-18 | EAM225 | TATCTGCACTAGATGCACCTTA | |
| mmu-miR-19b | EAM237 | TCAGTTTTGCATGGATTTGCACA | |
| mmu-miR-181a | EAM226 | ACTCACCGACAGCGTTGAATGTT | miR-181 family |
| mmu-miR-181b | EAM227 | AACCCACCGACAGCAATGAATGTT | |
| mmu-miR-181c | EAM228 | ACTCACCGACAGGTTGAATGTT | |
| smallRNA-12 | EAM156 | ACTCACCGAGAGCGTTGAATGTT | |
| mmu-miR-9 | EAM276 | TCATACAGCTAGATAACCAAAGA | |
| mmu-miR-324-5p | EAM133 | ACACCAATGCCCTAGGGGATGCG | |
| mmu-miR-320 | EAM175 | TCGCCCTCTCAACCCAGCTTTT | |
| mmu-miR-149 | EAM216 | GGAGTGAAGACACGGAGCCAGA | |
| mmu-miR-134 | EAM202 | TCCCTCTGGTCAACCAGTCACA | |

SEQUENCE LISTING

```
<160> NUMBER OF SEQ ID NOS: 387

<210> SEQ ID NO 1
<211> LENGTH: 20
<212> TYPE: DNA
<213> ORGANISM: Mus musculus

<400> SEQUENCE: 1
tggtgtcaga agtgggatac                                                      20

<210> SEQ ID NO 2
<211> LENGTH: 23
<212> TYPE: DNA
<213> ORGANISM: Mus musculus

<400> SEQUENCE: 2
actcaccgag agcgttgaat gtt                                                  23

<210> SEQ ID NO 3
<211> LENGTH: 22
<212> TYPE: DNA
<213> ORGANISM: Mus musculus

<400> SEQUENCE: 3
aactgtacac actactacct ca                                                   22

<210> SEQ ID NO 4
<211> LENGTH: 19
<212> TYPE: DNA
<213> ORGANISM: Mus musculus

<400> SEQUENCE: 4
caatgcaaca gcaatgcac                                                       19

<210> SEQ ID NO 5
<211> LENGTH: 23
```

-continued

```
<212> TYPE: DNA
<213> ORGANISM: Mus musculus

<400> SEQUENCE: 5
tccatcatca aaacaaatgg agt                                              23

<210> SEQ ID NO 6
<211> LENGTH: 23
<212> TYPE: DNA
<213> ORGANISM: Mus musculus

<400> SEQUENCE: 6
tccatcatga aagaaatgg agt                                               23

<210> SEQ ID NO 7
<211> LENGTH: 21
<212> TYPE: DNA
<213> ORGANISM: Mus musculus

<400> SEQUENCE: 7
tggcattcac cgcgtgcctt a                                                21

<210> SEQ ID NO 8
<211> LENGTH: 21
<212> TYPE: DNA
<213> ORGANISM: Mus musculus

<400> SEQUENCE: 8
tggcattcag cgggtgcctt a                                                21

<210> SEQ ID NO 9
<211> LENGTH: 22
<212> TYPE: DNA
<213> ORGANISM: Mus musculus

<400> SEQUENCE: 9
tcacaagtta gggtctcagg ga                                               22

<210> SEQ ID NO 10
<211> LENGTH: 22
<212> TYPE: DNA
<213> ORGANISM: Mus musculus

<400> SEQUENCE: 10
tcacaagtaa gggtgtcagg ga                                               22

<210> SEQ ID NO 11
<211> LENGTH: 21
<212> TYPE: DNA
<213> ORGANISM: Mus musculus

<400> SEQUENCE: 11
tgttcctgct gaactgagcc a                                                21

<210> SEQ ID NO 12
<211> LENGTH: 21
<212> TYPE: DNA
<213> ORGANISM: Mus musculus

<400> SEQUENCE: 12
tgttcctggt gaagtgagcc a                                                21

<210> SEQ ID NO 13
```

```
<211> LENGTH: 24
<212> TYPE: DNA
<213> ORGANISM: Mus musculus

<400> SEQUENCE: 13
aacaacaaaa tcactagtct tcca                                              24

<210> SEQ ID NO 14
<211> LENGTH: 24
<212> TYPE: DNA
<213> ORGANISM: Mus musculus

<400> SEQUENCE: 14
aacaacaaaa tgagtagtct tcca                                              24

<210> SEQ ID NO 15
<211> LENGTH: 21
<212> TYPE: DNA
<213> ORGANISM: Artificial Sequence
<220> FEATURE:
<223> OTHER INFORMATION: Probe sequence

<400> SEQUENCE: 15
gcatgcatgc atgcatgcat g                                                 21

<210> SEQ ID NO 16
<211> LENGTH: 21
<212> TYPE: DNA
<213> ORGANISM: Mus musculus

<400> SEQUENCE: 16
gtggtagcgc agtgcgtaga a                                                 21

<210> SEQ ID NO 17
<211> LENGTH: 21
<212> TYPE: DNA
<213> ORGANISM: Mus musculus

<400> SEQUENCE: 17
ggtgatgccc tgaatgttgt c                                                 21

<210> SEQ ID NO 18
<211> LENGTH: 21
<212> TYPE: DNA
<213> ORGANISM: Mus musculus

<400> SEQUENCE: 18
tgtcatggat gaccttggcc a                                                 21

<210> SEQ ID NO 19
<211> LENGTH: 21
<212> TYPE: DNA
<213> ORGANISM: Mus musculus

<400> SEQUENCE: 19
cttttgacat tgaagggagc t                                                 21

<210> SEQ ID NO 20
<211> LENGTH: 23
<212> TYPE: DNA
<213> ORGANISM: Mus musculus

<400> SEQUENCE: 20
taactgtaca aactactacc tca                                               23
```

```
<210> SEQ ID NO 21
<211> LENGTH: 23
<212> TYPE: DNA
<213> ORGANISM: Mus musculus

<400> SEQUENCE: 21
taactgtaga aagtactacc tca                                        23

<210> SEQ ID NO 22
<211> LENGTH: 22
<212> TYPE: DNA
<213> ORGANISM: Mus musculus

<400> SEQUENCE: 22
acaggttaaa gggtctcagg ga                                         22

<210> SEQ ID NO 23
<211> LENGTH: 22
<212> TYPE: DNA
<213> ORGANISM: Mus musculus

<400> SEQUENCE: 23
acaggtaaaa gggtgtcagg ga                                         22

<210> SEQ ID NO 24
<211> LENGTH: 22
<212> TYPE: DNA
<213> ORGANISM: Mus musculus

<400> SEQUENCE: 24
cgccaatatt tacgtgctgc ta                                         22

<210> SEQ ID NO 25
<211> LENGTH: 22
<212> TYPE: DNA
<213> ORGANISM: Mus musculus

<400> SEQUENCE: 25
cgccaatatt aaggtgctgc ta                                         22

<210> SEQ ID NO 26
<211> LENGTH: 22
<212> TYPE: DNA
<213> ORGANISM: Mus musculus

<400> SEQUENCE: 26
taaccgattt caaatggtgc ta                                         22

<210> SEQ ID NO 27
<211> LENGTH: 22
<212> TYPE: DNA
<213> ORGANISM: Mus musculus

<400> SEQUENCE: 27
taaccgattt gaaaaggtgc ta                                         22

<210> SEQ ID NO 28
<211> LENGTH: 23
<212> TYPE: DNA
<213> ORGANISM: Mus musculus

<400> SEQUENCE: 28
```
aacactgatt tcaaatggtg cta 23

<210> SEQ ID NO 29
<211> LENGTH: 23
<212> TYPE: DNA
<213> ORGANISM: Mus musculus

<400> SEQUENCE: 29
aacactgatt tgaaaaggtg cta 23

<210> SEQ ID NO 30
<211> LENGTH: 21
<212> TYPE: DNA
<213> ORGANISM: Mus musculus

<400> SEQUENCE: 30
cacaagatcg gatctacggg t 21

<210> SEQ ID NO 31
<211> LENGTH: 21
<212> TYPE: DNA
<213> ORGANISM: Mus musculus

<400> SEQUENCE: 31
cacaagatgg gatgtacggg t 21

<210> SEQ ID NO 32
<211> LENGTH: 22
<212> TYPE: DNA
<213> ORGANISM: Mus musculus

<400> SEQUENCE: 32
aactatgcaa cctactacct ct 22

<210> SEQ ID NO 33
<211> LENGTH: 22
<212> TYPE: DNA
<213> ORGANISM: Mus musculus

<400> SEQUENCE: 33
aactatgcaa cgtagtacct ct 22

<210> SEQ ID NO 34
<211> LENGTH: 23
<212> TYPE: DNA
<213> ORGANISM: Mus musculus

<400> SEQUENCE: 34
cggcctgatt cacaacacca gct 23

<210> SEQ ID NO 35
<211> LENGTH: 23
<212> TYPE: DNA
<213> ORGANISM: Mus musculus

<400> SEQUENCE: 35
cggcctgatt gagaacacca gct 23

<210> SEQ ID NO 36
<211> LENGTH: 23
<212> TYPE: DNA
<213> ORGANISM: Mus musculus

<400> SEQUENCE: 36

```
tcatagccct gtacaatgct gct                                             23

<210> SEQ ID NO 37
<211> LENGTH: 23
<212> TYPE: DNA
<213> ORGANISM: Mus musculus

<400> SEQUENCE: 37
tcatagccct gaagaatgct gct                                             23

<210> SEQ ID NO 38
<211> LENGTH: 22
<212> TYPE: DNA
<213> ORGANISM: Mus musculus

<400> SEQUENCE: 38
aggcattcac cgcgtgcctt at                                              22

<210> SEQ ID NO 39
<211> LENGTH: 22
<212> TYPE: DNA
<213> ORGANISM: Mus musculus

<400> SEQUENCE: 39
aggcattcag cgggtgcctt at                                              22

<210> SEQ ID NO 40
<211> LENGTH: 23
<212> TYPE: DNA
<213> ORGANISM: Mus musculus

<400> SEQUENCE: 40
acaggccggg acaagtgcaa tat                                             23

<210> SEQ ID NO 41
<211> LENGTH: 23
<212> TYPE: DNA
<213> ORGANISM: Mus musculus

<400> SEQUENCE: 41
acaggccggg agaagagcaa tat                                             23

<210> SEQ ID NO 42
<211> LENGTH: 23
<212> TYPE: DNA
<213> ORGANISM: Mus musculus

<400> SEQUENCE: 42
acaccaatgc cctaggggat gcg                                             23

<210> SEQ ID NO 43
<211> LENGTH: 23
<212> TYPE: DNA
<213> ORGANISM: Mus musculus

<400> SEQUENCE: 43
acaccaatgg cgtaggggat gcg                                             23

<210> SEQ ID NO 44
<211> LENGTH: 21
<212> TYPE: DNA
<213> ORGANISM: Mus musculus
```

```
<400> SEQUENCE: 44
caacaaacat ttaatgaggc c                                              21

<210> SEQ ID NO 45
<211> LENGTH: 21
<212> TYPE: DNA
<213> ORGANISM: Mus musculus

<400> SEQUENCE: 45
caacaaagat taaatgaggc c                                              21

<210> SEQ ID NO 46
<211> LENGTH: 23
<212> TYPE: DNA
<213> ORGANISM: Mus musculus

<400> SEQUENCE: 46
ccgaccatgg ctgtagactg tta                                            23

<210> SEQ ID NO 47
<211> LENGTH: 23
<212> TYPE: DNA
<213> ORGANISM: Mus musculus

<400> SEQUENCE: 47
ccgaccatgg gtgaagactg tta                                            23

<210> SEQ ID NO 48
<211> LENGTH: 23
<212> TYPE: DNA
<213> ORGANISM: Mus musculus

<400> SEQUENCE: 48
taacccatgg aattcagttc tca                                            23

<210> SEQ ID NO 49
<211> LENGTH: 23
<212> TYPE: DNA
<213> ORGANISM: Mus musculus

<400> SEQUENCE: 49
taacccatgg aaatgagttc tca                                            23

<210> SEQ ID NO 50
<211> LENGTH: 23
<212> TYPE: DNA
<213> ORGANISM: Mus musculus

<400> SEQUENCE: 50
taactataca atctactacc tca                                            23

<210> SEQ ID NO 51
<211> LENGTH: 23
<212> TYPE: DNA
<213> ORGANISM: Mus musculus

<400> SEQUENCE: 51
taactataca atgtagtacc tca                                            23

<210> SEQ ID NO 52
<211> LENGTH: 23
<212> TYPE: DNA
<213> ORGANISM: Mus musculus
```

```
<400> SEQUENCE: 52
taaccataca acctattacc tca                                              23

<210> SEQ ID NO 53
<211> LENGTH: 23
<212> TYPE: DNA
<213> ORGANISM: Mus musculus

<400> SEQUENCE: 53
taaccataga acgtattacc tca                                              23

<210> SEQ ID NO 54
<211> LENGTH: 22
<212> TYPE: DNA
<213> ORGANISM: Mus musculus

<400> SEQUENCE: 54
aaccatacaa cctactacct ca                                               22

<210> SEQ ID NO 55
<211> LENGTH: 22
<212> TYPE: DNA
<213> ORGANISM: Mus musculus

<400> SEQUENCE: 55
aaccatacaa gctagtacct ca                                               22

<210> SEQ ID NO 56
<211> LENGTH: 22
<212> TYPE: DNA
<213> ORGANISM: Mus musculus

<400> SEQUENCE: 56
aaccacacaa cctactacct ca                                               22

<210> SEQ ID NO 57
<211> LENGTH: 22
<212> TYPE: DNA
<213> ORGANISM: Mus musculus

<400> SEQUENCE: 57
aaccacacaa gctagtacct ca                                               22

<210> SEQ ID NO 58
<211> LENGTH: 20
<212> TYPE: DNA
<213> ORGANISM: Mus musculus

<400> SEQUENCE: 58
gcattcaccc gcgtgcctta                                                  20

<210> SEQ ID NO 59
<211> LENGTH: 23
<212> TYPE: DNA
<213> ORGANISM: Mus musculus

<400> SEQUENCE: 59
tcatacagct agataaccaa aga                                              23

<210> SEQ ID NO 60
<211> LENGTH: 18
<212> TYPE: DNA
```

<213> ORGANISM: Mus musculus

<400> SEQUENCE: 60
acaagatcgg atctacgg					18

<210> SEQ ID NO 61
<211> LENGTH: 22
<212> TYPE: DNA
<213> ORGANISM: Mus musculus

<400> SEQUENCE: 61
actttcggtt atctagcttt at				22

<210> SEQ ID NO 62
<211> LENGTH: 22
<212> TYPE: DNA
<213> ORGANISM: Mus musculus

<400> SEQUENCE: 62
aactatacaa cctactacct ca				22

<210> SEQ ID NO 63
<211> LENGTH: 21
<212> TYPE: DNA
<213> ORGANISM: Mus musculus

<400> SEQUENCE: 63
aaagagaccg gttcactgtg a					21

<210> SEQ ID NO 64
<211> LENGTH: 23
<212> TYPE: DNA
<213> ORGANISM: Mus musculus

<400> SEQUENCE: 64
tccatcatca aaacaaatgg agt				23

<210> SEQ ID NO 65
<211> LENGTH: 23
<212> TYPE: DNA
<213> ORGANISM: Mus musculus

<400> SEQUENCE: 65
actcaccgag agcgttgaat gtt				23

<210> SEQ ID NO 66
<211> LENGTH: 20
<212> TYPE: DNA
<213> ORGANISM: Mus musculus

<400> SEQUENCE: 66
tggtgtcaga agtgggatac					20

<210> SEQ ID NO 67
<211> LENGTH: 20
<212> TYPE: DNA
<213> ORGANISM: Mus musculus

<400> SEQUENCE: 67
tacagctaaa taaccaaaga					20

<210> SEQ ID NO 68
<211> LENGTH: 22

```
<212> TYPE: DNA
<213> ORGANISM: Mus musculus

<400> SEQUENCE: 68 atgcccttt  aacattgcac  tg                                          22

<210> SEQ ID NO 69
<211> LENGTH: 22
<212> TYPE: DNA
<213> ORGANISM: Mus musculus

<400> SEQUENCE: 69
aacctatcct  gaattacttg  aa                                          22

<210> SEQ ID NO 70
<211> LENGTH: 22
<212> TYPE: DNA
<213> ORGANISM: Mus musculus

<400> SEQUENCE: 70
ctcaatagac  tgtgagctcc  tt                                          22

<210> SEQ ID NO 71
<211> LENGTH: 22
<212> TYPE: DNA
<213> ORGANISM: Mus musculus

<400> SEQUENCE: 71
atcaaggtcc  gctgtgaaca  cg                                          22

<210> SEQ ID NO 72
<211> LENGTH: 23
<212> TYPE: DNA
<213> ORGANISM: Mus musculus

<400> SEQUENCE: 72
tccataaagt  aggaaacact  aca                                         23

<210> SEQ ID NO 73
<211> LENGTH: 21
<212> TYPE: DNA
<213> ORGANISM: Mus musculus

<400> SEQUENCE: 73
gagtgcttgc  taggtgccaa  g                                           21

<210> SEQ ID NO 74
<211> LENGTH: 23
<212> TYPE: DNA
<213> ORGANISM: Mus musculus

<400> SEQUENCE: 74
gggagtgaag  acacggagcc  aga                                         23

<210> SEQ ID NO 75
<211> LENGTH: 21
<212> TYPE: DNA
<213> ORGANISM: Mus musculus

<400> SEQUENCE: 75
gcctatcctg  gattacttga  a                                           21

<210> SEQ ID NO 76
```

```
<211> LENGTH: 19
<212> TYPE: DNA
<213> ORGANISM: Mus musculus

<400> SEQUENCE: 76
gttgtggtca cttacaatt                                                 19

<210> SEQ ID NO 77
<211> LENGTH: 20
<212> TYPE: DNA
<213> ORGANISM: Mus musculus

<400> SEQUENCE: 77
ctatacaacc tcctacctca                                                20

<210> SEQ ID NO 78
<211> LENGTH: 22
<212> TYPE: DNA
<213> ORGANISM: Mus musculus

<400> SEQUENCE: 78
aacagcacaa actactacct ca                                             22

<210> SEQ ID NO 79
<211> LENGTH: 22
<212> TYPE: DNA
<213> ORGANISM: Mus musculus

<400> SEQUENCE: 79
tggcattcac cgccgtgcct ta                                             22

<210> SEQ ID NO 80
<211> LENGTH: 23
<212> TYPE: DNA
<213> ORGANISM: Mus musculus

<400> SEQUENCE: 80
ctacgcgtat tcttaagcaa taa                                            23

<210> SEQ ID NO 81
<211> LENGTH: 19
<212> TYPE: DNA
<213> ORGANISM: Mus musculus

<400> SEQUENCE: 81
ctcgtactga gcaggatta                                                 19

<210> SEQ ID NO 82
<211> LENGTH: 20
<212> TYPE: DNA
<213> ORGANISM: Mus musculus

<400> SEQUENCE: 82
gtctcgaaaa ggtagcgttc                                                20

<210> SEQ ID NO 83
<211> LENGTH: 20
<212> TYPE: DNA
<213> ORGANISM: Mus musculus

<400> SEQUENCE: 83
agaaaacatg ctccaggtga                                                20
```

```
<210> SEQ ID NO 84
<211> LENGTH: 22
<212> TYPE: DNA
<213> ORGANISM: Mus musculus

<400> SEQUENCE: 84
tcgccctctc aacccagctt tt                                    22

<210> SEQ ID NO 85
<211> LENGTH: 21
<212> TYPE: DNA
<213> ORGANISM: Mus musculus

<400> SEQUENCE: 85
tacagtactg tgatagctga a                                     21

<210> SEQ ID NO 86
<211> LENGTH: 21
<212> TYPE: DNA
<213> ORGANISM: Mus musculus

<400> SEQUENCE: 86
ttcagctatc acagtactgt a                                     21

<210> SEQ ID NO 87
<211> LENGTH: 22
<212> TYPE: DNA
<213> ORGANISM: Mus musculus

<400> SEQUENCE: 87
tgccaatatt tctgtgctgc ta                                    22

<210> SEQ ID NO 88
<211> LENGTH: 21
<212> TYPE: DNA
<213> ORGANISM: Mus musculus

<400> SEQUENCE: 88
actatgcaac ctactacctc t                                     21

<210> SEQ ID NO 89
<211> LENGTH: 22
<212> TYPE: DNA
<213> ORGANISM: Mus musculus

<400> SEQUENCE: 89
aactatacaa tctactacct ca                                    22

<210> SEQ ID NO 90
<211> LENGTH: 22
<212> TYPE: DNA
<213> ORGANISM: Mus musculus

<400> SEQUENCE: 90
aactatacaa tctactacct ca                                    22

<210> SEQ ID NO 91
<211> LENGTH: 22
<212> TYPE: DNA
<213> ORGANISM: Mus musculus

<400> SEQUENCE: 91
aactgtacac actactacct ca                                    22
```

```
<210> SEQ ID NO 92
<211> LENGTH: 19
<212> TYPE: DNA
<213> ORGANISM: Mus musculus

<400> SEQUENCE: 92
agcacaaact actacctca                                                   19

<210> SEQ ID NO 93
<211> LENGTH: 22
<212> TYPE: DNA
<213> ORGANISM: Mus musculus

<400> SEQUENCE: 93
cacaagttcg gatctacggg tt                                               22

<210> SEQ ID NO 94
<211> LENGTH: 23
<212> TYPE: DNA
<213> ORGANISM: Mus musculus

<400> SEQUENCE: 94
tcatagccct gtacaatgct gct                                              23

<210> SEQ ID NO 95
<211> LENGTH: 24
<212> TYPE: DNA
<213> ORGANISM: Mus musculus

<400> SEQUENCE: 95
gctacctgca ctgtaagcac tttt                                             24

<210> SEQ ID NO 96
<211> LENGTH: 23
<212> TYPE: DNA
<213> ORGANISM: Mus musculus

<400> SEQUENCE: 96
tgatagccct gtacaatgct gct                                              23

<210> SEQ ID NO 97
<211> LENGTH: 21
<212> TYPE: DNA
<213> ORGANISM: Mus musculus

<400> SEQUENCE: 97 aatgcccta aaaatcctta t                                                 21

<210> SEQ ID NO 98
<211> LENGTH: 23
<212> TYPE: DNA
<213> ORGANISM: Mus musculus

<400> SEQUENCE: 98
cacaaattcg gatctacagg gta                                              23

<210> SEQ ID NO 99
<211> LENGTH: 22
<212> TYPE: DNA
<213> ORGANISM: Mus musculus

<400> SEQUENCE: 99
acaaattcgg ttctacaggg ta                                               22
```

```
<210> SEQ ID NO 100
<211> LENGTH: 23
<212> TYPE: DNA
<213> ORGANISM: Mus musculus

<400> SEQUENCE: 100
acaaacacca ttgtcacact cca                                              23

<210> SEQ ID NO 101
<211> LENGTH: 21
<212> TYPE: DNA
<213> ORGANISM: Mus musculus

<400> SEQUENCE: 101
cgcgtaccaa aagtaataat g                                                21

<210> SEQ ID NO 102
<211> LENGTH: 23
<212> TYPE: DNA
<213> ORGANISM: Mus musculus

<400> SEQUENCE: 102
cacaggttaa agggtctcag gga                                              23

<210> SEQ ID NO 103
<211> LENGTH: 22
<212> TYPE: DNA
<213> ORGANISM: Mus musculus

<400> SEQUENCE: 103
aaaagagacc ggttcactgt ga                                               22

<210> SEQ ID NO 104
<211> LENGTH: 22
<212> TYPE: DNA
<213> ORGANISM: Mus musculus

<400> SEQUENCE: 104
gaaagagacc ggttcactgt ga                                               22

<210> SEQ ID NO 105
<211> LENGTH: 21
<212> TYPE: DNA
<213> ORGANISM: Mus musculus

<400> SEQUENCE: 105
gcaagcccag accgaaaaaa g                                                21

<210> SEQ ID NO 106
<211> LENGTH: 21
<212> TYPE: DNA
<213> ORGANISM: Mus musculus

<400> SEQUENCE: 106
gcaagcccag accgcaaaaa g                                                21

<210> SEQ ID NO 107
<211> LENGTH: 20
<212> TYPE: DNA
<213> ORGANISM: Mus musculus

<400> SEQUENCE: 107
```

-continued gcccttttcat cattgcactg                                              20

<210> SEQ ID NO 108
<211> LENGTH: 23
<212> TYPE: DNA
<213> ORGANISM: Mus musculus

<400> SEQUENCE: 108
acgaccatgg ctgtagactg tta                                           23

<210> SEQ ID NO 109
<211> LENGTH: 22
<212> TYPE: DNA
<213> ORGANISM: Mus musculus

<400> SEQUENCE: 109
acagctggtt gaaggggacc aa                                            22

<210> SEQ ID NO 110
<211> LENGTH: 21
<212> TYPE: DNA
<213> ORGANISM: Mus musculus

<400> SEQUENCE: 110
tagctggttg aaggggacca a                                             21

<210> SEQ ID NO 111
<211> LENGTH: 22
<212> TYPE: DNA
<213> ORGANISM: Mus musculus

<400> SEQUENCE: 111
tccctctggt caaccagtca ca                                            22

<210> SEQ ID NO 112
<211> LENGTH: 24
<212> TYPE: DNA
<213> ORGANISM: Mus musculus

<400> SEQUENCE: 112
ttcacatagg aataaaaagc cata                                          24

<210> SEQ ID NO 113
<211> LENGTH: 24
<212> TYPE: DNA
<213> ORGANISM: Mus musculus

<400> SEQUENCE: 113
atcacatagg aataaaaagc cata                                          24

<210> SEQ ID NO 114
<211> LENGTH: 17
<212> TYPE: DNA
<213> ORGANISM: Mus musculus

<400> SEQUENCE: 114
gattcacaac accagct                                                  17

<210> SEQ ID NO 115
<211> LENGTH: 18
<212> TYPE: DNA
<213> ORGANISM: Mus musculus

<400> SEQUENCE: 115

-continued agacacgtgc actgtaga                                              18

<210> SEQ ID NO 116
<211> LENGTH: 21
<212> TYPE: DNA
<213> ORGANISM: Mus musculus

<400> SEQUENCE: 116
ctaccatagg gtaaaaccac t                                          21

<210> SEQ ID NO 117
<211> LENGTH: 21
<212> TYPE: DNA
<213> ORGANISM: Mus musculus

<400> SEQUENCE: 117
ccatctttac cagacagtgt t                                          21

<210> SEQ ID NO 118
<211> LENGTH: 20
<212> TYPE: DNA
<213> ORGANISM: Mus musculus

<400> SEQUENCE: 118
gtagtgcttt ctactttatg                                            20

<210> SEQ ID NO 119
<211> LENGTH: 22
<212> TYPE: DNA
<213> ORGANISM: Mus musculus

<400> SEQUENCE: 119
tgagctacag tgcttcatct ca                                         22

<210> SEQ ID NO 120
<211> LENGTH: 22
<212> TYPE: DNA
<213> ORGANISM: Mus musculus

<400> SEQUENCE: 120
ctagtacatc atctatactg ta                                         22

<210> SEQ ID NO 121
<211> LENGTH: 24
<212> TYPE: DNA
<213> ORGANISM: Mus musculus

<400> SEQUENCE: 121
aagggattcc tgggaaaact ggac                                       24

<210> SEQ ID NO 122
<211> LENGTH: 23
<212> TYPE: DNA
<213> ORGANISM: Mus musculus

<400> SEQUENCE: 122
aaacccatgg aattcagttc tca                                        23

<210> SEQ ID NO 123
<211> LENGTH: 22
<212> TYPE: DNA
<213> ORGANISM: Mus musculus

<400> SEQUENCE: 123
acaaagttct gtagtgcact ga                                              22

<210> SEQ ID NO 124
<211> LENGTH: 22
<212> TYPE: DNA
<213> ORGANISM: Mus musculus

<400> SEQUENCE: 124
acaaagttct gtgatgcact ga                                              22

<210> SEQ ID NO 125
<211> LENGTH: 22
<212> TYPE: DNA
<213> ORGANISM: Mus musculus

<400> SEQUENCE: 125
ggagtgaaga cacggagcca ga                                              22

<210> SEQ ID NO 126
<211> LENGTH: 23
<212> TYPE: DNA
<213> ORGANISM: Mus musculus

<400> SEQUENCE: 126
acactggtac aagggttggg aga                                             23

<210> SEQ ID NO 127
<211> LENGTH: 21
<212> TYPE: DNA
<213> ORGANISM: Mus musculus

<400> SEQUENCE: 127
ccaagttctg tcatgcactg a                                               21

<210> SEQ ID NO 128
<211> LENGTH: 20
<212> TYPE: DNA
<213> ORGANISM: Mus musculus

<400> SEQUENCE: 128 tcactttttgt gactatgcaa                                                20

<210> SEQ ID NO 129
<211> LENGTH: 22
<212> TYPE: DNA
<213> ORGANISM: Mus musculus

<400> SEQUENCE: 129
cgaaggcaac acggataacc ta                                              22

<210> SEQ ID NO 130
<211> LENGTH: 22
<212> TYPE: DNA
<213> ORGANISM: Mus musculus

<400> SEQUENCE: 130
cccctatcac aattagcatt aa                                              22

<210> SEQ ID NO 131
<211> LENGTH: 22
<212> TYPE: DNA
<213> ORGANISM: Mus musculus -continued

```
<400> SEQUENCE: 131
cacaaaccat tatgtgctgc ta                                              22

<210> SEQ ID NO 132
<211> LENGTH: 22
<212> TYPE: DNA
<213> ORGANISM: Mus musculus

<400> SEQUENCE: 132
tgtaaaccat gatgtgctgc ta                                              22

<210> SEQ ID NO 133
<211> LENGTH: 24
<212> TYPE: DNA
<213> ORGANISM: Mus musculus

<400> SEQUENCE: 133
actacctgca ctgtaagcac tttg                                            24

<210> SEQ ID NO 134
<211> LENGTH: 22
<212> TYPE: DNA
<213> ORGANISM: Mus musculus

<400> SEQUENCE: 134
tatctgcact agatgcacct ta                                              22

<210> SEQ ID NO 135
<211> LENGTH: 23
<212> TYPE: DNA
<213> ORGANISM: Mus musculus

<400> SEQUENCE: 135
actcaccgac agcgttgaat gtt                                             23

<210> SEQ ID NO 136
<211> LENGTH: 24
<212> TYPE: DNA
<213> ORGANISM: Mus musculus

<400> SEQUENCE: 136
aacccaccga cagcaatgaa tgtt                                            24

<210> SEQ ID NO 137
<211> LENGTH: 22
<212> TYPE: DNA
<213> ORGANISM: Mus musculus

<400> SEQUENCE: 137
actcaccgac aggttgaatg tt                                              22

<210> SEQ ID NO 138
<211> LENGTH: 22
<212> TYPE: DNA
<213> ORGANISM: Mus musculus

<400> SEQUENCE: 138
tgtgagttct accattgcca aa                                              22

<210> SEQ ID NO 139
<211> LENGTH: 23
<212> TYPE: DNA
```

<213> ORGANISM: Mus musculus

<400> SEQUENCE: 139
cagtgaattc taccagtgcc ata        23

<210> SEQ ID NO 140
<211> LENGTH: 21
<212> TYPE: DNA
<213> ORGANISM: Mus musculus

<400> SEQUENCE: 140
cggctgcaac acaagacacg a        21

<210> SEQ ID NO 141
<211> LENGTH: 21
<212> TYPE: DNA
<213> ORGANISM: Mus musculus

<400> SEQUENCE: 141
ggctgtcaat tcataggtca g        21

<210> SEQ ID NO 142
<211> LENGTH: 22
<212> TYPE: DNA
<213> ORGANISM: Mus musculus

<400> SEQUENCE: 142
cccaacaaca tgaaactacc ta        22

<210> SEQ ID NO 143
<211> LENGTH: 23
<212> TYPE: DNA
<213> ORGANISM: Mus musculus

<400> SEQUENCE: 143
gaacaggtag tctgaacact ggg        23

<210> SEQ ID NO 144
<211> LENGTH: 23
<212> TYPE: DNA
<213> ORGANISM: Mus musculus

<400> SEQUENCE: 144
gaacagatag tctaaacact ggg        23

<210> SEQ ID NO 145
<211> LENGTH: 23
<212> TYPE: DNA
<213> ORGANISM: Mus musculus

<400> SEQUENCE: 145
tcagttttgc atagatttgc aca        23

<210> SEQ ID NO 146
<211> LENGTH: 23
<212> TYPE: DNA
<213> ORGANISM: Mus musculus

<400> SEQUENCE: 146
tcagttttgc atggatttgc aca        23

<210> SEQ ID NO 147
<211> LENGTH: 22

-continued

```
<212> TYPE: DNA
<213> ORGANISM: Mus musculus

<400> SEQUENCE: 147
atacatactt ctttacattc ca                                              22

<210> SEQ ID NO 148
<211> LENGTH: 22
<212> TYPE: DNA
<213> ORGANISM: Mus musculus

<400> SEQUENCE: 148
atacatactt ctttacattc ca                                              22

<210> SEQ ID NO 149
<211> LENGTH: 23
<212> TYPE: DNA
<213> ORGANISM: Mus musculus

<400> SEQUENCE: 149
ctacctgcac tataagcact tta                                             23

<210> SEQ ID NO 150
<211> LENGTH: 22
<212> TYPE: DNA
<213> ORGANISM: Mus musculus

<400> SEQUENCE: 150
ctagtggtcc taaacatttc ac                                              22

<210> SEQ ID NO 151
<211> LENGTH: 22
<212> TYPE: DNA
<213> ORGANISM: Mus musculus

<400> SEQUENCE: 151
aggcatagga tgacaaaggg aa                                              22

<210> SEQ ID NO 152
<211> LENGTH: 22
<212> TYPE: DNA
<213> ORGANISM: Mus musculus

<400> SEQUENCE: 152
cagactccgg tggaatgaag ga                                              22

<210> SEQ ID NO 153
<211> LENGTH: 22
<212> TYPE: DNA
<213> ORGANISM: Mus musculus

<400> SEQUENCE: 153
tcaacatcag tctgataagc ta                                              22

<210> SEQ ID NO 154
<211> LENGTH: 21
<212> TYPE: DNA
<213> ORGANISM: Mus musculus

<400> SEQUENCE: 154
cagccgctgt cacacgcaca g                                               21

<210> SEQ ID NO 155
```

```
<211> LENGTH: 22
<212> TYPE: DNA
<213> ORGANISM: Mus musculus

<400> SEQUENCE: 155
aggcgaagga tgacaaaggg aa                                              22

<210> SEQ ID NO 156
<211> LENGTH: 21
<212> TYPE: DNA
<213> ORGANISM: Mus musculus

<400> SEQUENCE: 156
ggccgtgact ggagactgtt a                                               21

<210> SEQ ID NO 157
<211> LENGTH: 22
<212> TYPE: DNA
<213> ORGANISM: Mus musculus

<400> SEQUENCE: 157
ggtacaatca acggtcgatg gt                                              22

<210> SEQ ID NO 158
<211> LENGTH: 21
<212> TYPE: DNA
<213> ORGANISM: Mus musculus

<400> SEQUENCE: 158
ctgcctgtct gtgcctgctg t                                               21

<210> SEQ ID NO 159
<211> LENGTH: 21
<212> TYPE: DNA
<213> ORGANISM: Mus musculus

<400> SEQUENCE: 159
gtctgtcaat tcataggtca t                                               21

<210> SEQ ID NO 160
<211> LENGTH: 21
<212> TYPE: DNA
<213> ORGANISM: Mus musculus

<400> SEQUENCE: 160
cacagttgcc agctgagatt a                                               21

<210> SEQ ID NO 161
<211> LENGTH: 24
<212> TYPE: DNA
<213> ORGANISM: Mus musculus

<400> SEQUENCE: 161
atccaatcag ttcctgatgc agta                                            24

<210> SEQ ID NO 162
<211> LENGTH: 21
<212> TYPE: DNA
<213> ORGANISM: Mus musculus

<400> SEQUENCE: 162
acatggttag atcaagcaca a                                               21
```

<210> SEQ ID NO 163
<211> LENGTH: 21
<212> TYPE: DNA
<213> ORGANISM: Mus musculus

<400> SEQUENCE: 163
agaattgcgt ttggacaatc a                                          21

<210> SEQ ID NO 164
<211> LENGTH: 22
<212> TYPE: DNA
<213> ORGANISM: Mus musculus

<400> SEQUENCE: 164
acagttcttc aactggcagc tt                                         22

<210> SEQ ID NO 165
<211> LENGTH: 21
<212> TYPE: DNA
<213> ORGANISM: Mus musculus

<400> SEQUENCE: 165
aaagtgtcag atacggtgtg g                                          21

<210> SEQ ID NO 166
<211> LENGTH: 23
<212> TYPE: DNA
<213> ORGANISM: Mus musculus

<400> SEQUENCE: 166
gaaacccagc agacaatgta gct                                        23

<210> SEQ ID NO 167
<211> LENGTH: 24
<212> TYPE: DNA
<213> ORGANISM: Mus musculus

<400> SEQUENCE: 167
gagacccagt agccagatgt agct                                       24

<210> SEQ ID NO 168
<211> LENGTH: 21
<212> TYPE: DNA
<213> ORGANISM: Mus musculus

<400> SEQUENCE: 168
ggggtatttg acaaactgac a                                          21

<210> SEQ ID NO 169
<211> LENGTH: 21
<212> TYPE: DNA
<213> ORGANISM: Mus musculus

<400> SEQUENCE: 169
ggaaatccct ggcaatgtga t                                          21

<210> SEQ ID NO 170
<211> LENGTH: 23
<212> TYPE: DNA
<213> ORGANISM: Mus musculus

<400> SEQUENCE: 170
gtggtaatcc ctggcaatgt gat                                        23

```
<210> SEQ ID NO 171
<211> LENGTH: 22
<212> TYPE: DNA
<213> ORGANISM: Mus musculus

<400> SEQUENCE: 171
ctgttcctgc tgaactgagc ca                                      22

<210> SEQ ID NO 172
<211> LENGTH: 22
<212> TYPE: DNA
<213> ORGANISM: Mus musculus

<400> SEQUENCE: 172
agcctatcct ggattacttg aa                                      22

<210> SEQ ID NO 173
<211> LENGTH: 20
<212> TYPE: DNA
<213> ORGANISM: Mus musculus

<400> SEQUENCE: 173
cagaacttag ccactgtgaa                                         20

<210> SEQ ID NO 174
<211> LENGTH: 22
<212> TYPE: DNA
<213> ORGANISM: Mus musculus

<400> SEQUENCE: 174
aaccgatttc agatggtgct ag                                      22

<210> SEQ ID NO 175
<211> LENGTH: 23
<212> TYPE: DNA
<213> ORGANISM: Mus musculus

<400> SEQUENCE: 175
aacactgatt tcaaatggtg cta                                     23

<210> SEQ ID NO 176
<211> LENGTH: 23
<212> TYPE: DNA
<213> ORGANISM: Mus musculus

<400> SEQUENCE: 176
aacactgatt tcaaatggtg cta                                     23

<210> SEQ ID NO 177
<211> LENGTH: 22
<212> TYPE: DNA
<213> ORGANISM: Mus musculus

<400> SEQUENCE: 177
aaccgatttc agatggtgct ag                                      22

<210> SEQ ID NO 178
<211> LENGTH: 22
<212> TYPE: DNA
<213> ORGANISM: Mus musculus

<400> SEQUENCE: 178
gctgcaaaca tccgactgaa ag                                      22
```

<210> SEQ ID NO 179
<211> LENGTH: 21
<212> TYPE: DNA
<213> ORGANISM: Mus musculus

<400> SEQUENCE: 179
gctgagtgta ggatgtttac a                                            21

<210> SEQ ID NO 180
<211> LENGTH: 23
<212> TYPE: DNA
<213> ORGANISM: Mus musculus

<400> SEQUENCE: 180
gctgagagtg taggatgttt aca                                          23

<210> SEQ ID NO 181
<211> LENGTH: 22
<212> TYPE: DNA
<213> ORGANISM: Mus musculus

<400> SEQUENCE: 181
cttccagtcg gggatgttta ca                                           22

<210> SEQ ID NO 182
<211> LENGTH: 19
<212> TYPE: DNA
<213> ORGANISM: Mus musculus

<400> SEQUENCE: 182
caatgcaact acaatgcac                                               19

<210> SEQ ID NO 183
<211> LENGTH: 19
<212> TYPE: DNA
<213> ORGANISM: Mus musculus

<400> SEQUENCE: 183
caatgcaaca gcaatgcac                                               19

<210> SEQ ID NO 184
<211> LENGTH: 22
<212> TYPE: DNA
<213> ORGANISM: Mus musculus

<400> SEQUENCE: 184
acaaccagct aagacactgc ca                                           22

<210> SEQ ID NO 185
<211> LENGTH: 23
<212> TYPE: DNA
<213> ORGANISM: Mus musculus

<400> SEQUENCE: 185
tcatacagct agataaccaa aga                                          23

<210> SEQ ID NO 186
<211> LENGTH: 22
<212> TYPE: DNA
<213> ORGANISM: Mus musculus

<400> SEQUENCE: 186

```
gcaaaaatgt gctagtgcca aa                                          22
```

<210> SEQ ID NO 187
<211> LENGTH: 22
<212> TYPE: DNA
<213> ORGANISM: Mus musculus

<400> SEQUENCE: 187

```
aacaatacaa cttactacct ca                                          22
```

<210> SEQ ID NO 188
<211> LENGTH: 22
<212> TYPE: DNA
<213> ORGANISM: Mus musculus

<400> SEQUENCE: 188

```
taaccgattt caaatggtgc ta                                          22
```

<210> SEQ ID NO 189
<211> LENGTH: 22
<212> TYPE: DNA
<213> ORGANISM: Mus musculus

<400> SEQUENCE: 189

```
gctgcaaaca tccgactgaa ag                                          22
```

<210> SEQ ID NO 190
<211> LENGTH: 24
<212> TYPE: DNA
<213> ORGANISM: Mus musculus

<400> SEQUENCE: 190

```
atccagtcag ttcctgatgc agta                                        24
```

<210> SEQ ID NO 191
<211> LENGTH: 23
<212> TYPE: DNA
<213> ORGANISM: Mus musculus

<400> SEQUENCE: 191

```
gaacaggtag tctaaacact ggg                                         23
```

<210> SEQ ID NO 192
<211> LENGTH: 22
<212> TYPE: DNA
<213> ORGANISM: Mus musculus

<400> SEQUENCE: 192

```
aggcaaagga tgacaaaggg aa                                          22
```

<210> SEQ ID NO 193
<211> LENGTH: 20
<212> TYPE: DNA
<213> ORGANISM: Mus musculus

<400> SEQUENCE: 193

```
agaaaacatg ctccaggtga                                             20
```

<210> SEQ ID NO 194
<211> LENGTH: 23
<212> TYPE: DNA
<213> ORGANISM: Mus musculus

<400> SEQUENCE: 194

```
actggagaca cgtgcactgt aga                                              23

<210> SEQ ID NO 195
<211> LENGTH: 21
<212> TYPE: DNA
<213> ORGANISM: Mus musculus

<400> SEQUENCE: 195
ttaaattaac cgcgaattcg c                                                21

<210> SEQ ID NO 196
<211> LENGTH: 21
<212> TYPE: DNA
<213> ORGANISM: Mus musculus

<400> SEQUENCE: 196
aagacggtgc ttacctgttc c                                                21

<210> SEQ ID NO 197
<211> LENGTH: 22
<212> TYPE: DNA
<213> ORGANISM: Mus musculus

<400> SEQUENCE: 197
acacaaattc ggttctacag gg                                               22

<210> SEQ ID NO 198
<211> LENGTH: 22
<212> TYPE: DNA
<213> ORGANISM: Mus musculus

<400> SEQUENCE: 198
aacaagccca gaccgcaaaa ag                                               22

<210> SEQ ID NO 199
<211> LENGTH: 22
<212> TYPE: DNA
<213> ORGANISM: Mus musculus

<400> SEQUENCE: 199
acccttatca gttctccgtc ca                                               22

<210> SEQ ID NO 200
<211> LENGTH: 18
<212> TYPE: DNA
<213> ORGANISM: Mus musculus

<400> SEQUENCE: 200
gaactgcctt tctctcca                                                    18

<210> SEQ ID NO 201
<211> LENGTH: 23
<212> TYPE: DNA
<213> ORGANISM: Mus musculus

<400> SEQUENCE: 201
aagcccaaaa ggagaattct ttg                                              23

<210> SEQ ID NO 202
<211> LENGTH: 22
<212> TYPE: DNA
<213> ORGANISM: Mus musculus
```

```
<400> SEQUENCE: 202
accctccacc atgcaaggga tg                                     22

<210> SEQ ID NO 203
<211> LENGTH: 23
<212> TYPE: DNA
<213> ORGANISM: Mus musculus

<400> SEQUENCE: 203
actgatgtca gctcagtagg cac                                    23

<210> SEQ ID NO 204
<211> LENGTH: 22
<212> TYPE: DNA
<213> ORGANISM: Mus musculus

<400> SEQUENCE: 204
acctaatata tcaaacatat ca                                     22

<210> SEQ ID NO 205
<211> LENGTH: 22
<212> TYPE: DNA
<213> ORGANISM: Mus musculus

<400> SEQUENCE: 205
agctgctttt gggattccgt tg                                     22

<210> SEQ ID NO 206
<211> LENGTH: 21
<212> TYPE: DNA
<213> ORGANISM: Mus musculus

<400> SEQUENCE: 206
ctgggacttt gtaggccagt t                                      21

<210> SEQ ID NO 207
<211> LENGTH: 22
<212> TYPE: DNA
<213> ORGANISM: Mus musculus

<400> SEQUENCE: 207
tccacatgga gttgctgtta ca                                     22

<210> SEQ ID NO 208
<211> LENGTH: 21
<212> TYPE: DNA
<213> ORGANISM: Mus musculus

<400> SEQUENCE: 208
gccaatattt ctgtgctgct a                                      21

<210> SEQ ID NO 209
<211> LENGTH: 22
<212> TYPE: DNA
<213> ORGANISM: Mus musculus

<400> SEQUENCE: 209
gctgggtgga gaaggtggtg aa                                     22

<210> SEQ ID NO 210
<211> LENGTH: 19
<212> TYPE: DNA
<213> ORGANISM: Mus musculus
```

<400> SEQUENCE: 210
cctatctccc ctctggacc                                                    19

<210> SEQ ID NO 211
<211> LENGTH: 22
<212> TYPE: DNA
<213> ORGANISM: Mus musculus

<400> SEQUENCE: 211
aacaggtagt ctgaacactg gg                                                22

<210> SEQ ID NO 212
<211> LENGTH: 22
<212> TYPE: DNA
<213> ORGANISM: Mus musculus

<400> SEQUENCE: 212
aaccaatgtg cagactactg ta                                                22

<210> SEQ ID NO 213
<211> LENGTH: 21
<212> TYPE: DNA
<213> ORGANISM: Mus musculus

<400> SEQUENCE: 213
catcgttacc agacagtgtt a                                                 21

<210> SEQ ID NO 214
<211> LENGTH: 23
<212> TYPE: DNA
<213> ORGANISM: Mus musculus

<400> SEQUENCE: 214
gtcatcatta ccaggcagta tta                                               23

<210> SEQ ID NO 215
<211> LENGTH: 21
<212> TYPE: DNA
<213> ORGANISM: Mus musculus

<400> SEQUENCE: 215
agaacaatgc cttactgagt a                                                 21

<210> SEQ ID NO 216
<211> LENGTH: 22
<212> TYPE: DNA
<213> ORGANISM: Mus musculus

<400> SEQUENCE: 216
tcttcccatg cgctatacct ct                                                22

<210> SEQ ID NO 217
<211> LENGTH: 22
<212> TYPE: DNA
<213> ORGANISM: Mus musculus

<400> SEQUENCE: 217
ccacacactt ccttacattc ca                                                22

<210> SEQ ID NO 218
<211> LENGTH: 23
<212> TYPE: DNA

```
<213> ORGANISM: Mus musculus

<400> SEQUENCE: 218
gagggaggag agccaggaga agc                                           23

<210> SEQ ID NO 219
<211> LENGTH: 22
<212> TYPE: DNA
<213> ORGANISM: Mus musculus

<400> SEQUENCE: 219
acaagctttt tgctcgtctt at                                            22

<210> SEQ ID NO 220
<211> LENGTH: 20
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n = uracil
<220> FEATURE:
<221> NAME/KEY: misc_feature
<222> LOCATION: (1)..(3)
<223> OTHER INFORMATION: RNA portion of RNA/DNA hybrid
<220> FEATURE:
<221> NAME/KEY: misc_feature
<222> LOCATION: (4)..(20)
<223> OTHER INFORMATION: DNA portion of RNA/DNA hybrid
<220> FEATURE:
<221> NAME/KEY: misc_feature
<222> LOCATION: (20)..(20)
<223> OTHER INFORMATION: n = inverted [3'-3' bond] deoxythymidine

<400> SEQUENCE: 220
nnnaaccgcg aattccagtn                                               20

<210> SEQ ID NO 221
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(15)
<223> OTHER INFORMATION: DNA portion of DNA/RNA hybrid
<220> FEATURE:
<221> NAME/KEY: misc_feature
<222> LOCATION: (16)..(18)
<223> OTHER INFORMATION: RNA portion of DNA/RNA hybrid

<400> SEQUENCE: 221
acggaattcc tcactaaa                                                 18

<210> SEQ ID NO 222
<211> LENGTH: 21
<212> TYPE: DNA
<213> ORGANISM: Artificial Sequence
<220> FEATURE:
<223> OTHER INFORMATION: Probe sequence

<400> SEQUENCE: 222
gcatgcatgc atgcatgcat g                                             21

<210> SEQ ID NO 223
<211> LENGTH: 21
```

```
<212> TYPE: DNA
<213> ORGANISM: Mus musculus

<400> SEQUENCE: 223
gtggtagcgc agtgcgtaga a                                              21

<210> SEQ ID NO 224
<211> LENGTH: 21
<212> TYPE: DNA
<213> ORGANISM: Mus musculus

<400> SEQUENCE: 224
ggtgatgccc tgaatgttgt c                                              21

<210> SEQ ID NO 225
<211> LENGTH: 21
<212> TYPE: DNA
<213> ORGANISM: Mus musculus

<400> SEQUENCE: 225
tgtcatggat gaccttggcc a                                              21

<210> SEQ ID NO 226
<211> LENGTH: 21
<212> TYPE: DNA
<213> ORGANISM: Mus musculus

<400> SEQUENCE: 226
cttttgacat tgaagggagc t                                              21

<210> SEQ ID NO 227
<211> LENGTH: 94
<212> TYPE: DNA
<213> ORGANISM: Mus musculus

<400> SEQUENCE: 227
ttcactgtgg gatgaggtag taggttgtat agttttaggg tcacacccac cactgggaga    60
taactataca atctactgtc tttcctaagg tgat                                94

<210> SEQ ID NO 228
<211> LENGTH: 94
<212> TYPE: DNA
<213> ORGANISM: Rattus norvegicus

<400> SEQUENCE: 228
ttcactgtgg gatgaggtag taggttgtat agttttaggg tcacacccac cactgggaga    60
taactataca atctactgtc tttcctaagg tgat                                94

<210> SEQ ID NO 229
<211> LENGTH: 94
<212> TYPE: DNA
<213> ORGANISM: Mus musculus

<400> SEQUENCE: 229
gcatgttccc aggttgaggt agtaggttgt atagtttaga gttacatcaa gggagataac    60
tgtacagcct cctagctttc cttgggactt gcac                                94

<210> SEQ ID NO 230
<211> LENGTH: 94
<212> TYPE: DNA
<213> ORGANISM: Rattus norvegicus
```

```
<400> SEQUENCE: 230
gcatgctccc aggctgaggt agtaggttgt atagtttaga gttacaacaa gggagataac      60
tgtacagcct cctagctttc cttgggactt gcac                                  94

<210> SEQ ID NO 231
<211> LENGTH: 82
<212> TYPE: DNA
<213> ORGANISM: Mus musculus

<400> SEQUENCE: 231
gggtgaggta gtaggttgtg tggtttcagg gcagtgatgt tgcccctccg aagataacta      60
tacaacctac tgccttccct ga                                               82

<210> SEQ ID NO 232
<211> LENGTH: 82
<212> TYPE: DNA
<213> ORGANISM: Rattus norvegicus

<400> SEQUENCE: 232
gggtgaggta gtaggttgtg tggtttcagg gcagtgatgt cgccctccg aagataacta       60 tacaacctac tgccttccct ga                                               82

<210> SEQ ID NO 233
<211> LENGTH: 94
<212> TYPE: DNA
<213> ORGANISM: Mus musculus

<400> SEQUENCE: 233
tgtgtgcatc cgggttgagg tagtaggttg tatggtttag agttacaccc tgggagttaa      60
ctgtacaacc ttctagcttt ccttggagca cact                                  94

<210> SEQ ID NO 234
<211> LENGTH: 94
<212> TYPE: DNA
<213> ORGANISM: Rattus norvegicus

<400> SEQUENCE: 234
tgtgtgcatc cgggttgagg tagtaggttg tatggtttag agttacaccc tgggagttaa      60
ctgtacaacc ttctagcttt ccttggagca cact                                  94

<210> SEQ ID NO 235
<211> LENGTH: 95
<212> TYPE: DNA
<213> ORGANISM: Mus musculus

<400> SEQUENCE: 235
acggcctttg gggtgaggta gtaggttgta tggttttggg ctctgccccg ctctgcggta      60
actatacaat ctactgtctt tcctgaagtg gccgc                                 95

<210> SEQ ID NO 236
<211> LENGTH: 95
<212> TYPE: DNA
<213> ORGANISM: Rattus norvegicus

<400> SEQUENCE: 236
acggcctttg gggtgaggta gtaggttgta tggttttggg ctctgccccg ctctgcggta      60
actatacaat ctactgtctt tcctgaagtg gccgc                                 95
```

<210> SEQ ID NO 237
<211> LENGTH: 93
<212> TYPE: DNA
<213> ORGANISM: Mus musculus

<400> SEQUENCE: 237 cgcgccccc gggctgaggt aggaggttgt atagttgagg aagacacccg aggagatcac    60
tatacggcct cctagctttc cccaggctgc gcc                                93

<210> SEQ ID NO 238
<211> LENGTH: 93
<212> TYPE: DNA
<213> ORGANISM: Rattus norvegicus

<400> SEQUENCE: 238 cgcgccccc gggctgaggt aggaggttgt atagttgagg aagacacccg aggagatcac    60
tatacggcct cctagctttc cccaggctgc gcc                                93

<210> SEQ ID NO 239
<211> LENGTH: 84
<212> TYPE: DNA
<213> ORGANISM: Mus musculus

<400> SEQUENCE: 239
ctggctgagg tagtagtttg tgctgttggt cgggttgtga cattgcccgc tgtggagata    60
actgcgcaag ctactgcctt gcta                                          84

<210> SEQ ID NO 240
<211> LENGTH: 84
<212> TYPE: DNA
<213> ORGANISM: Rattus norvegicus

<400> SEQUENCE: 240
ctggctgagg tagtagtttg tgctgttggt cgggttgtga cattgcccgc tgtggagata    60
actgcgcaag ctactgcctt gcta                                          84

<210> SEQ ID NO 241
<211> LENGTH: 108
<212> TYPE: DNA
<213> ORGANISM: Mus musculus

<400> SEQUENCE: 241
ttggatgttg gcctagttct gtgtggaaga ctagtgattt tgttgttttt agataactaa    60
aacgacaaca aatcacagtc tgccatatgg cacaggccac ctctacag               108

<210> SEQ ID NO 242
<211> LENGTH: 108
<212> TYPE: DNA
<213> ORGANISM: Rattus norvegicus

<400> SEQUENCE: 242
ttggatgttg gcctagttct gtgtggaaga ctagtgattt tgttgttttt agataactaa    60
gacgacaaca aatcacagtc tgccatatgg cacaggccac ctctacag                108

<210> SEQ ID NO 243
<211> LENGTH: 85
<212> TYPE: DNA
<213> ORGANISM: Mus musculus

<400> SEQUENCE: 243

-continued

```
ccagccccgt ttggaagact agtgattttg ttgttgtgtc tctgtatcca acaacaagtc      60
ccagtctgcc acatggtgct ggtca                                           85
```

<210> SEQ ID NO 244
<211> LENGTH: 83
<212> TYPE: DNA
<213> ORGANISM: Rattus norvegicus

<400> SEQUENCE: 244

```
ccagccctgt ctggaagact agtgattttg ttgttgtgtc tgtgtccaac aacaagtccc      60
agtctgccac atggtgttgg tca                                             83
```

<210> SEQ ID NO 245
<211> LENGTH: 89
<212> TYPE: DNA
<213> ORGANISM: Mus musculus

<400> SEQUENCE: 245

```
cggggttggt tgttatcttt ggttatctag ctgtatgagt ggtgtggagt cttcataaag      60
ctagataacc gaaagtaaaa ataacccca                                       89
```

<210> SEQ ID NO 246
<211> LENGTH: 89
<212> TYPE: DNA
<213> ORGANISM: Rattus norvegicus

<400> SEQUENCE: 246

```
cggggttggt tgttatcttt ggttatctag ctgtatgagt ggtgtggagt cttcataaag      60
ctagataacc gaaagtaaaa ataacccca                                       89
```

<210> SEQ ID NO 247
<211> LENGTH: 88
<212> TYPE: DNA
<213> ORGANISM: Mus musculus

<400> SEQUENCE: 247

```
ggaggcccgt ttctctcttt ggttatctag ctgtatgagt gccacagagc cgtcataaag      60
ctagataacc gaaagtagaa atgactct                                        88
```

<210> SEQ ID NO 248
<211> LENGTH: 88
<212> TYPE: DNA
<213> ORGANISM: Rattus norvegicus

<400> SEQUENCE: 248

```
ggaggcccgt ttctctcttt ggttatctag ctgtatgagt gccacagagc cgtcataaag      60
ctagataacc gaaagtagaa atgactct                                        88
```

<210> SEQ ID NO 249
<211> LENGTH: 72
<212> TYPE: DNA
<213> ORGANISM: Mus musculus

<400> SEQUENCE: 249

```
gttgttatct ttggttatct agctgtatga gtgtattggt cttcataaag ctagataacc      60
gaaagtaaaa ac                                                         72
```

<210> SEQ ID NO 250
<211> LENGTH: 72

```
<212> TYPE: DNA
<213> ORGANISM: Rattus norvegicus

<400> SEQUENCE: 250
gttgttatct ttggttatct agctgtatga gtgtattggt cttcataaag ctagataacc    60
gaaagtaaaa ac                                                        72

<210> SEQ ID NO 251
<211> LENGTH: 91
<212> TYPE: DNA
<213> ORGANISM: Mus musculus

<400> SEQUENCE: 251
cttgttccac tctagcagca cgtaaatatt ggcgtagtga aataaatatt aaacaccaat    60
attattgtgc tgctttagtg tgacagggat a                                   91

<210> SEQ ID NO 252
<211> LENGTH: 91
<212> TYPE: DNA
<213> ORGANISM: Rattus norvegicus

<400> SEQUENCE: 252
cttgttccgc tctagcagca cgtaaatatt ggcgtagtga aataaatatt aaacaccaat    60
attattgtgc tgctttagtg tgacagggat a                                   91

<210> SEQ ID NO 253
<211> LENGTH: 68
<212> TYPE: DNA
<213> ORGANISM: Mus musculus

<400> SEQUENCE: 253
ctccggtgcc tactgagctg atatcagttc tcatttcaca cactggctca gttcagcagg    60
aacaggag                                                             68

<210> SEQ ID NO 254
<211> LENGTH: 68
<212> TYPE: DNA
<213> ORGANISM: Rattus norvegicus

<400> SEQUENCE: 254
ctccggtgcc tactgagctg atatcagttc tcatttcaca cactggctca gttcagcagg    60
aacaggag                                                             68

<210> SEQ ID NO 255
<211> LENGTH: 107
<212> TYPE: DNA
<213> ORGANISM: Mus musculus

<400> SEQUENCE: 255
gcctctctcc gggctccgcc tcccgtgcct actgagctga aacagttgat tccagtgcac    60
tggctcagtt cagcaggaac aggagtccag cccctagga gctggca                  107

<210> SEQ ID NO 256
<211> LENGTH: 108
<212> TYPE: DNA
<213> ORGANISM: Rattus norvegicus

<400> SEQUENCE: 256
gcctctccct gggctccgcc tcctgtgcct actgagctga aacagttgat tccagtgcac    60
```

-continued tggctcagtt cagcaggaac aggagtccag cccccatagg agctggca    108

<210> SEQ ID NO 257
<211> LENGTH: 85
<212> TYPE: DNA
<213> ORGANISM: Mus musculus

<400> SEQUENCE: 257
tgcccgggac ccagttcaag taattcagga taggttgtgg tgctgaccag cctgttctcc    60
attacttggc tcggggccg gtgcc    85

<210> SEQ ID NO 258
<211> LENGTH: 85
<212> TYPE: DNA
<213> ORGANISM: Rattus norvegicus

<400> SEQUENCE: 258
tgcccgggac ccagttcaag taattcagga taggttgtgg tgctggccag cctgttctcc    60
attacttggc tcggggccg gtgcc    85

<210> SEQ ID NO 259
<211> LENGTH: 86
<212> TYPE: DNA
<213> ORGANISM: Mus musculus

<400> SEQUENCE: 259
ggtccctacc ttcaaggagc tcacagtcta ttgagttgcc tttctgattc tcccactaga    60
ttgtgagctg ctggagggca ggcact    86

<210> SEQ ID NO 260
<211> LENGTH: 86
<212> TYPE: DNA
<213> ORGANISM: Rattus norvegicus

<400> SEQUENCE: 260
ggtccctacc cgcaaggagc tcacagtcta ttgagttcct tttctgattc tcccactaga    60
ttgtgagctc ctggagggca ggcact    86

<210> SEQ ID NO 261
<211> LENGTH: 88
<212> TYPE: DNA
<213> ORGANISM: Mus musculus

<400> SEQUENCE: 261 acccccttaga ggatgactga tttcttttgg tgttcagagt caatagaatt ttctagcacc    60
atctgaaatc ggttataatg attgggga    88

<210> SEQ ID NO 262
<211> LENGTH: 88
<212> TYPE: DNA
<213> ORGANISM: Rattus norvegicus

<400> SEQUENCE: 262 acccccttaga ggatgactga tttcttttgg tgttcagagt caatagaatt ttctagcacc    60
atctgaaatc ggttataatg attgggga    88

<210> SEQ ID NO 263
<211> LENGTH: 88
<212> TYPE: DNA
<213> ORGANISM: Mus musculus

<400> SEQUENCE: 263
atctcttaca caggctgacc gatttctcct ggtgttcaga gtctgttttt gtctagcacc    60
atttgaaatc ggttatgatg taggggga                                      88

<210> SEQ ID NO 264
<211> LENGTH: 88
<212> TYPE: DNA
<213> ORGANISM: Rattus norvegicus

<400> SEQUENCE: 264
atctcttaca caggctgacc gatttctcct ggtgttcaga gtctgttttt gtctagcacc    60
atttgaaatc ggttatgatg taggggga                                      88

<210> SEQ ID NO 265
<211> LENGTH: 71
<212> TYPE: DNA
<213> ORGANISM: Mus musculus

<400> SEQUENCE: 265
aggaagctgg tttcatatgg tggtttagat ttaaatagtg attgtctagc accatttgaa    60
atcagtgttc t                                                        71

<210> SEQ ID NO 266
<211> LENGTH: 71
<212> TYPE: DNA
<213> ORGANISM: Rattus norvegicus

<400> SEQUENCE: 266
aggaagctgg tttcatatgg tggtttagat ttaaatagtg attgtctagc accatttgaa    60
atcagtgttc t                                                        71

<210> SEQ ID NO 267
<211> LENGTH: 81
<212> TYPE: DNA
<213> ORGANISM: Mus musculus

<400> SEQUENCE: 267
cttctggaag ctggtttcac atggtggctt agattttttcc atctttgtat ctagcaccat    60
ttgaaatcag tgttttagga g                                             81

<210> SEQ ID NO 268
<211> LENGTH: 81
<212> TYPE: DNA
<213> ORGANISM: Rattus norvegicus

<400> SEQUENCE: 268
cttctggaag ctggtttcac atggtggctt agattttttcc atctttgtat ctagcaccat    60
ttgaaatcag tgttttagga g                                             81

<210> SEQ ID NO 269
<211> LENGTH: 60
<212> TYPE: DNA
<213> ORGANISM: Mus musculus

<400> SEQUENCE: 269
atgtaaacat cctacactca gctgtcatac atgcgttggc tgggatgtgg atgtttacgt    60

<210> SEQ ID NO 270

```
<211> LENGTH: 60
<212> TYPE: DNA
<213> ORGANISM: Rattus norvegicus

<400> SEQUENCE: 270
atgtaaacat cctacactca gctgtcatac atgagttggc tgggatgtgg atgtttacgt      60

<210> SEQ ID NO 271
<211> LENGTH: 89
<212> TYPE: DNA
<213> ORGANISM: Mus musculus

<400> SEQUENCE: 271
accatgttgt agtgtgtgta aacatcctac actctcagct gtgagctcaa ggtggctggg      60
agagggttgt ttactccttc tgccatgga                                        89

<210> SEQ ID NO 272
<211> LENGTH: 89
<212> TYPE: DNA
<213> ORGANISM: Rattus norvegicus

<400> SEQUENCE: 272
accatgttgt agtgtgtgta aacatcctac actctcagct gtgagctcaa ggtggctggg      60
agagggttgt ttactccttc tgccatgga                                        89

<210> SEQ ID NO 273
<211> LENGTH: 84
<212> TYPE: DNA
<213> ORGANISM: Mus musculus

<400> SEQUENCE: 273
gagtgacaga tattgtaaac atcctacact ctcagctgtg aaaagtaaga aagctgggag      60
aaggctgttt actctctctg cctt                                             84

<210> SEQ ID NO 274
<211> LENGTH: 84
<212> TYPE: DNA
<213> ORGANISM: Rattus norvegicus

<400> SEQUENCE: 274
gagtgacaga tactgtaaac atcctacact ctcagctgtg aaaagtaaga aagctgggag      60
aaggctgttt actctctctg cctt                                             84

<210> SEQ ID NO 275
<211> LENGTH: 84
<212> TYPE: DNA
<213> ORGANISM: Mus musculus

<400> SEQUENCE: 275
tgcccattca tccacaggtg gggattggtg gcattacttg tgttagatat aaagtattgc      60
acttgtcccg gcctgaggaa gaaa                                             84

<210> SEQ ID NO 276
<211> LENGTH: 84
<212> TYPE: DNA
<213> ORGANISM: Rattus norvegicus

<400> SEQUENCE: 276
tgcccattca tccacaggtg gggattagtg ccattacttg tgttagataa aaagtattgc      60
acttgtcccg gcctgaggaa gaaa                                             84
```

<210> SEQ ID NO 277
<211> LENGTH: 88
<212> TYPE: DNA
<213> ORGANISM: Mus musculus

<400> SEQUENCE: 277
agtcatgggg gctccaaagt gctgttcgtg caggtagtgt aattacctga cctactgctg    60
agctagcact tcccgagccc ccaggaca    88

<210> SEQ ID NO 278
<211> LENGTH: 87
<212> TYPE: DNA
<213> ORGANISM: Rattus norvegicus

<400> SEQUENCE: 278
agtcatgggg gctccaaagt gctgttcgtg caggtagtgc attgcctgac ctactgctga    60
gctagcactt cccgagcccc caggaca    87

<210> SEQ ID NO 279
<211> LENGTH: 65
<212> TYPE: DNA
<213> ORGANISM: Mus musculus

<400> SEQUENCE: 279
cataaacccg tagatccgat cttgtggtga agtggaccgc gcaagctcgt ttctatgggt    60
ctgtg    65

<210> SEQ ID NO 280
<211> LENGTH: 65
<212> TYPE: DNA
<213> ORGANISM: Rattus norvegicus

<400> SEQUENCE: 280
cataaacccg tagatccgat cttgtggtga agtggaccgc acaagctcgt ttctatgggt    60
ctgtg    65

<210> SEQ ID NO 281
<211> LENGTH: 70
<212> TYPE: DNA
<213> ORGANISM: Mus musculus

<400> SEQUENCE: 281
ggcacccacc cgtagaaccg accttgcggg gccttcgccg cacacaagct cgtgtctgtg    60
ggtccgtgtc    70

<210> SEQ ID NO 282
<211> LENGTH: 70
<212> TYPE: DNA
<213> ORGANISM: Rattus norvegicus

<400> SEQUENCE: 282
ggcacccacc cgtagaaccg accttgcggg gccttcgccg cacacaagct cgtgtctgtg    60
ggtccgtgtc    70

<210> SEQ ID NO 283
<211> LENGTH: 86
<212> TYPE: DNA
<213> ORGANISM: Mus musculus

```
<400> SEQUENCE: 283
ttcttactgc cctcggcttc tttacagtgc tgccttgttg catatggatc aagcagcatt      60
gtacagggct atgaaggcat tgagac                                          86

<210> SEQ ID NO 284
<211> LENGTH: 86
<212> TYPE: DNA
<213> ORGANISM: Rattus norvegicus

<400> SEQUENCE: 284
ttcttactgc cctcggcttc tttacagtgc tgccttgttg catatggatc aagcagcatt      60
gtacagggct atgaaggcat tgagac                                          86

<210> SEQ ID NO 285
<211> LENGTH: 86
<212> TYPE: DNA
<213> ORGANISM: Mus musculus

<400> SEQUENCE: 285
gtcttcgtgc tttcagcttc tttacagtgc tgccttgtag cattcaggtc aagcagcatt      60
gtacagggct atgaaagaac caagaa                                          86

<210> SEQ ID NO 286
<211> LENGTH: 86
<212> TYPE: DNA
<213> ORGANISM: Rattus norvegicus

<400> SEQUENCE: 286
gtcttcgtgc tttcagcttc tttacagtgc tgccttgtag cattcaggtc aagcagcatt      60
gtacagggct atgaaagaac caagaa                                          86

<210> SEQ ID NO 287
<211> LENGTH: 85
<212> TYPE: DNA
<213> ORGANISM: Mus musculus

<400> SEQUENCE: 287
aggcctctct ctccgtgttc acagcggacc ttgatttaaa tgtccataca attaaggcac      60
gcggtgaatg ccaagaatgg ggctg                                           85

<210> SEQ ID NO 288
<211> LENGTH: 85
<212> TYPE: DNA
<213> ORGANISM: Rattus norvegicus

<400> SEQUENCE: 288
aggcctctct ctccgtgttc acagcggacc ttgatttaaa tgtccataca attaaggcac      60
gcggtgaatg ccaagaatgg ggctg                                           85

<210> SEQ ID NO 289
<211> LENGTH: 109
<212> TYPE: DNA
<213> ORGANISM: Mus musculus

<400> SEQUENCE: 289
atcaagatca gagactctgc tctccgtgtt cacagcggac cttgatttaa tgtcatacaa      60
ttaaggcacg cggtgaatgc caagagcgga gcctacggct gcacttgaa                109
```

<210> SEQ ID NO 290
<211> LENGTH: 109
<212> TYPE: DNA
<213> ORGANISM: Rattus norvegicus

<400> SEQUENCE: 290
atcaagatca gagactctgc tctccgtgtt cacagcggac cttgatttaa tgtcatacaa    60
ttaaggcacg cggtgaatgc caagagcgga gcctacggct gcacttgaa              109

<210> SEQ ID NO 291
<211> LENGTH: 68
<212> TYPE: DNA
<213> ORGANISM: Mus musculus

<400> SEQUENCE: 291
ctctgcgtgt tcacagcgga ccttgattta atgtctatac aattaaggca cgcggtgaat    60
gccaagag                                                             68

<210> SEQ ID NO 292
<211> LENGTH: 68
<212> TYPE: DNA
<213> ORGANISM: Rattus norvegicus

<400> SEQUENCE: 292
ctctgcgtgt tcacagcgga ccttgattta atgtctatac aattaaggca cgcggtgaat    60
gccaagag                                                             68

<210> SEQ ID NO 293
<211> LENGTH: 68
<212> TYPE: DNA
<213> ORGANISM: Mus musculus

<400> SEQUENCE: 293
ctgggtccct gagacccttt aacctgtgag gacgtccagg gtcacaggtg aggttcttgg    60
gagcctgg                                                             68

<210> SEQ ID NO 294
<211> LENGTH: 68
<212> TYPE: DNA
<213> ORGANISM: Rattus norvegicus

<400> SEQUENCE: 294
ctgggtccct gagacccttt aacctgtgag gacgtccagg gtcacaggtg aggttcttgg    60
gagcctgg                                                             68

<210> SEQ ID NO 295
<211> LENGTH: 70
<212> TYPE: DNA
<213> ORGANISM: Mus musculus

<400> SEQUENCE: 295
cctagtccct gagaccctaa cttgtgaggt attttagtaa catcacaagt caggttcttg    60
ggacctaggc                                                           70

<210> SEQ ID NO 296
<211> LENGTH: 70
<212> TYPE: DNA
<213> ORGANISM: Rattus norvegicus

<400> SEQUENCE: 296

```
cctagtccct gagaccctaa cttgtgaggt attttagtaa catcacaagt caggctcttg    60
ggacctaggc                                                           70
```

<210> SEQ ID NO 297
<211> LENGTH: 77
<212> TYPE: DNA
<213> ORGANISM: Mus musculus

<400> SEQUENCE: 297

```
tgcgctcccc tcagtccctg agaccctaac ttgtgatgtt taccgtttaa atccacgggt    60
taggctcttg ggagctg                                                   77
```

<210> SEQ ID NO 298
<211> LENGTH: 77
<212> TYPE: DNA
<213> ORGANISM: Rattus norvegicus

<400> SEQUENCE: 298

```
tgcgctcccc tcagtccctg agaccctaac ttgtgatgtt taccgtttaa atccacgggt    60
taggctcttg ggagctg                                                   77
```

<210> SEQ ID NO 299
<211> LENGTH: 70
<212> TYPE: DNA
<213> ORGANISM: Mus musculus

<400> SEQUENCE: 299

```
ccagcctgct gaagctcaga gggctctgat tcagaaagat catcggatcc gtctgagctt    60
ggctggtcgg                                                           70
```

<210> SEQ ID NO 300
<211> LENGTH: 70
<212> TYPE: DNA
<213> ORGANISM: Rattus norvegicus

<400> SEQUENCE: 300

```
ccagcctgct gaagctcaga gggctctgat tcagaaagat catcggatcc gtctgagctt    60
ggctggtcgg                                                           70
```

<210> SEQ ID NO 301
<211> LENGTH: 70
<212> TYPE: DNA
<213> ORGANISM: Mus musculus

<400> SEQUENCE: 301

```
gttggattcg gggccgtagc actgtctgag aggtttacat ttctcacagt gaaccggtct    60 cttttttcagc                                                          70
```

<210> SEQ ID NO 302
<211> LENGTH: 70
<212> TYPE: DNA
<213> ORGANISM: Rattus norvegicus

<400> SEQUENCE: 302

```
gttggattcg gggccgtagc actgtctgag aggtttacat ttctcacagt gaaccggtct    60 cttttttcagc                                                          70
```

<210> SEQ ID NO 303
<211> LENGTH: 76

```
<212> TYPE: DNA
<213> ORGANISM: Mus musculus

<400> SEQUENCE: 303
cagtgggaag gggggccgat gcactgtaag agagtgagta gcaggtctca cagtgaaccg    60
gtctctttcc ctactg                                                   76

<210> SEQ ID NO 304
<211> LENGTH: 76
<212> TYPE: DNA
<213> ORGANISM: Rattus norvegicus

<400> SEQUENCE: 304
cagtgggaag gggggccgat gcactgtaag agagtgagta gcaggtctca cagtgaaccg    60
gtctctttcc ctactg                                                   76

<210> SEQ ID NO 305
<211> LENGTH: 64
<212> TYPE: DNA
<213> ORGANISM: Mus musculus

<400> SEQUENCE: 305
gagctctttt cacattgtgc tactgtctaa cgtgtaccga gcagtgcaat gttaaaaggg    60
catc                                                                64

<210> SEQ ID NO 306
<211> LENGTH: 65
<212> TYPE: DNA
<213> ORGANISM: Rattus norvegicus

<400> SEQUENCE: 306
gagctctttt cacattgtgc tactgtctac acgtgtaccg agcagtgcaa tgttaaaagg    60
gcatc                                                               65

<210> SEQ ID NO 307
<211> LENGTH: 66
<212> TYPE: DNA
<213> ORGANISM: Mus musculus

<400> SEQUENCE: 307
gggcaaccgt ggctttcgat tgttactgtg ggaaccggag gtaacagtct acagccatgg    60
tcgccc                                                              66

<210> SEQ ID NO 308
<211> LENGTH: 66
<212> TYPE: DNA
<213> ORGANISM: Rattus norvegicus

<400> SEQUENCE: 308
gggcaaccgt ggctttcgat tgttactgtg ggaaccggag gtaacagtct acagccatgg    60
tcgccc                                                              66

<210> SEQ ID NO 309
<211> LENGTH: 62
<212> TYPE: DNA
<213> ORGANISM: Mus musculus

<400> SEQUENCE: 309
gaggactcca tttgttttga tgatggattc ttaagctcca tcatcgtctc aaatgagtct    60
```

-continued

```
tc                                                              62

<210> SEQ ID NO 310
<211> LENGTH: 62
<212> TYPE: DNA
<213> ORGANISM: Rattus norvegicus

<400> SEQUENCE: 310
gaggactcca tttgttttga tgatggattc ttaagctcca tcatcgtctc aaatgagtct    60
tc                                                              62

<210> SEQ ID NO 311
<211> LENGTH: 97
<212> TYPE: DNA
<213> ORGANISM: Mus musculus

<400> SEQUENCE: 311
ctctagcatg gtgttgtggg acagctggtg ttgtgaatca ggccgttgcc aatcagagaa    60
cggctacttc acaacaccag ggccacactg cactgca                           97

<210> SEQ ID NO 312
<211> LENGTH: 97
<212> TYPE: DNA
<213> ORGANISM: Rattus norvegicus

<400> SEQUENCE: 312
ctctggcatg gtgttgtggg acagctggtg ttgtgaatca ggccgttgcc aatcagagaa    60
cggctacttc acaacaccag ggtctcactg cactgca                           97

<210> SEQ ID NO 313
<211> LENGTH: 71
<212> TYPE: DNA
<213> ORGANISM: Mus musculus

<400> SEQUENCE: 313
cagctggtgt tgtgaatcag gccgacgagc agcgcatcct cttacccggc tatttcacga    60
caccagggtt g                                                   71

<210> SEQ ID NO 314
<211> LENGTH: 71
<212> TYPE: DNA
<213> ORGANISM: Rattus norvegicus

<400> SEQUENCE: 314
cagctggtgt tgtgaatcag gccgacgagc aacgcatcct cttacccggc tatttcacga    60
caccagggtt g                                                   71

<210> SEQ ID NO 315
<211> LENGTH: 68
<212> TYPE: DNA
<213> ORGANISM: Mus musculus

<400> SEQUENCE: 315
gtgtattcta cagtgcacgt gtctccagtg tggctcggag gctggagacg cggccctgtt    60
ggagtaac                                                      68

<210> SEQ ID NO 316
<211> LENGTH: 68
<212> TYPE: DNA
<213> ORGANISM: Rattus norvegicus
```

<400> SEQUENCE: 316
gtgtattcta cagtgcacgt gtctccagtg tggctcggag gctggagacg cggccctgtt    60
ggagtaac    68

<210> SEQ ID NO 317
<211> LENGTH: 64
<212> TYPE: DNA
<213> ORGANISM: Mus musculus

<400> SEQUENCE: 317
acccataaag tagaaagcac tactaacagc actggagggt gtagtgtttc ctactttatg    60
gatg    64

<210> SEQ ID NO 318
<211> LENGTH: 64
<212> TYPE: DNA
<213> ORGANISM: Rattus norvegicus

<400> SEQUENCE: 318
acccataaag tagaaagcac tactaacagc actggagggt gtagtgtttc ctactttatg    60
gatg    64

<210> SEQ ID NO 319
<211> LENGTH: 70
<212> TYPE: DNA
<213> ORGANISM: Mus musculus

<400> SEQUENCE: 319
ctcacggtcc agttttccca ggaatcccct ggatgctaag atggggattc ctggaaatac    60
tgttcttgag    70

<210> SEQ ID NO 320
<211> LENGTH: 70
<212> TYPE: DNA
<213> ORGANISM: Rattus norvegicus

<400> SEQUENCE: 320
ctcacggtcc agttttccca ggaatcccct ggatgctaag atggggattc ctggaaatac    60
tgttcttgag    70

<210> SEQ ID NO 321
<211> LENGTH: 65
<212> TYPE: DNA
<213> ORGANISM: Mus musculus

<400> SEQUENCE: 321
agctctgaga actgaattcc atgggttata tcaatgtcag acctgtgaaa ttcagttctt    60
cagct    65

<210> SEQ ID NO 322
<211> LENGTH: 65
<212> TYPE: DNA
<213> ORGANISM: Rattus norvegicus

<400> SEQUENCE: 322
agctctgaga actgaattcc atgggttata gcaatgtcag acctgtgaag ttcagttctt    60
tagct    65

<210> SEQ ID NO 323
<211> LENGTH: 65
<212> TYPE: DNA
<213> ORGANISM: Mus musculus

<400> SEQUENCE: 323
ccctgtctcc caaccttgt accagtgctg tgcctcagac cctggtacag gcctggggga    60
taggg                                                              65

<210> SEQ ID NO 324
<211> LENGTH: 65
<212> TYPE: DNA
<213> ORGANISM: Rattus norvegicus

<400> SEQUENCE: 324
ccctgtctcc caaccttgt accagtgctg tgcctcagac cctggtacag gcctggggga    60
caggg                                                              65

<210> SEQ ID NO 325
<211> LENGTH: 66
<212> TYPE: DNA
<213> ORGANISM: Mus musculus

<400> SEQUENCE: 325
gaagataggt tatccgtgtt gccttcgctt tattcgtgac gaatcataca cggttgacct    60
attttt                                                             66

<210> SEQ ID NO 326
<211> LENGTH: 66
<212> TYPE: DNA
<213> ORGANISM: Rattus norvegicus

<400> SEQUENCE: 326
gaagataggt tatccgtgtt gccttcgctt tattcgtgac gaatcataca cggttgacct    60
attttt                                                             66

<210> SEQ ID NO 327
<211> LENGTH: 65
<212> TYPE: DNA
<213> ORGANISM: Mus musculus

<400> SEQUENCE: 327
agggattgga gagaaaggca gttcctgatg gtccctccc aggggctggc tttcctctgg     60
tcctt                                                              65

<210> SEQ ID NO 328
<211> LENGTH: 65
<212> TYPE: DNA
<213> ORGANISM: Rattus norvegicus

<400> SEQUENCE: 328
agggattgga gagaaaggca gttcctgatg gtccctccc aggggctggc tttcctctgg     60
tcctt                                                              65

<210> SEQ ID NO 329
<211> LENGTH: 74
<212> TYPE: DNA
<213> ORGANISM: Mus musculus

<400> SEQUENCE: 329

```
agcgggcaac ggaatcccaa aagcagctgt tgtctccaga gcattccagc tgcacttgga    60
tttcgttccc tgct                                                      74

<210> SEQ ID NO 330
<211> LENGTH: 74
<212> TYPE: DNA
<213> ORGANISM: Rattus norvegicus

<400> SEQUENCE: 330
agcgggcaac ggaatcccaa aagcagctgt tgtctccaga gcattccagc tgcacttgga    60
tttcgttccc tgct                                                      74

<210> SEQ ID NO 331
<211> LENGTH: 87
<212> TYPE: DNA
<213> ORGANISM: Mus musculus

<400> SEQUENCE: 331
ggttgcttca gtgaacattc aacgctgtcg gtgagtttgg aattcaaata aaaaccatcg    60
accgttgatt gtaccctata gctaacc                                        87

<210> SEQ ID NO 332
<211> LENGTH: 87
<212> TYPE: DNA
<213> ORGANISM: Rattus norvegicus

<400> SEQUENCE: 332
ggttgcttca gtgaacattc aacgctgtcg gtgagtttgg aattcaaata aaaaccatcg    60
accgttgatt gtaccctata gctaacc                                        87

<210> SEQ ID NO 333
<211> LENGTH: 79
<212> TYPE: DNA
<213> ORGANISM: Mus musculus

<400> SEQUENCE: 333
gctacttgaa gagaggttat cctttgtgtg tttgctttac gcgaaatgaa tatgcaaggg    60
caagctctct tcgaggagc                                                 79

<210> SEQ ID NO 334
<211> LENGTH: 79
<212> TYPE: DNA
<213> ORGANISM: Rattus norvegicus

<400> SEQUENCE: 334
gctacttgaa gagaggttat cctttgtgtg tttgctttac gcgaaatgaa tatgcaaggg    60
caagctctct tcgaggagc                                                 79

<210> SEQ ID NO 335
<211> LENGTH: 94
<212> TYPE: RNA
<213> ORGANISM: Rattus norvegicus

<400> SEQUENCE: 335
gcaugcuccc aggcugaggu aguagguugu auaguuuaga guuacaacaa gggagauaac    60
uguacagccu ccuagcuuuc cuugggacuu gcac                                94

<210> SEQ ID NO 336
```

```
<211> LENGTH: 82
<212> TYPE: RNA
<213> ORGANISM: Rattus norvegicus

<400> SEQUENCE: 336
gggugaggua guagguugug ugguuucagg gcagugaugu cgccccuccg aagauaacua    60
uacaaccuac ugccuucccu ga                                             82

<210> SEQ ID NO 337
<211> LENGTH: 108
<212> TYPE: RNA
<213> ORGANISM: Rattus norvegicus

<400> SEQUENCE: 337
uuggauguug gccuaguucu guguggaaga cuagugauuu uguuguuuuu agauaacuaa    60
gacgacaaca aaucacaguc ugccauaugg cacaggccac cucuacag               108

<210> SEQ ID NO 338
<211> LENGTH: 83
<212> TYPE: RNA
<213> ORGANISM: Rattus norvegicus

<400> SEQUENCE: 338
ccagcccugu cuggaagacu agugauuuug uuguugguc uguccaac aacaagucc        60 agucugccac augguguugg uca                                            83

<210> SEQ ID NO 339
<211> LENGTH: 91
<212> TYPE: RNA
<213> ORGANISM: Rattus norvegicus

<400> SEQUENCE: 339
cuuguuccgc ucuagcagca cguaaauauu ggcguaguga aauaaauauu aaacaccaau    60
auuauugugc ugcuuuagug ugacagggau a                                   91

<210> SEQ ID NO 340
<211> LENGTH: 108
<212> TYPE: RNA
<213> ORGANISM: Rattus norvegicus

<400> SEQUENCE: 340
gcccucuccu gggcuccgcc uccugugccu acugagcuga aacaguugau uccagugcac    60
uggcucaguu cagcaggaac aggaguccag ccccauagg agcuggca                108

<210> SEQ ID NO 341
<211> LENGTH: 85
<212> TYPE: RNA
<213> ORGANISM: Rattus norvegicus

<400> SEQUENCE: 341
ugcccgggac ccaguucaag uaauucagga uagguugugg ugcuggccag ccuguucucc    60
auuacuuggc ucgggggccg gugcc                                          85

<210> SEQ ID NO 342
<211> LENGTH: 86
<212> TYPE: RNA
<213> ORGANISM: Rattus norgevicus

<400> SEQUENCE: 342
ggucccuacc cgcaaggagc ucacagucua uugaguuccu uuucugauuc ucccacuaga    60
```

```
uugugagcuc cuggagggca ggcacu                                   86

<210> SEQ ID NO 343
<211> LENGTH: 60
<212> TYPE: RNA
<213> ORGANISM: Rattus norgevicus

<400> SEQUENCE: 343
auguaaacau ccuacacuca gcugucauac augaguuggc ugggaugugg auguuuacgu   60

<210> SEQ ID NO 344
<211> LENGTH: 84
<212> TYPE: RNA
<213> ORGANISM: Rattus norgevicus

<400> SEQUENCE: 344
gagugacaga uacuguaaac auccuacacu cucagcugug aaaaguaaga aagcugggag   60
aaggcuguuu acucucucug ccuu                                         84

<210> SEQ ID NO 345
<211> LENGTH: 84
<212> TYPE: RNA
<213> ORGANISM: Rattus norgevicus

<400> SEQUENCE: 345
ugcccauuca uccacaggug gggauuagug ccauuacuug uguuagauaa aaaguauugc   60
acuugucccg gccugaggaa gaaa                                         84

<210> SEQ ID NO 346
<211> LENGTH: 87
<212> TYPE: RNA
<213> ORGANISM: Rattus norgevicus

<400> SEQUENCE: 346
agucaugggg gcuccaaagu gcuguucgug cagguagugc auugccugac cuacugcuga   60
gcuagcacuu cccgagcccc caggaca                                      87

<210> SEQ ID NO 347
<211> LENGTH: 65
<212> TYPE: RNA
<213> ORGANISM: Rattus norgevicus

<400> SEQUENCE: 347
cauaaacccg uagauccgau cuuguggugu agguggaccgc acaagcucgu uucuaugggu   60
cugug                                                              65

<210> SEQ ID NO 348
<211> LENGTH: 70
<212> TYPE: RNA
<213> ORGANISM: Rattus norgevicus

<400> SEQUENCE: 348
ccuagucccu gagacccuaa cuugugaggu auuuuaguaa caucacaagu caggcucuug   60
ggaccuaggc                                                         70

<210> SEQ ID NO 349
<211> LENGTH: 65
<212> TYPE: RNA
<213> ORGANISM: Rattus norgevicus
```

```
<400> SEQUENCE: 349
gagcucuuuu cacauugugc uacugucuac acguguaccg agcagugcaa uguuaaaagg      60
gcauc                                                                 65

<210> SEQ ID NO 350
<211> LENGTH: 97
<212> TYPE: RNA
<213> ORGANISM: Rattus norgevicus

<400> SEQUENCE: 350
cucuggcaug guguugugg acagcuggug uugugaauca ggccguugcc aaucagagaa       60
cggcuacuuc acaacaccag ggucucacug cacugca                              97

<210> SEQ ID NO 351
<211> LENGTH: 71
<212> TYPE: RNA
<213> ORGANISM: Rattus norgevicus

<400> SEQUENCE: 351
cagcuggugu ugugaaucag gccgacgagc aacgcauccu cuuacccggc uauuucacga     60
caccaggguu g                                                         71

<210> SEQ ID NO 352
<211> LENGTH: 65
<212> TYPE: RNA
<213> ORGANISM: Rattus norgevicus

<400> SEQUENCE: 352
agcucugaga acugaauucc auggguuaua gcaaugucag accugugaag uucaguucuu     60
uagcu                                                                65

<210> SEQ ID NO 353
<211> LENGTH: 79
<212> TYPE: RNA
<213> ORGANISM: Rattus norgevicus

<400> SEQUENCE: 353
cacacuguag gccucauuaa auguuuguug aaugaaaaaa ugaaucauca acagacauua     60
auugggcgcc ugcucugug                                                 79

<210> SEQ ID NO 354
<211> LENGTH: 79
<212> TYPE: DNA
<213> ORGANISM: Rattus norgevicus

<400> SEQUENCE: 354
cacactgtag gcctcattaa atgtttgttg aatgaaaaaa tgaatcatca acagacatta     60
attgggcgcc tgctctgtg                                                 79

<210> SEQ ID NO 355
<211> LENGTH: 79
<212> TYPE: DNA
<213> ORGANISM: Homo sapiens

<400> SEQUENCE: 355
cacattgtag gcctcattaa atgtttgttg aatgaaaaaa tgaatcatca acagacatta     60
attgggcgcc tgctctgtg                                                 79
```

```
<210> SEQ ID NO 356
<211> LENGTH: 79
<212> TYPE: DNA
<213> ORGANISM: Mus musculus

<400> SEQUENCE: 356
cacattgtag gcctcattaa atgtttgttg aatgaaaaaa tgaatcatca acagacatta      60
attgggcgcc tgctctgtg                                                  79

<210> SEQ ID NO 357
<211> LENGTH: 79
<212> TYPE: RNA
<213> ORGANISM: Mus musculus

<400> SEQUENCE: 357
cacauuguag gccucauuaa auguuuguug aaugaaaaaa ugaaucauca acagacauua      60
auugggcgcc ugcucugug                                                  79

<210> SEQ ID NO 358
<211> LENGTH: 79
<212> TYPE: RNA
<213> ORGANISM: Homo sapiens

<400> SEQUENCE: 358
cacauuguag gccucauuaa auguuuguug aaugaaaaaa ugaaucauca acagacauua      60
auugggcgcc ugcucugug                                                  79

<210> SEQ ID NO 359
<211> LENGTH: 87
<212> TYPE: RNA
<213> ORGANISM: Macaca mulatta

<400> SEQUENCE: 359
gcgguacuua uacagcagua uaugugcggg ugaugccgag guugugaguu cgagccucac      60
cuggagcaug uuuucuuccc uuccgc                                          87

<210> SEQ ID NO 360
<211> LENGTH: 23
<212> TYPE: DNA
<213> ORGANISM: Mus musculus

<400> SEQUENCE: 360
gtggtaatcc ctggcaatgt gat                                             23

<210> SEQ ID NO 361
<211> LENGTH: 18
<212> TYPE: DNA
<213> ORGANISM: Mus musculus

<400> SEQUENCE: 361
agacacgtgc actgtaga                                                   18

<210> SEQ ID NO 362
<211> LENGTH: 23
<212> TYPE: DNA
<213> ORGANISM: Mus musculus

<400> SEQUENCE: 362
aacactgatt tcaaatggtg cta                                             23

<210> SEQ ID NO 363
```

```
<211> LENGTH: 22
<212> TYPE: DNA
<213> ORGANISM: Mus musculus

<400> SEQUENCE: 363
taaccgattt caaatggtgc ta                                              22

<210> SEQ ID NO 364
<211> LENGTH: 22
<212> TYPE: DNA
<213> ORGANISM: Mus musculus

<400> SEQUENCE: 364
aaccgatttc agatggtgct ag                                              22

<210> SEQ ID NO 365
<211> LENGTH: 23
<212> TYPE: DNA
<213> ORGANISM: Mus musculus

<400> SEQUENCE: 365
ccgaccatgg ctgtagactg tta                                             23

<210> SEQ ID NO 366
<211> LENGTH: 22
<212> TYPE: DNA
<213> ORGANISM: Mus musculus

<400> SEQUENCE: 366
tcacaagtta gggtctcagg ga                                              22

<210> SEQ ID NO 367
<211> LENGTH: 22
<212> TYPE: DNA
<213> ORGANISM: Mus musculus

<400> SEQUENCE: 367
aacaagccca gaccgcaaaa ag                                              22

<210> SEQ ID NO 368
<211> LENGTH: 22
<212> TYPE: DNA
<213> ORGANISM: Mus musculus

<400> SEQUENCE: 368
acagttcttc aactggcagc tt                                              22

<210> SEQ ID NO 369
<211> LENGTH: 22
<212> TYPE: DNA
<213> ORGANISM: Mus musculus

<400> SEQUENCE: 369
aactgtacac actactacct ca                                              22

<210> SEQ ID NO 370
<211> LENGTH: 22
<212> TYPE: DNA
<213> ORGANISM: Mus musculus

<400> SEQUENCE: 370
gaaagagacc ggttcactgt ga                                              22
```

```
<210> SEQ ID NO 371
<211> LENGTH: 22
<212> TYPE: DNA
<213> ORGANISM: Mus musculus

<400> SEQUENCE: 371
aaaagagacc ggttcactgt ga                                              22

<210> SEQ ID NO 372
<211> LENGTH: 23
<212> TYPE: DNA
<213> ORGANISM: Mus musculus

<400> SEQUENCE: 372
gaacagatag tctaaacact ggg                                             23

<210> SEQ ID NO 373
<211> LENGTH: 23
<212> TYPE: DNA
<213> ORGANISM: Mus musculus

<400> SEQUENCE: 373
gaacaggtag tctaaacact ggg                                             23

<210> SEQ ID NO 374
<211> LENGTH: 22
<212> TYPE: DNA
<213> ORGANISM: Mus musculus

<400> SEQUENCE: 374
atgccctttt aacattgcac tg                                              22

<210> SEQ ID NO 375
<211> LENGTH: 22
<212> TYPE: DNA
<213> ORGANISM: Mus musculus

<400> SEQUENCE: 375
tatctgcact agatgcacct ta                                              22

<210> SEQ ID NO 376
<211> LENGTH: 23
<212> TYPE: DNA
<213> ORGANISM: Mus musculus

<400> SEQUENCE: 376
tcagttttgc atggatttgc aca                                             23

<210> SEQ ID NO 377
<211> LENGTH: 23
<212> TYPE: DNA
<213> ORGANISM: Mus musculus

<400> SEQUENCE: 377
actcaccgac agcgttgaat gtt                                             23

<210> SEQ ID NO 378
<211> LENGTH: 24
<212> TYPE: DNA
<213> ORGANISM: Mus musculus

<400> SEQUENCE: 378
aacccaccga cagcaatgaa tgtt                                            24
```

```
<210> SEQ ID NO 379
<211> LENGTH: 22
<212> TYPE: DNA
<213> ORGANISM: Mus musculus

<400> SEQUENCE: 379
actcaccgac aggttgaatg tt                                              22

<210> SEQ ID NO 380
<211> LENGTH: 23
<212> TYPE: DNA
<213> ORGANISM: Mus musculus

<400> SEQUENCE: 380
actcaccgag agcgttgaat gtt                                             23

<210> SEQ ID NO 381
<211> LENGTH: 23
<212> TYPE: DNA
<213> ORGANISM: Mus musculus

<400> SEQUENCE: 381
tcatacagct agataaccaa aga                                             23

<210> SEQ ID NO 382
<211> LENGTH: 23
<212> TYPE: DNA
<213> ORGANISM: Mus musculus

<400> SEQUENCE: 382
acaccaatgc cctaggggat gcg                                             23

<210> SEQ ID NO 383
<211> LENGTH: 22
<212> TYPE: DNA
<213> ORGANISM: Mus musculus

<400> SEQUENCE: 383
tcgccctctc aacccagctt tt                                              22

<210> SEQ ID NO 384
<211> LENGTH: 22
<212> TYPE: DNA
<213> ORGANISM: Mus musculus

<400> SEQUENCE: 384
ggagtgaaga cacggagcca ga                                              22

<210> SEQ ID NO 385
<211> LENGTH: 22
<212> TYPE: DNA
<213> ORGANISM: Mus musculus

<400> SEQUENCE: 385
tccctctggt caaccagtca ca                                              22

<210> SEQ ID NO 386
<211> LENGTH: 18
<212> TYPE: DNA
<213> ORGANISM: Artificial Sequence
<220> FEATURE:
<223> OTHER INFORMATION: Primer sequence

<400> SEQUENCE: 386
```

```
acggaattcc tcactaaa                                          18

<210> SEQ ID NO 387
<211> LENGTH: 19
<212> TYPE: DNA
<213> ORGANISM: Artificial Sequence
<220> FEATURE:
<223> OTHER INFORMATION: Primer sequence

<400> SEQUENCE: 387
tactggaatt cgcggttaa                                         19
```

HIGH THROUGHPUT METHODS RELATING TO MICRORNA EXPRESSION ANALYSIS

PRIORITY CLAIM

This application claims priority from U.S. Provisional Application Ser. No. 60/584,381, filed Jun. 30, 2004, and from U.S. Provisional Application Ser. No. 60/607,531, filed Sep. 7, 2004, both of which are incorporated herein by reference.

BACKGROUND OF THE INVENTION

The invention relates to methods and compositions for microRNA expression analysis using microarrays.

MicroRNAs are a new class of small regulatory RNAs that are found in a variety of organisms, including nematodes, plants, insects and mammals. In invertebrates, microRNAs have been implicated as regulators of developmental timing, neuronal differentiation, cell proliferation, programmed cell death, and fat metabolism. In C. elegans, lin-4 and let-7 act in developmental timing, and the microRNA lsy-6 controls neuronal asymmetry. In Drosophila, the microRNAs bantam and mir-14 act in the regulation of cell growth, spermatogenesis and cell death. The mouse microRNA miR-181 functions in hematopoietic differentiation, and two human microRNAs are involved in chronic lymphocytic leukemia, the most common form of adult leukemia in the western world.

Mature microRNAs are excised from a stem-loop precursor that itself can be transcribed as part of a longer primary RNA (pri-miRNA). The pri-miRNA appears to be processed by the RNAse Drosha in the nucleus, cleaving the RNA at the base of the stem-loop. This cut defines one end of the microRNA. The precursor microRNA is then exported by Ran-GTP and Exportin-5 to the cytoplasm, where it is further processed by the RNAse Dicer, which recognizes the stem portion of the microRNA and cleaves both strands about 22 nucleotides from the base of the stem. The two strands of the resulting dsRNA are differentially stable, and the mature microRNA resides on the strand that is more stable. Mature microRNAs can be found associated with the proteins eIF2C2 (an Argonaute-like protein), Gemin2, and Gemin3 and are thought to act in a protein-RNA complex with these and maybe other proteins.

Most animal microRNAs inhibit the protein expression of their target gene. Typically, the target gene encodes an mRNA that contains a sequence in its 3'UTR that is partially complementary to the corresponding microRNA. While some plant microRNAs also function in this way, most plant microRNAs cause the cleavage of target mRNAs at sites that are perfectly complementary to the microRNAs.

More than 200 microRNAs are encoded by the human genome. Few of these microRNAs have been characterized. To date, the function of individual microRNAs has been analyzed using time-intensive procedures, such as dot-blot and northern blotting analysis, techniques that require the isolation of large amounts of RNA. A need exists for a high-throughput method that allows for the simultaneous analysis of multiple microRNAs and that provides for the analysis of microRNA expression when only small amounts of starting material are available.

SUMMARY OF THE INVENTION

In general, the invention relates to methods and compositions for microRNA expression analysis using microarrays. As described in more detail below, these methods allow for the detection of all known microRNAs of a given species in parallel. Unlike existing methods of mRNA analysis, the methods described herein optionally provide for the amplification of microRNAs. This amplification step facilitates the analysis of a wide range of biological materials, including small quantities of biological samples containing a limited amount of RNA.

In addition, existing methods fail to provide methods suitable for labeling RNAs as small as microRNAs. To address this need, we disclose herein a method to detectably label small RNAS. The method includes the following steps. First, small RNAs (e.g., 18-26 nucleotides) are size-selected from total RNA, for example, by using denaturing polyacrylamide gel electrophoresis. Oligonucleotide linkers (e.g., DNA, RNA, RNA/DNA hybrid, or having a block at the 3' end to inhibit self ligation) are attached to the 5' and 3' ends of the small RNAs. These linkers are at least 5, 10, 12, 15, 18, 20, or 25 nucleotides in length. Such linkers optionally include sites that facilitate subsequent cloning (e.g., restriction sites), sites that promote transcription (e.g., T7 site), or sites that facilitate the purification of the microRNA (e.g., a biotin). These ligation products are optionally used as templates for amplification (e.g., RT-PCR reaction with 10 cycles of amplification). The sense-strand PCR primer contains a detectable label (e.g., a fluorescent label, an enzyme, radiolabel, or other detectable group). Binding of the detectably labeled microRNA to an oligonucleotide that is at least partially complementary to the microRNA is determined using standard techniques based on a characteristic of the detectable group such as its enzyme activity, radioactivity, or fluorescence. In one working embodiment, a Cy3 fluorophore is attached to the PCR primer's 5' end, thereby fluorescently labeling the sense strand of the PCR product. The PCR product is then denatured and hybridized to a microarray. In contrast to existing methods that rely on substantial quantities of starting material, when the microRNA is amplified prior to hybridization, relatively low amounts of starting material may be used. Thus, the present invention is particularly advantageous for analyzing microRNA expression in a biological sample (e.g., biopsy specimen) isolated from a patient.

While the detectably labeled microRNA may be hybridized to any complementary oligonucleotide, it is preferably hybridized to a microarray that includes 10, 25, 50, 75, 100, 125, 150, 175, 200, 250, 300, 400, 500, 750, or 1000 oligonucleotides. Some of these oligonucleotides are complementary to the detectably labeled microRNAs. Optionally, at least one or more negative control oligonucleotides are included that fail to bind a microRNA. Optionally, at least one or more positive control probes are included that bind a microRNA. Such probes contain a means for affixing the probe to a solid substrate (e.g., a membrane, glass slide, bead). Optionally, this means is a free amine group at the 5' terminus that allows the probe to be attached (e.g., printed) onto an amine-binding glass slides. The probes are covalently linked to the glass surface. In some examples, the probes are affixed to the substrate in duplicate, triplicate, or quadruplicate. Hybridization is carried out at any temperature that optimizes binding sensitivity and specificity, i.e, a temperature that allows the detectably labeled microRNA to specifically bind to an oligonucleotide that is at least partially complementary to the microRNA. Preferably, a hybridization temperature between 40° C. and 60° C. is selected, more preferably between 45° C. and 55° C. (e.g., 47° C., 48° C., 49° C., 51° C., 53° C.), and most preferably the hybridization is carried out at 50° C.

In a first aspect, the invention generally features a method for identifying microRNA expression in a sample. The method includes providing a microRNA isolated from a sample; appending at least one linker to the microRNA; detectably labeling the microRNA; contacting a microarray comprising at least 2 oligonucleotides with the detectably labeled microRNA; and detecting binding of the detectably labeled microRNA to the microarray.

In another aspect, the invention features a method for identifying microRNA expression in a sample, the method includes providing a microRNA isolated from a sample; amplifying the microRNA to produce a detectably labeled microRNA; contacting a microarray comprising at least 2 oligonucleotides with the detectably labeled microRNA; and detecting binding of the detectably labeled microRNA to the microarray.

In another aspect, the invention features a method for identifying differential expression of a microRNA in a test sample. The method includes providing a microRNA isolated from the test sample; appending at least one linker to the microRNA; detectably labeling the microRNA; contacting a microarray comprising at least 2 microRNAs with the detectably labeled microRNA; and detecting a difference in the binding of the detectably labeled microRNA to the microarray relative to the binding of a corresponding control sample.

In another aspect, the invention features a method for identifying differential expression of a microRNA in a test sample. The method includes providing a microRNA isolated from a test sample; amplifying the microRNA to produce a detectably labeled microRNA; contacting a microarray comprising at least 2 microRNAs with the detectably labeled microRNA; and detecting a difference in the binding of the detectably labeled microRNA to the microarray relative to the binding of a corresponding control sample.

In some embodiments of the above aspects, the test sample is a tissue sample from a subject having a disease, condition, or disorder selected from the group consisting of autoinflammatory disorders (e.g., asthma, allergic intraocular inflammatory diseases, arthritis, atopic dermatitis, atopic eczema, diabetes, haemolytic anaemia, inflammatory dermatoses, inflammatory bowel or gastrointestinal disorders, multiple sclerosis, myasthenia gravis, pruritis/inflammation, psoriasis, rheumatoid arthritis, and systemic lupus erythematosus), proliferative diseases (e.g., leukemias, lymphomas, sarcomas and carcinomas), cardiovascular diseases (e.g., atherosclerosis, hypertension, cardiac artery disease, myocardial infarction, or congestive heart failure), obesity, or an obesity related diseases (e.g., diabetes).

In another aspect, the invention features a method of diagnosing a subject as having, or having a propensity to develop, a microRNA-related disorder. The method includes providing a microRNA isolated from a cell of the subject; appending at least one linker to the microRNA or amplifying the microRNA from the subject; detectably labeling the microRNA; and determining the level of expression of the microRNA, where an alteration in the level of expression of the microRNA relative to a reference, indicates that the patient has or has a propensity to develop a microRNA-related disorder.

In another aspect, the invention features a method for producing a detectably labeled microRNA. The method includes providing an isolated microRNA, and attaching a linker bound to a to detectable label to the microRNA.

In yet another aspect, the invention features a method for producing a detectably labeled microRNA. The method includes amplifying a microRNA from a sample, and detectably labeling the microRNA.

In a related aspect, the invention features a detectably labeled microRNA produced according to the methods of any of the above aspects.

In another aspect, the invention features a method for producing a microRNA microarray. The method includes providing a microRNA; appending at least one linker to the microRNA; and affixing the detectably labeled microRNAs to a solid support.

In yet another aspect, the invention features a method for producing a microRNA microarray, the method includes providing at least 2, 5, 10, 25, 50, 75, 100, 125, 150, 175, 200 microRNAs; amplifying the microRNAs; and affixing the microRNAs to a solid support (e.g., a bead or a glass slide). In some embodiments, the microRNAs contain a detectable label. In other embodiments, the bead has a characteristic that provides for its identification (e.g., fluorophore, size, color, charge, or any other identifiable signal or modification).

In yet another aspect, the invention features a method of microRNA hybridization. The method includes contacting a microRNA probe and a target nucleic acid at a temperature between 40° and 60° C., 45° C. and 55° C., or at 50° C. under conditions suitable for binding.

In another aspect, the invention features a kit for microRNA expression analysis. The kit contains at least 2 detectably labeled microRNAs produced according to any method of a previous aspect, where the microRNAs are bound to a substrate and the kit further contains directions for the use of the detectably labeled microRNAs for the detection of microRNA expression.

In various embodiments of any of the above aspects, the linker contains oligonucleotides (e.g., RNA, DNA, or is an RNA/DNA hybrid). In other embodiments, one or two linkers are appended in a ligation reaction. In another embodiment, the microRNA is useful as a template for a reverse transcriptase polymerase chain reaction (RT-PCR). In yet another embodiment, the microRNA is detectably labeled during the performance of the polymerase chain reaction (PCR). In another embodiment, the linker contains a T7 promoter, at least one restriction site, or a modification that facilitates purification of the microRNA (e.g., biotin).

In various embodiments of any of the above aspects, the microRNA is detectably labeled during the performance of PCR. In some embodiments, the detectable label is a fluorophore. In other embodiments of the above aspects, the detectable label is detected by analyzing enzyme activity, by direct immunoassay, or by a radiometric assay. In still other embodiments, the sample is a tissue sample (e.g., a neoplastic tissue sample). In yet other embodiments, the microarray contains at least 10, 25, 50, 75, or 100 oligonucleotides. In other embodiments of any of the above aspects, the microRNA is one of those listed in Table 1 or 2, or disclosed herein.

In another aspect, the invention features a microarray containing at least two nucleic acid molecules, or fragments thereof, which are regulated in the developing rat brain, bound to a solid support, where at least 90% of the nucleic acid molecules on the support are selected from any one or more of the group consisting of rno-miR-b, rno-let-7a, rno-let-7b, rno-let-7c, rno-let-7d, rno-let-7i, rno-miR-7, rno-miR-9, rno-miR-16, rno-miR-17-5p, rno-miR-24, rno-miR-26b, rno-miR-28, rno-miR-29a, rno-miR-29b, rno-miR-29c, rno-miR-30b, rno-miR-30c, rno-miR-92, rno-miR-93, rno-miR-99a, rno-miR-99b, rno-miR-101b, rno-miR-103, rno-miR-124a, rno-miR-125a, rno-miR-125b, rno-miR-127, rno-miR-128a, rno-miR-128a or b, rno-miR-128b, rno-miR-129, rno-miR-130a, rno-miR-132, rno-miR-136, rno-miR-138, rno-miR-139, rno-miR-140*, rno-miR-142-3p, rno-miR-145, rno-miR-146, rno-miR-150, rno-miR-154, rno-miR-185, rno-miR-191, rno-miR-213, rno-miR-300, rno-miR-323, rno-miR-324, rno-miR-325, rno-miR-338, rno-miR-342, and rno-miR-345, or any nucleic acid molecule listed in Table 2.

In another aspect, the invention features a purified nucleic acid library containing at least two nucleic acid molecules that are regulated in the developing rat brain selected from any one or more of the group consisting of rno-miR-b, rno-let-7a, rno-let-7b, rno-let-7c, rno-let-7d, rno-let-7i, rno-miR-7, rno-miR-9, rno-miR-16, rno-miR-17-5p, rno-miR-24, rno-miR-26b, rno-miR-28, rno-miR-29a, rno-miR-29b, rno-miR-29c, rno-miR-30b, rno-miR-30c, rno-miR-92, rno-miR-93, rno-miR-99a, rno-miR-99b, rno-miR-101b, rno-miR-103, rno-miR-124a, rno-miR-125a, rno-miR-125b, rno-miR-127, rno-miR-128a, rno-miR-128a or b, rno-miR-128b, rno-miR-129, rno-miR-130a, rno-miR-132, rno-miR-136, rno-miR-138, rno-miR-139, rno-miR-140*, rno-miR-142-3p, rno-miR-145, rno-miR-146, rno-miR-150, rno-miR-154, rno-miR-185, rno-miR-191, rno-miR-213, rno-miR-300, rno-miR-323, rno-miR-324, rno-miR-325, rno-miR-338, rno-miR-342, and rno-miR-345 or a nucleic acid molecule listed in Table 2.

In yet another aspect, the invention features a microarray comprising at least two nucleic acid molecules, or fragments thereof, that are regulated in the developing rat brain and bound to a solid support, where at least 90% of the nucleic acid molecules on the support are selected from any one or more of the group consisting of mml-let-7a, mml-let-7a or c, mml-let-7b, mml-let-7c, mml-let-7d, mml-let-7e, mml-let-7f, mml-let-7g, mml-let-7i, mml-miR-7-1, mml-miR-9, mml-miR-16, mml-miR-17-5p, mml-miR-26a, mml-miR-30b, mml-miR-30c, mml-miR-33, mml-miR-92, mml-miR-99a, mml-miR-99b, mml-mir-100, mml-miR-103, mml-miR-103 or 107, mml-miR-124a, mml-miR-124a, mml-miR-125a, mml-miR-125b, mml-miR-126, mml-miR-126*, mml-miR-128a, mml-miR-128a or b, mml-miR-128b, mml-miR-129-2, mml-miR-136, mml-miR-137, mml-miR-140, mml-miR-145, mml-miR-149, mml-miR-181a or 213, mml-miR-181b, mml-miR-181c, mml-miR-185, mml-miR-195, and mml-miR-221.

In yet another aspect, the invention features a purified nucleic acid library containing at least two nucleic acid molecules regulated in the developing rat brain and selected from any one or more of the group consisting of mml-let-7a, mml-let-7a or c, mml-let-7b, mml-let-7c, mml-let-7d, mml-let-7e, mml-let-7f, mml-let-7g, mml-let-7i, mml-miR-7-1, mml-miR-9, mml-miR-16, mml-miR-17-5p, mml-miR-26a, mml-miR-30b, mml-miR-30c, mml-miR-33, mml-miR-92, mml-miR-99a, mml-miR-99b, mml-mir-100, mml-miR-103, mml-miR-103 or 107, mml-miR-124a, mml-miR-124a, mml-miR-125a, mml-miR-125b, mml-miR-126, mml-miR-126*, mml-miR-128a, mml-miR-128a or b, mml-miR-128b, mml-miR-129-2, mml-miR-136, mml-miR-137, mml-miR-140, mml-miR-145, mml-miR-149, mml-miR-181a or 213, mml-miR-181b, mml-miR-181c, mml-miR-185, mml-miR-195, and mml-miR-221, or any of the nucleic acid molecules listed in Table 2.

By "cell" is meant a single-cellular organism, cell from a multi-cellular organism, or cell contained in a multi-cellular organism.

By "differentially expressed" is meant a difference in the expression level of a nucleic acid or polypeptide in a test sample relative to the level of the nucleic acid in a control sample or relative or other reference. This difference may be either an increase or a decrease in expression, when compared to control conditions. Preferably, the increase or decrease is at least 10%, 20%, 30%, 40%, 50%, 60%, 70%, 80%, 90%, or even 100%.

By "duplex" is meant a single unit containing paired sense and antisense domains.

By "hybridize" is meant pair to form a duplex or double-stranded complex containing complementary paired nucleobase sequences, or portions thereof. Preferably, hybridization occurs under physiological conditions, or under various conditions of stringency. (See, e.g., Wahl and Berger *Methods Enzymol.* 152:399, 1987; Kimmel, A. R. *Methods Enzymol.* 152:507, 1987). For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (*Science* 196:180, 1977); Grunstein and Hogness (*Proc Natl Acad Sci USA* 72:3961, 1975); Ausubel et al. (*Current Protocols in Molecular Biology*, Wiley Interscience, New York, 2001); Berger and Kimmel (*Guide to Molecular Cloning Techniques*, 1987, Academic Press, New York); and Sambrook et al., *Molecular Cloning: A Laboratory Manual*, Cold Spring Harbor Laboratory Press, New York. Typically, complementary nucleobases hybridize via hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "isolated polynucleotide" is meant a nucleic acid (e.g., a DNA) that is free of the genes, which, in the naturally occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by polymerase chain reaction (PCR) or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "linker" is meant a short segment of synthetic oligomer that acts as a connecting element. Such elements are typically used in connecting longer nucleic acid segments.

By "microRNA" is meant a small non-coding RNA. Typically, microRNAs are 15, 16, 17, 18, 19, 20, 21, 22, 23, 24, 25, 26, 27, or 28 nucleotides in length and are processed from a precursor RNA containing a stem-loop.

By "microRNA-related disorder" is meant a pathological condition associated with an alteration in the sequence, expression, or biological activity of a microRNA. In one example, a microRNA-related disorder is a neoplasm characterized as having a decrease in the expression of a microRNA.

By "microarray" is meant an organized collection of at least two nucleic acid molecules affixed to a solid support. In some embodiments, a microRNA microarray is composed of oligonucleotides having at least a portion (e.g., 10, 15, 18, 20, 21, 22, 23, 24, 25, 26, 27, 28, 29, 30, 40, 50, 60, 70, 80, 90, or 100 nucleotides) of two or more nucleic acid sequences listed in Table 1 or 2. A microarray contains at least 2, 5, 10, 25, 50, 75, 100, 150, 200, 250, or 300 nucleic acid molecule members.

By "portion" is meant a fragment of a protein or nucleic acid that is substantially identical to a reference protein or nucleic acid. In some embodiments the portion retains at least 50% 75%, or 80%, or more preferably 90%, 95%, or even 99% of the biological activity of the reference protein or nucleic acid described herein.

By "operably linked" is meant that a first polynucleotide is positioned adjacent to a second polynucleotide that directs transcription of the first polynucleotide when appropriate molecules (e.g., transcriptional activator proteins) are bound to the second polynucleotide.

By "proliferative disease" is meant a disease that is caused by or results in inappropriately high levels of cell division, inappropriately low levels of apoptosis, or both. For example, cancer is an example of a proliferative disease. Examples of cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma).

By "positioned for expression" is meant that the polynucleotide of the invention (e.g., a DNA molecule) is positioned adjacent to a DNA sequence that directs transcription and translation of the sequence (i.e., facilitates the production of, for example, a recombinant polypeptide of the invention, or an RNA molecule).

By "promoter" is meant a polynucleotide sufficient to direct transcription.

By "polypeptide" is meant any chain of amino acids, regardless of length or post-translational modification (for example, glycosylation or phosphorylation).

By "reporter gene" is meant a gene encoding a polypeptide whose expression may be assayed; such polypeptides include, without limitation, glucuronidase (GUS), luciferase, chloramphenicol transacetylase (CAT), and beta-galactosidase.

The invention features methods and compositions relating to the analysis of microRNAs. Other features and advantages of the invention will be apparent from the detailed description, and from the claims.

BRIEF DESCRIPTION OF THE DRAWINGS

FIG. 1 A is an alignment of the top BLAST hit for each mouse microRNA precursor sequence (Rfam, Release 3.0) with the corresponding rat genomic sequence (public release draft genome assembly, version 3.1) (SEQ ID NOS:227-334). FIG. 1A shows mouse let-7a- 1 (SEQ ID NO:227) and the corresponding rat sequence (SEQ ID NO:228); mouse let-7a-2 (SEQ ID NO:229) and the corresponding rat sequence (SEQ ID NO:230); mouse let-7b (SEQ ID NO: 231) and the corresponding rat sequence (SEQ ID NO: 232); mouse let-7c-1(SEQ ID NO: 233) and the corresponding rat sequence (SEQ ID NO:234); mouse let-7c-2 (SEQ ID NO:235) and the corresponding rat sequence (SEQ ID NO:236); mouse let-7e (SEQ ID NO:237) and the corresponding rat sequence (SEQ ID NO:238); mouse let-7i (SEQ ID NO:239) and the corresponding rat sequence (SEQ ID NO:240); mouse miR-7-1

(SEQ ID NO:241) and the corresponding rat sequence (SEQ ID NO:242); mouse miR-7-2 (SEQ ID NO:243) and the corresponding rat sequence (SEQ ID NO:244); mouse miR-9-1 (SEQ ID NO:245) and the corresponding rat sequence (SEQ ID NO:246); mouse miR-9-3 (SEQ ID NO:247) and the corresponding rat sequence (SEQ ID NO:248); mouse miR-9-2 (SEQ ID NO:249) and the corresponding rat sequence (SEQ ID NO:250); mouse miR-16-2 (SEQ ID NO:251) and the corresponding rat sequence (SEQ ID NO:252); mouse miR-24-1(SEQ ID NO:253) and the corresponding rat sequence (SEQ ID NO:254); mouse miR-24-2 (SEQ ID NO:255) and the corresponding rat sequence (SEQ ID NO:256); mouse miR-26b (SEQ ID NO:257) and the corresponding rat sequence (SEQ ID NO:258); mouse miR-28 (SEQ ID NO:259) and the corresponding rat sequence (SEQ ID NO:260); mouse miR-29a (SEQ ID NO:261) and the corresponding rat sequence (SEQ ID NO:262); mouse miR-29c (SEQ ID NO:263) and the corresponding rat sequence (SEQ ID NO:264); mouse miR-29b-1(SEQ ID NO:265) and the corresponding rat sequence (SEQ ID NO:266); mouse miR-29b-2 (SEQ ID NO:267) and the corresponding rat sequence (SEQ ID NO:268); mouse miR-30b (SEQ ID NO:269) and the corresponding rat sequence (SEQ ID NO:270); mouse miR-30c-1(SEQ ID NO:271) and the corresponding rat sequence (SEQ ID NO:272); mouse miR-30c-2 (SEQ ID NO:273) and the corresponding rat sequence (SEQ ID NO:274); mouse miR-92-2 (SEQ ID NO:275) and the corresponding rat sequence (SEQ ID NO:276); mouse miR-93 (SEQ ID NO:277) and the corresponding rat sequence (SEQ ID NO:278); mouse miR-99a (SEQ ID NO:279) and the corresponding rat sequence (SEQ ID NO:280); mouse miR-99b (SEQ ID NO:281) and the corresponding rat sequence (SEQ ID NO:282); mouse miR-103-1 (SEQ ID NO:283) and the corresponding rat sequence (SEQ ID NO:284); mouse miR-103-2 (SEQ ID NO:285) and the corresponding rat sequence (SEQ ID NO:286); mouse miR-124a-1 (SEQ ID NO:287) and the corresponding rat sequence (SEQ ID NO:288); mouse miR-124a-2 (SEQ ID NO:289) and the corresponding rat sequence (SEQ ID NO:290); mouse miR-124a-3 (SEQ ID NO:291) and the corresponding rat sequence (SEQ ID NO:292); mouse miR-125a (SEQ ID NO:293) and the corresponding rat sequence (SEQ ID NO:294); mouse miR- 125b-2 (SEQ ID NO:295) and the corresponding rat sequence (SEQ ID NO:296); mouse miR-125b-1 (SEQ ID NO:297) and the corresponding rat sequence (SEQ ID NO:298); mouse miR-127 (SEQ ID NO:299) and the corresponding rat sequence (SEQ ID NO:300); mouse miR-128a (SEQ ID NO:301) and the corresponding rat sequence (SEQ ID NO:302); mouse miR-128b (SEQ ID NO:303) and the corresponding rat sequence (SEQ ID NO:304); mouse miR-130a (SEQ ID NO:305) and the corresponding rat sequence (SEQ ID NO:306); mouse miR-132 (SEQ ID NO:307) and the corresponding rat sequence (SEQ ID NO:308); mouse miR-136 (SEQ ID NO:309) and the corresponding rat sequence (SEQ ID NO:310); mouse miR-138-1 (SEQ ID NO:311) and the corresponding rat sequence (SEQ ID NO:312); mouse miR-138-2 (SEQ ID NO:3 13) and the corresponding rat sequence (SEQ ID NO:314); mouse miR-139 (SEQ ID NO:3 15) and the corresponding rat sequence (SEQ ID NO:316); mouse miR-142 (SEQ ID NO:317) and the corresponding rat sequence (SEQ ID NO:3 18); mouse miR-145 (SEQ ID NO:319) and the corresponding rat sequence (SEQ ID NO:320); mouse miR-146 (SEQ ID NO:321) and the corresponding rat sequence (SEQ ID NO:322); mouse miR-150 (SEQ ID NO:323) and the corresponding rat sequence (SEQ ID NO:324); mouse miR-154 (SEQ ID NO:325) and the corresponding rat sequence (SEQ ID NO:326); mouse miR-185 (SEQ ID NO:327) and the corresponding rat sequence (SEQ ID NO:328); mouse miR-191 (SEQ ID NO:329) and the corresponding rat sequence (SEQ ID NO:330;: mouse miR-213 (SEQ ID NO:331) and the corresponding rat sequence (SEQ ID NO:332); and mouse miR-300 (SEQ ID NO:333) and the corresponding rat sequence (SEQ ID NO:334). FIG. 1B shows predicted precursor secondary structures for selected rat microRNA genes (SEQ ID NOS:335-352). FIG. 1B shows the structure of rno-let-7a-2 (SEQ ID NO: 335), rno-let-7b (SEQ ID NO: 336), rno-mir-7-1 (SEQ ID NO: 337), rno-mir-7-2 (SEQ ID NO: 338), rno-mir-16-2 (SEQ ID NO: 339), rno-mir-24-2 (SEQ ID NO: 340), rno-mir-26b (SEQ ID NO: 341), rno-mir-28 (SEQ ID NO: 342), rno-mir-30b (SEQ ID NO: 343), rno-30c-2 (SEQ ID NO: 344), rno-mir-92-2 (SEQ ID NO: 345), rno-mir-93 (SEQ ID NO: 346), rno-mir-99a (SEQ ID NO: 347), rno-mir-125-b2 (SEQ ID NO: 348), rno-mir-130a (SEQ ID NO: 349), rno-mir-138-1 (SEQ ID NO: 350), mo-mir-138-2 (SEQ ID NO: 351), and rno-mir-146 (SEQ ID NO: 352). The selected rat microRNA genes have microRNA precursor sequences that differ from their corresponding mouse precursors. We used the infold algorithm to make secondary structure predictions (Zuker NucleicAcids Res, 3 1:3406-3415, 2003).

FIG. 2B shows an alignment of rat (SEQ ID NO:354), human (SEQ ID NO:355, and mouse (SEQ ID NO:356) precursor sequences for microRNA mir-B. The cloned sequence (corresponding to the mature microRNA) is shown in bold. The single mismatch is indicated by an asterix (*).

FIG. 8A shows the profile of microRNA expression at embryonic day 12.5 in mouse brain for those microRNAs that exhibit a sharp peak in expression at this stage. The oligonucleotide sequences EAM261 (SEQ ID NO:360), EAM206 (SEQ ID NO:361), EAM119 (SEQ ID NO:362), EAM279 (SEQ ID NO:363), EAM268 (SEQ ID NO:364), EAM137 (SEQ ID NO:365), EAM105 (SEQ ID NO:366), EAM289 (SEQ ID NO:367), EAM255 (SEQ ID NO:368), EAM182 (SEQ ID NO:369), EAM195 (SEQ ID NO:370), and EAM 194 (SEQ ID NO:371) are also shown. Similar sequences are indicated with brackets. FIG. 8B shows the profile of microRNA expression in adult rat brain for microRNAs that exhibit a single sharp peak in expression at the adult stage. The oligonucleotide sequences EAM235 (SEQ ID NO:372), EAM282 (SEQ ID NO:373), EAM 159 (SEQ ID NO:374), EAM225 (SEQ ID NO:375), EAM237 (SEQ ID NO:376), EAM226 (SEQ ID NO:377), EAM227 (SEQ ID NO:378), EAM228 (SEQ ID NO:379), EAM 156 (SEQ ID NO:380), EAM276 (SEQ ID NO:381), EAM133 (SEQ ID NO:382), EAM175 (SEQ ID NO:383), EAM216 (SEQ ID NO:384), and EAM202(SEQ ID NO:385) are also shown. Methods used in assembling this profile are the same as those described above for FIGS. 7A and 7B. Brackets indicate closely related sequences.

DETAILED DESCRIPTION OF THE INVENTION

Figure 2A:
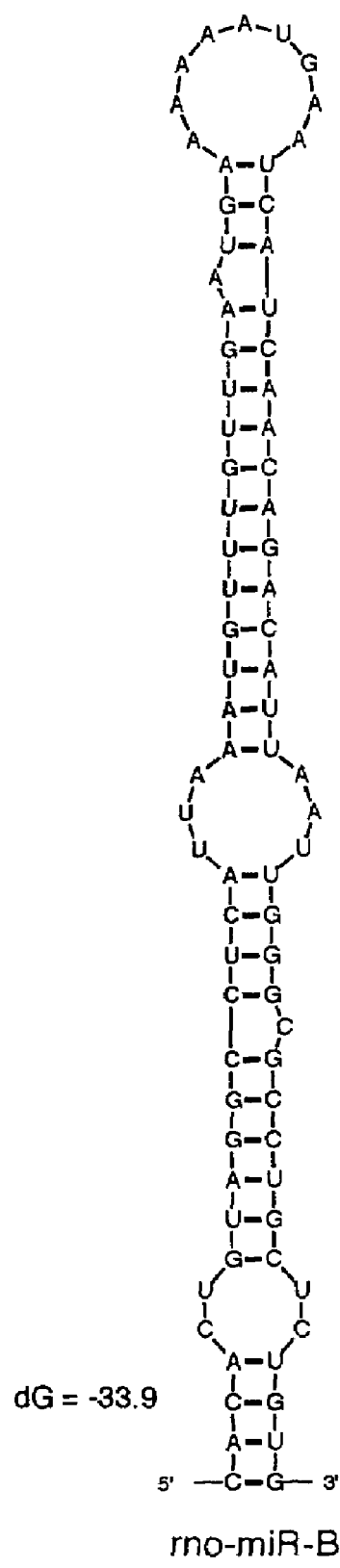
FIG. 2A shows the predicted stem-loop structure of a novel mammalian microRNA, rno-miR-B (SEQ ID NO:353). The stem-loop structure was predicted from sequences adjacent to rno-miR-B in the rat genome. The cloned (mature) sequence is shown in gray. The predicted secondary structure and the free energy calculation ($\Delta G$, kcal/mole) were generated by the infold software (Zuker *Nucleic Acids Res*, 31:3406-3415, 2003).

The present invention provides methods and compositions for the analysis of microRNA expression.

Such methods and compositions are useful for the analysis of microRNAs in virtually any biological sample. In general, the microRNA microarray system that we have developed can be used to determine the expression of all known microRNAs simultaneously for virtually any set of experimental conditions or constraints. Such methods are particularly useful for the analysis of micro RNAs that function in human health and disease and for the identification of drugs that modulate microRNA function.

As described below, we determined the temporal expression pattern of 138 microRNAs in the developing mouse brain and found that the levels of 66 microRNAs changed significantly during development. We identified sets of genes with similar expression patterns, including genes that peaked in expression at different stages of development using methods and compositions that we developed for microRNA expression analysis.

Identification of microRNAs from Developing Rat and Monkey Brains

To analyze microRNAs expressed in the developing mammalian brain, we cloned small 18-26 nucleotide RNAs from the neocortex and hippocampus of a 12-day postnatal rat (*Rattus norvegicus*) and from the cerebral wall of a 114-day old rhesus fetal monkey (*Macaca mulatta*) (Table 1).

TABLE 1

| *Rattus norvegicus* microRNAs | | | *Macaca mulatta* microRNAs | | |
|---|---|---|---|---|---|
| Name | No. times cloned | Size Range | Name | No. times cloned | Size Range |
| rno-miR-b | 2 | | | | |
| rno-let-7a | 3 | 22 | mml-let-7a | 15 | 21 |
| | | | mml-let-7a or c | 1 | 18 |
| rno-let-7b | 1 | 23 | mml-let-7b | 20 | 22-23 |
| rno-let-7c | 10 | 22 | mml-let-7c | 9 | 21-22 |
| rno-let-7d | 1 | 22 | mml-let-7d | 1 | 22 |
| | | | mml-let-7e | 3 | 20-22 |
| | | | mml-let-7f | 3 | 22 |
| | | | mml-let-7g | 2 | 22 |
| rno-let-7i | 1 | 22 | mml-let-7i | 2 | 22 |
| rno-miR-7 | 5 | | | | |
| | | | mml-miR-7-1 | 1 | 22 |
| rno-miR-9 | 2 | | mml-miR-9 | 9 | 21-23 |
| rno-miR-16 | 2 | 22 | mml-miR-16 | 2 | 22 |
| rno-miR-17-5p | 3 | 23 | mml-miR-17-5p | 2 | 22-23 |

TABLE 1-continued

| Rattus norvegicus microRNAs | | | Macaca mulatta microRNAs | | |
|---|---|---|---|---|---|
| Name | No. times cloned | Size Range | Name | No. times cloned | Size Range |
| rno-miR-24 | 6 | 21-22 | | | |
| | | | mml-miR-26a | 3 | 21-22 |
| rno-miR-26b | 1 | 22 | | | |
| rno-miR-28 | 1 | 22 | | | |
| rno-miR-29a | 4 | 22 | | | |
| rno-miR-29b | 7 | 22-23 | | | |
| rno-miR-29c | 2 | 20, 22 | | | |
| rno-miR-30b | 1 | 22 | mml-miR-30b | 2 | 22 |
| rno-miR-30c | 3 | 23-24 | mml-miR-30c | 1 | 21 |
| | | | mml-miR-33 | 2 | 20 |
| rno-miR-92 | 2 | 22 | mml-miR-92 | | |
| rno-miR-93 | 1 | 23 | | | |
| rno-miR-99a | 1 | 21 | mml-miR-99a | 4 | 20-22 |
| rno-miR-99b | 2 | 21, 22 | mml-miR-99b | 2 | 22 |
| | | | mml-mir-100 | 1 | 22 |
| rno-miR-101b | 1 | 22 | | | |
| rno-miR-103 | 3 | 23 | mml-miR-103 | 2 | 22-23 |
| | | | mml-miR-103 or 107 | 1 | 21 |
| rno-miR-124a | 19 | 19-22 | mml-miR-124a | 97 | 18-23 |
| rno-miR-125a | 2 | 22, 24 | mml-miR-125a | 4 | 22-23 |
| rno-miR-125b | 12 | 21-22 | mml-miR-125b | 17 | 20-22 |
| | | | mml-miR-126 | 1 | 21 |
| | | | mml-miR-126* | 1 | 22 |
| rno-miR-127 | 1 | 20 | | | |
| rno-miR-128a | 3 | 21-22 | mml-miR-128a | 9 | 22 |
| rno-miR-128a or b | 2 | 21 | mml-miR-128a or b | 17 | 18-21 |
| rno-miR-128b | 1 | 21 | mml-miR-128b | 8 | 22 |
| rno-miR-129 | 2 | 21-22 | mml-miR-129-2 | 1 | 22 |
| rno-miR-130a | 1 | 22 | | | |
| rno-miR-132 | 6 | 22 | | | |
| rno-miR-136 | 2 | 23 | mml-miR-136 | 1 | 23 |
| | | | mml-miR-137 | 1 | 23 |
| rno-miR-138 | 5 | 23-24 | | | |
| rno-miR-139 | 1 | 23 | | | |
| | | | mml-miR-140 | 1 | 22 |
| rno-miR-140* | 1 | 22 | | | |
| rno-miR-142-3p | 1 | 23 | | | |
| rno-miR-145 | 1 | 23 | mml-miR-145 | 2 | 22 |
| rno-miR-146 | 2 | 23 | | | |
| | | | mml-miR-149 | 2 | 23 |
| rno-miR-150 | 4 | 22-23 | | | |
| rno-miR-154 | 1 | 22 | | | |
| | | | mml-miR-181a or 213 | 4 | 20-25 |
| | | | mml-miR-181b | 1 | 24 |
| | | | mml-miR-181c | 1 | 21 |
| rno-miR-185 | 2 | 22-23 | mml-miR-185 | 1 | 23 |
| rno-miR-191 | 3 | 23-24 | | | |
| | | | mml-miR-195 | 1 | 22 |
| rno-miR-213 | 1 | 22 | | | |
| | | | mml-miR-221 | 3 | 22-23 |
| rno-miR-300 | 1 | 21 | | | |
| rno-miR-323 | 1 | 22 | | | |
| rno-miR-324 | 4 | 23 | | | |
| rno-miR-325 | 1 | 22 | | | |
| rno-miR-338 | 5 | 23 | | | |
| rno-miR-342 | 1 | 25 | | | |
| rno-miR-345 | 1 | 22 | | | |
| | 152 | | Total | 261 | |

Legend:
The rat (rno) and monkey (mml) microRNA names are indicated. Two microRNA names are assigned to the same clone when the cloned sequence is too short to distinguish between the microRNAs. mml-miR-7 and mml-miR-129 are encoded by three and two distinct genomic loci, respectively, although the sequences immediately adjacent to these microRNA sequences differ. The sequences we cloned for mml-miR-7-1 and mml-miR-129-2 were one base longer than that shared by the microRNAs, allowing us to determine the loci from where they originated, as indicated by −1 and −2. Notation follows the Rfam repository guidelines (Griffiths-Jones et al., Nucleic Acids Res 31:439-441, 2003)

Table 1 lists the identity, frequency, and size range of microRNAs cloned from the cortex and hippocampus of 12-day postnatal *R. norvegicus* and the cortex of a 114-day old *M. mulatta* fetus. In both species, at these stages, most neurons have been generated and have begun synaptogenesis (Rakic, Science 241:170-176, 1988; Angevine Nature 192: 766-768, 1961). We identified a total of 1451 sequences, four hundred thirteen of which corresponded to microRNA sequences. These four hundred thirteen sequences defined sixty-eight unique microRNAs that are listed in Table 1.

These sequences generate stem-loop precursors and have corresponding orthologous sequences in the rat and/or human genomes. In all but one case, the microRNAs identified corresponded to known microRNAs from other species.

Rat microRNA Precursors

Using the assembly of the rat genome, we identified candidate genomic locations for all of our rat microRNAs. All of these microRNAs have orthologs in mouse, but none of these microRNAs were previously identified in the rat. An alignment of the top BLAST hit of each mouse microRNA precursor sequence (Rfam, Release 3.0) against the rat genome sequence (public release draft genome assembly, version 3.1) is shown in FIG. 1A. In addition, predicted precursor secondary structures are shown (FIG. 1B) for each rat microRNA gene for which the precursor sequence differs from that of the corresponding mouse precursor. We used the mfold algorithm to make secondary structure predictions (Zuker *Nucleic Acids Res,* 31:3406-3415, 2003).

Figure 3:
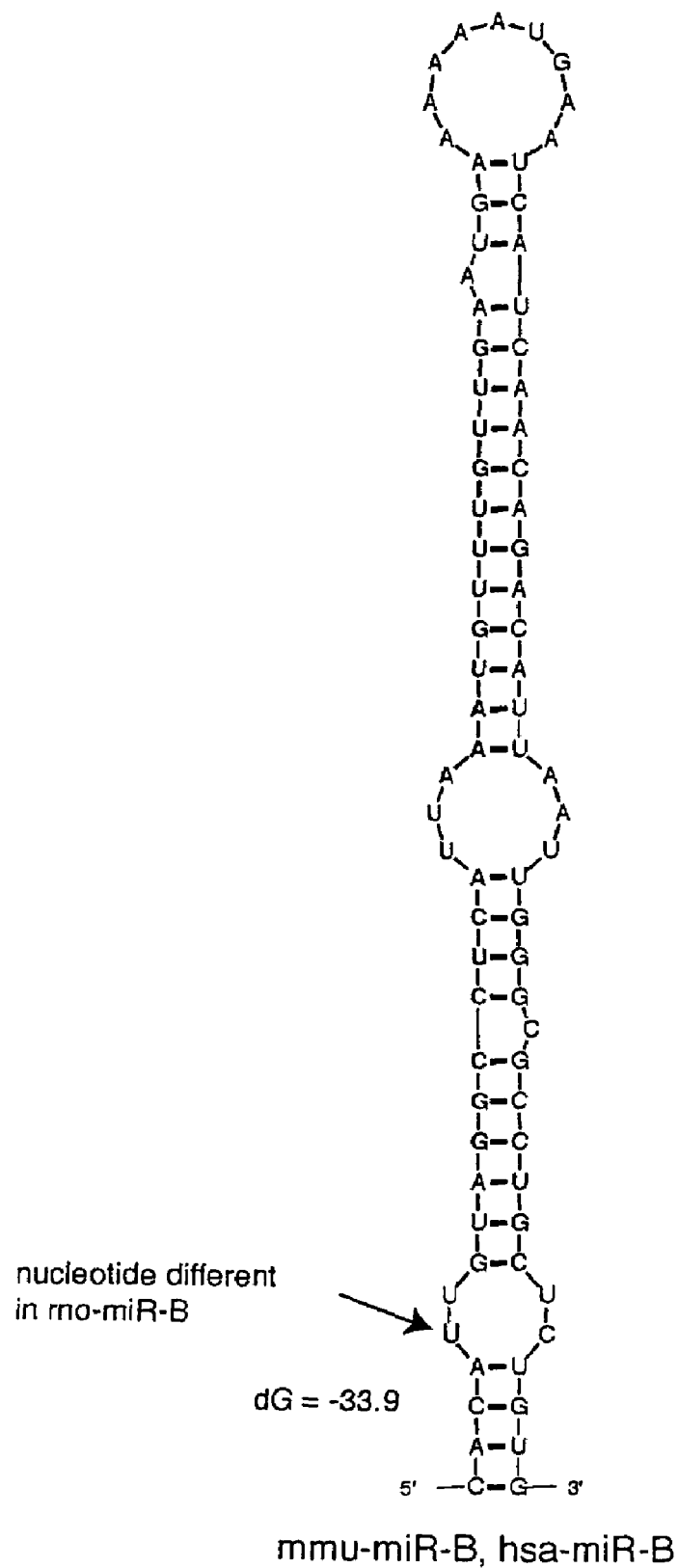
FIG. 3 depicts the predicted secondary structures for the corresponding genes from mouse (SEQ ID NO:357) and human (SEQ ID NO:358) miR-B. The cloned sequence, which corresponds to the mature microRNA, is shown in gray.

One of these microRNAs is novel. It differs in sequence from any microRNA previously described and is conserved in the mouse and human genomes. We named this new microRNA rno-miR-B (FIG. 2A). FIG. 2B shows an alignment of the predicted precursor sequences from human and mouse with the novel microRNA miR-B, which we identified from rat. The cloned sequence, which corresponds to the mature microRNA, is shown in bold (FIG. 2B). The single mismatch is indicated by an asterix (*). The accession number for each sequence is given. The predicted secondary structures for the corresponding genes from mouse and human are shown in FIG. 3. The human and mouse genomic sequences for candidate miR-B precursors are identical. The sequence of the mature microRNA is in gray. The residue in the rat genomic sequence that is different from the mouse and human genomic sequences is indicated with an arrow. We used the mfold algorithm to make secondary structure predictions (Zuker *Nucleic Acids Res,* 31:3406-3415, 2003). We have not been able to detect miR-B in mouse brain using northern blots.

Figure 4:
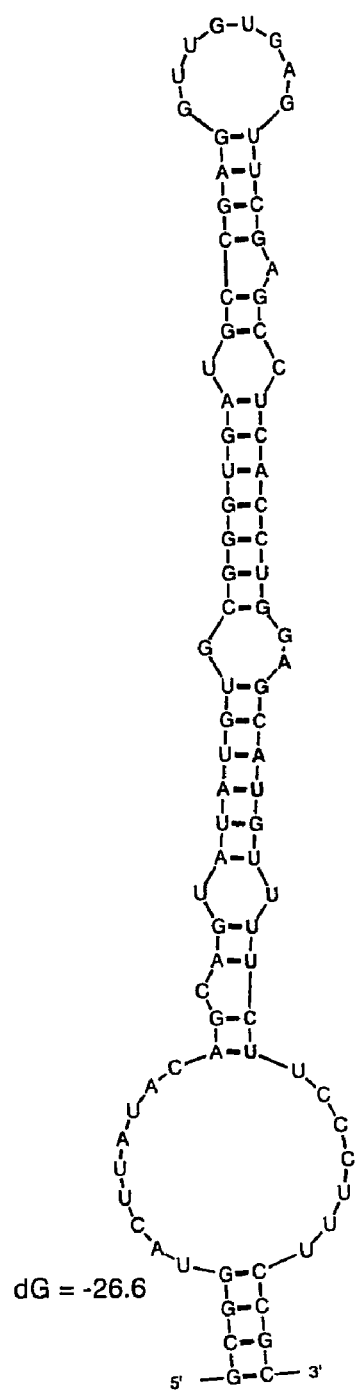
FIG. 4 shows the stem-loop precursor for smallRNA-1 (SEQ ID NO:359) from monkey. The cloned sequence, which corresponds to the mature microRNA, is shown in gray.

In addition to microRNAs, we cloned 13 small RNAs that do not satisfy all criteria to be considered microRNAs. While twelve of these small RNAs are not predicted to form stem-loop structures, smallRNA-1 from monkey has a predicted stem-loop precursor sequence that is characteristic of microRNAs. In smallRNA-1 the stem-loop ends on the final base of the microRNA. Given this atypical structure, we classify this RNA as a small non-coding RNA, rather than a microRNA. A northern blot for smallRNA-1 revealed a high molecular weight band that may represent a precursor RNA. While there is no perfect match to smallRNA-1 in the human genome sequence released to date, a presumptive precursor based on the mouse genomic sequence is shown in FIG. 4. The cloned sequence is in gray. The other small RNAs are not predicted to form stem-loop structures.

Figure 5:
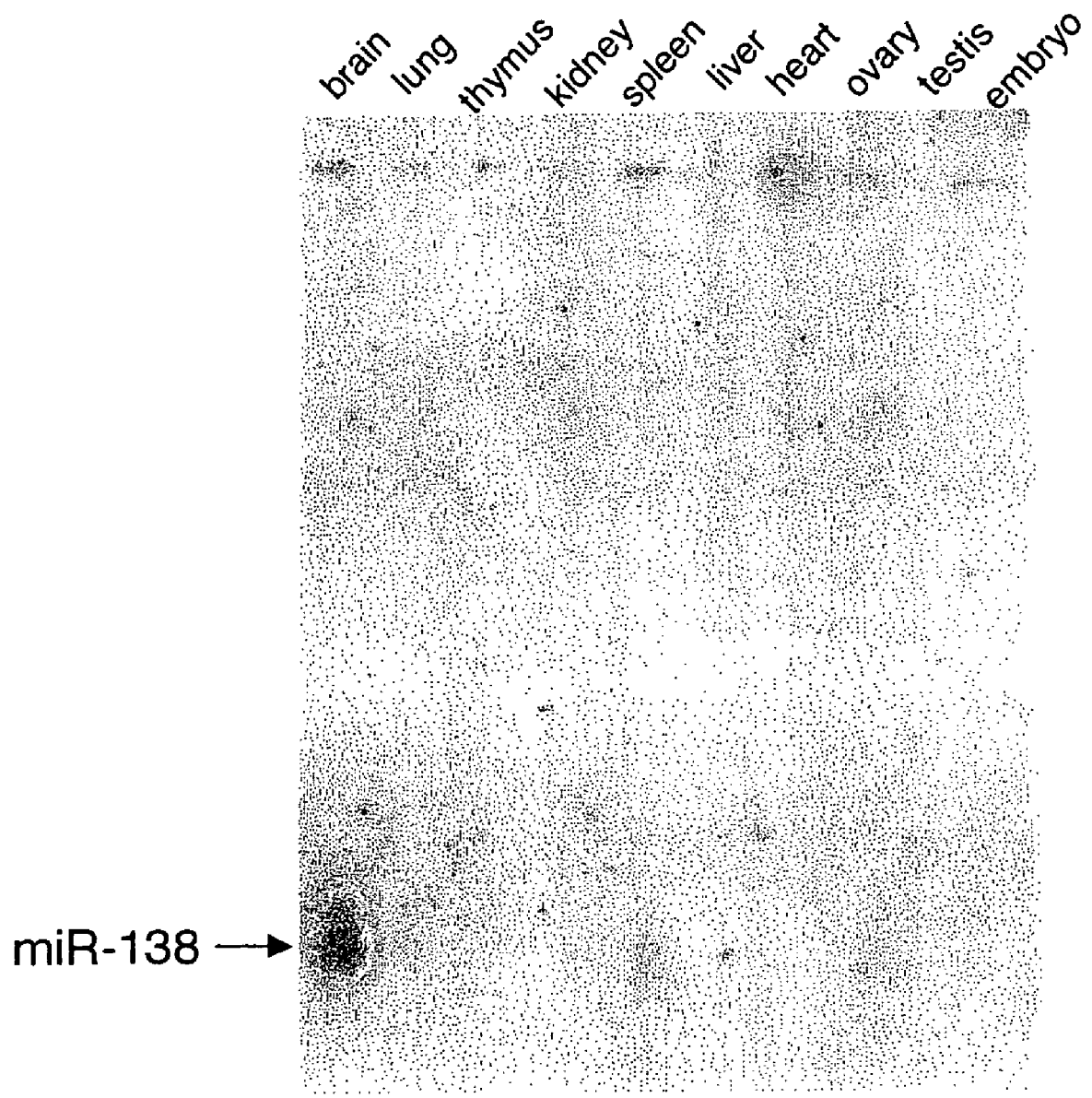
FIG. 5 is a photograph of a Northern blot showing that rno-miR-138 expression was restricted to brain.

Of the fifty-two rat microRNA sequences cloned, twenty-seven were previously cloned from rat primary cortical neurons (Kim et al., *Proc Natl Acad Sci USA* 101:360-365, 2004) (FIG. 1B). For 21 of the 52 microRNAs from rat and 14 of the 40 microRNAs from monkey, we isolated only a single clone, indicating that our surveys are not saturated.

microRNA miR-124a was isolated nineteen times from rat and ninety-seven times from monkey. Mouse miR-124a, miR-128, miR-101, and miR-132 were previously reported to be expressed specifically in brain (Lagos-Quintana et al., *Curr Biol* 12:735-739, 2002). Using Northern blot analysis, we found that rat miR-138 is also expressed exclusively in brain (FIG. 5). The probe was identical to EAM125. Total RNA isolated from various adult rat tissues (AMBION, Austin, Tex.) was size-separated on a denaturing PAGE gel that was loaded with 12 µg RNA per lane. After separation the RNA was transferred to a nylon membrane and used for hybridization. Equal loading was verified using a probe for U6 snRNA.

microRNA Microarrays for the Study of Temporal and Spatial Patterns of microRNA Expression Prior analyses of microRNA expression relied on the individual characterization of each microRNA using dot blots, northern blots, and cloning strategies (Lim et al., *Science,* 299:1540, 2003; Kim et al., *Proc Natl Acad Sci USA* 101:360-365, 2004; Lee et al., *Science* 294:862-864, 2001; Lagos-Quintana *Science* 294:853-858, 2001; Lau et al., *Science* 294:858-862, 2001; Dostie *RNA* 9:180-186, 2003; Krichevsky *RNA* 9:1274-1281, 2003; Sempere *Genome Biol* 5:R13, 2004). We now describe a highly scalable approach using a microarray that provides for the analysis of microRNA expression patterns for a large number of samples simultaneously. We arrayed 138 oligonucleotides complementary to microRNAs (probes) corresponding to the 68 mammalian microRNAs we isolated from rat and monkey brains and to 70 mammalian microRNAs isolated by others from a variety of mouse tissues and mammalian cell lines as well as to predicted microRNAs. In addition, we included a set of control probes as well as 19 probes corresponding to presumptive small RNAs that we and others identified, but that do not satisfy all criteria for a microRNA.

Each probe contained a free amine group at the 5' terminus and was printed onto an amine-binding glass slides. The probes were covalently linked to the glass surface. All probes were printed in quadruplicate.

microRNA Labeling Method

We developed a method for preparing microRNA samples for microarray analysis. Several methods for mRNA sample labeling for microarray analysis have been described (Duggan et al., *Nat Genet* 21(1 Suppl):10-14, 1999; Schena *Science* 270:467-470, 1995; Nimmakayalu et al., *Biotechniques* 28:518-522, 2000; Gupta et al., *Nucleic Acids Res* 31:e13, 2003), but none of these methods is suitable for labeling RNAs as small as microRNAs. To fluorescently label small RNAs we adapted strategies for RNA ligation and reverse transcriptase (RT-) PCR that were devised for microRNA cloning (Lee et al., *Science* 294:862-864, 2001; Lagos-Quintana et al., *Science* 294:853-858, 2001; Lau et al., *Science* 294:858-862, 2001). Briefly, 18-26 nucleotide RNAs were size-selected from total RNA using denaturing polyacrylamide gel electrophoresis. Oligonucleotide linkers were attached to the 5' and 3' ends of the small RNAs and the resulting ligation products were used as templates for an RT-PCR reaction with 10 cycles of amplification. The sense-strand PCR primer had a Cy3 fluorophore attached to its 5' end, thereby fluorescently labeling the sense strand of the PCR product. The PCR product was denatured and then hybridized to the microarray. As in microarray analysis, a labeled sample used for hybridization is referred to as the target. While significant biases in amplification are a problem when heterogeneously sized mRNAs are amplified, such biases are less likely to be problematic when amplifying microRNAs given their short uniform lengths. microRNA cloning frequencies that were obtained using a similar amplification strategy correlated well with expression levels as assayed by quantitative northern blots (Lim et al., *Genes Dev* 2003, 17(8):991-1008). Since RNA is amplified prior to hybridization, relatively low amounts of starting material may be used with this method (Lim et al., *Science,* 299:1540, 2003; Kim et al., *Proc Natl Acad Sci USA* 101:360-365, 2004; Lee et al., *Science* 294:862-864, 2001; Lagos-Quintana *Science* 294:853-858, 2001; Lau et al., *Science* 294:858-862, 2001; Dostie *RNA* 9:180-186, 2003; Krichevsky *RNA* 9:1274-1281, 2003; Sempere *Genome Biol* 5:R13, 2004).

microRNA Hybridization

We optimized the conditions for hybridization to our microarray as follows. Because of the small size of microRNAs, it is difficult to design oligonucleotides (array probes), where the probe and the target melting temperatures are the same. Differences between the melting temperatures of the probe and the target were expected to result in non-specific binding between the probe and the target when hybridizations are performed at low temperatures, which-allows for the detection of bound probe/target pairs with low melting temperatures. If hybridizations are performed at high temperatures to detect probe/target pairs with high melting temperatures, we expected to find less nonspecific binding, but to find a decrease in sensitivity.

We tested a range of hybridization temperatures, and, based on the signal of microRNA probes versus control probes, we determined that a hybridization temperature of 50° C. was a reasonable compromise between sensitivity and specificity. Even at 50° C., specificity as assayed by comparing microarray spot signal intensities from matched and mismatched probes varied among the microRNAs assayed. As expected, specificity at 50° C. was negatively correlated with calculated melting temperatures (FIG. 2A).

Figure 6A:
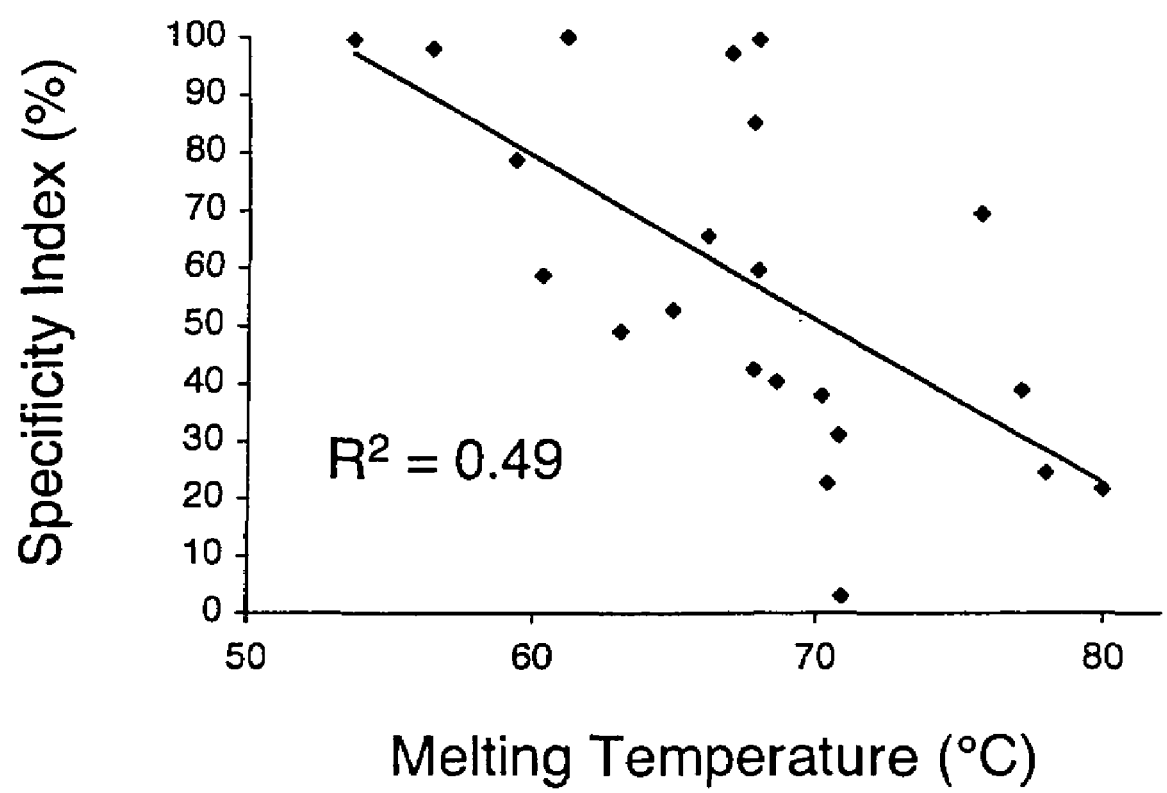
FIG. 6A is a graph depicting the specificity index plotted against the calculated melting temperature for each of 23 microRNA probe pairs. Specificity was assayed using a set of 23 microRNA and mismatched probe pairs (two mismatches). The average mean spot intensities from ten independent hybridizations at 50° C. were added to give a total signal for probes corresponding to a given microRNA as well as for probes with two mismatches to the microRNA. The mismatch probe design and nucleic acid sequences are described in Table 2. The specificity index was calculated as follows: 100× (probe signal—mismatched probe signal)/ probe signal. Melting temperatures for the microRNA probes were calculated using the nearest neighbors method (Breslauer et al., *Proc Natl Acad Sci USA* 1986, 83:3746-3750).
Figure 6B:
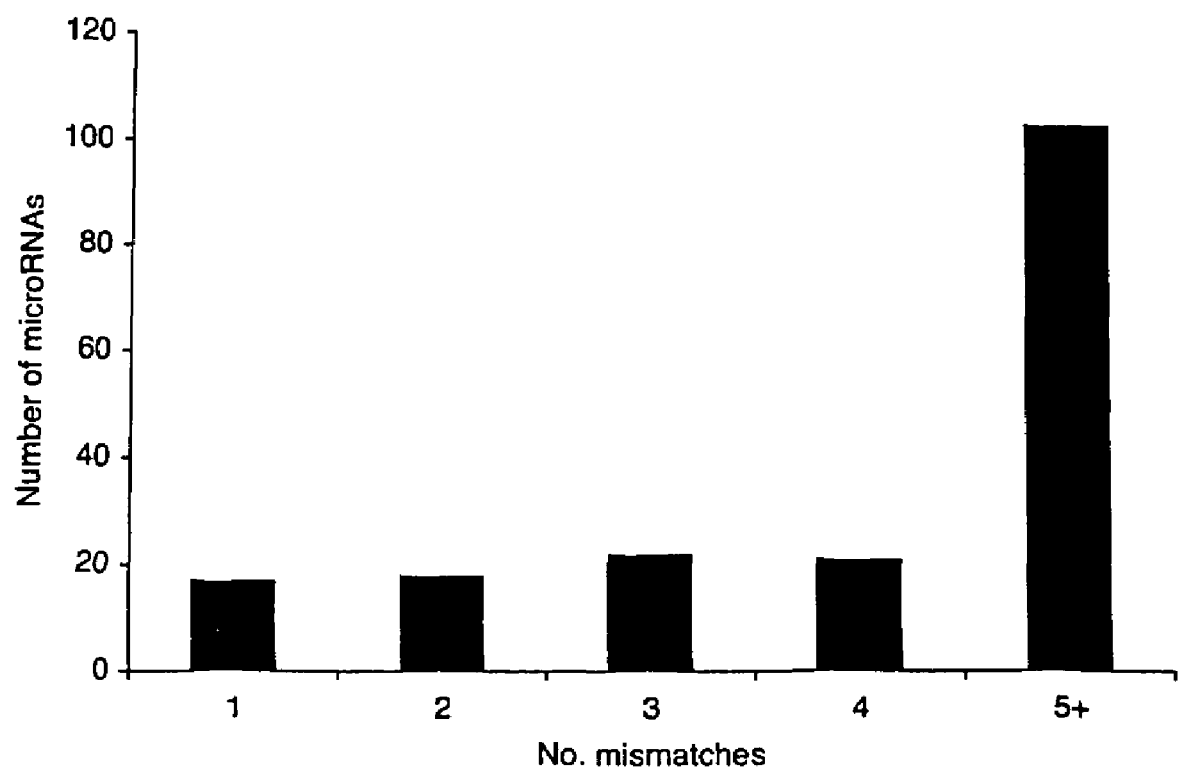
FIG. 6B is a graph depicting the number of mismatches between microRNAs plotted against the number of known mouse microRNAs (Rfam 3.0, January 2004). Each microRNA was aligned pairwise to every other microRNA and was assigned to the group (No. mismatches) corresponding to the least number of mismatches that it had to another microRNA.

Control probes with two internal mismatches on the microarray were included for a subset of the microRNA probes as described in more detail below. In all cases the cumulative signal from 10 hybridizations for the mismatched probe was equal to or lower than that for the microRNA probe, but differences in the ratio of the matched to mismatched probe signal ranged widely (FIG. 6A). Given these data, we did not expect that the microRNA microarray would reliably distinguish between microRNAs that have only one or a few mismatches. Surprisingly, this did not present a problem, most likely because the most closely related paralogs for identified microRNAs differ by five mismatches or more (FIG. 6B). Thus, the signal from a mismatched control probe is typically caused by cross-hybridization with the microRNA for which it was designed. Given these results, it is possible that differences in the apparent expression of a given microRNA may be altered by the expression of microRNA paralogs (FIG. 2A). Control probes corresponding to unrelated mRNA subsequences or synthetic probes that do not correspond to known microRNAs did not show signals above background.

Analysis of microRNA Expression During Mouse Brain Development

We isolated small RNAs from mice at five developmental stages, embryonic days 12.5 and 17.5 (E12.5 and E17.5), postnatal days 4 and 18 (P4 and P18), and 4-month old adults. E12.5-E17.5 spans a period of major neuronal proliferation and migration in the mouse brain, in particular the birth and subsequent migration of most neurons in the ventricular zone epithelium (Chenn et al., *Molecular and Cellular Approaches to Neural Development*. Edited by Cowan W M, Jessell T M, Zipursky S L. New York: Oxford University Press; 1997: 440-473). Between postnatal days P4 and P18 major sensory inputs are established. For example, eye opening occurs around P13 and is thought to result in activity-dependent neuronal remodeling (Chen et al., *Neuron* 28:955-966, 2000). We purified and size-selected RNA from whole mouse brains. For each sample, the products of four independent RNA amplifications based on two independent RNA ligations were hybridized to the array. A detailed description of our analysis of the microarray data is presented below. Of the 138 microRNAs and 19 small RNAs represented by the probe set, 116 (74%) were expressed robustly (greater than 75-fold over the level of background controls) during at least one timepoint. Of these, eighty-three (71%) changed significantly during the period surveyed (analysis of variance, ANOVA, P<0.001) and sixty-six (57%) changed more than two-fold.

Figure 7A:
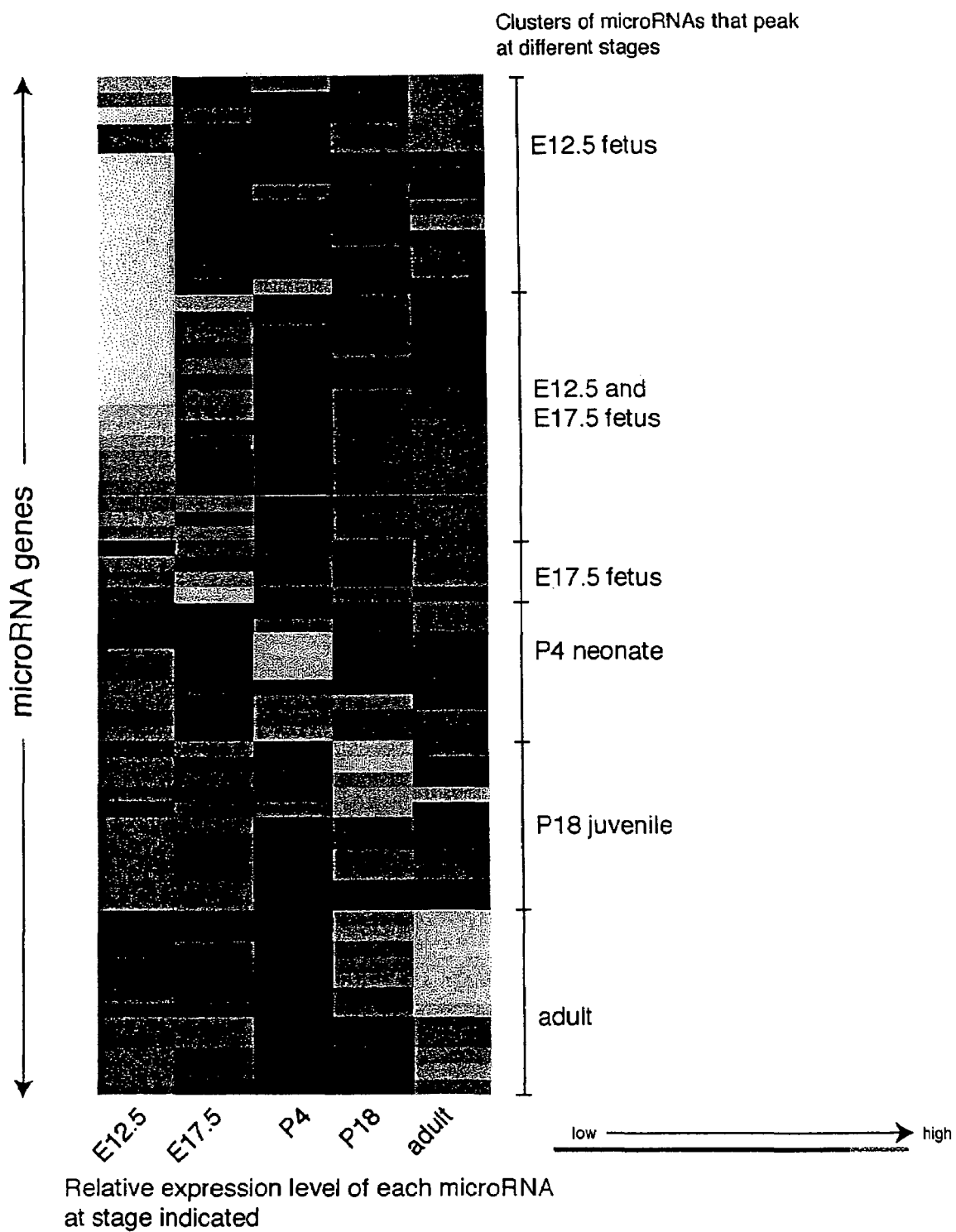
FIG. 7A shows the profile of microRNA expression in the developing mouse brain. Relative expression levels are shown for the 66 microRNAs that changed significantly (ANOVA, P<0.001) (i.e., more than two-fold) are shown in five columns corresponding to the five developmental time points. The gray scale at the bottom indicates relative signal intensities. The microRNA expression profile was sorted using a hierarchical clustering method, and major clusters are shown ordered according to the time that expression peaks. Gene names and a quantitative description of microRNA expression levels are presented in Table 2.
Figure 7B:
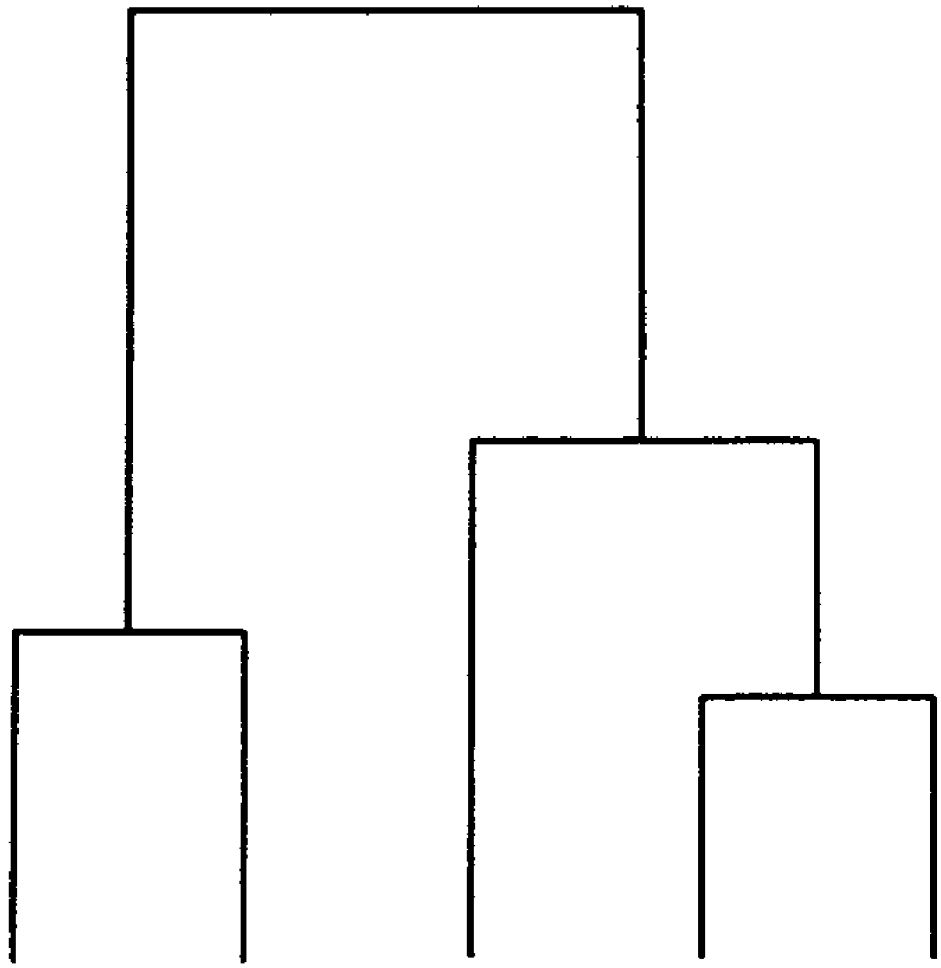
FIG. 7B shows developmental time points grouped using the same hierarchical clustering method and gene set as shown in FIG. 7A.

We grouped microRNAs that changed more than two-fold in expression during the period analyzed using a hierarchical clustering algorithm (FIGS. 7A and 8A) (Eisen *Proc Natl Acad Sci USA* 95:14863-14868, 1998). Hierarchical clustering methods organize data in a tree structure, based on similarity (FIG. 7B). A group of microRNAs peaked at each of the developmental timepoints. The signal from thirty-four of the sixty-six probes that changed more than two-fold peaked in the fetus (E12.5 and E17.5), suggested that these microRNAs function in early development (FIG. 4A). Nine microRNAs peaked in expression level during the neonate (P4) stage, while eleven other microRNAs peaked at the juvenile (P18) stage. Twelve microRNAs were expressed at their highest level at the adult stage (FIG. 8B). These data indicate that murine brain development involves a wave of expression of sequential classes of microRNAs (FIG. 7A).

We also grouped the developmental timepoints according to their microRNA expression pattern using hierarchical clustering. We found that samples from stages that are developmentally proximal had the most similar microRNA expression patterns (FIG. 7B), indicating that a microRNA expression profile can be a marker of developmental stage. Examination of temporal clusters revealed that probes with similar sequences showed correlated expression, as exemplified by miR-181a, miR-181b, miR-181 c, smallRNA-12 as shown in FIG. 8A and further exemplified by miR-29a, miR-29b and miR-29c as shown in FIG. 8B, respectively. We found that four (smallRNA-2 5'-TGGTGTCAGAAGTGG-GATAC-3'(SEQ ID NO:1); smallRNA-12 5'-ACTCAC-CGAGAGCGTTGAATGTT-3'(SEQ ID NO:2); let-7h 5'-AACTGTACACACTACTACCTCA-3'(SEQ ID NO:3); miR-33b 5'-CAATGCAACAGCAATGCAC-3'(SEQ ID NO:4)) of the sixty-six RNAs that changed more than two-fold were small RNAs rather than microRNAs. The temporal regulation of these small RNAs indicated that they are likely to function in development.

Validation of Microarray Results Using Northern Blots

Figure 9:
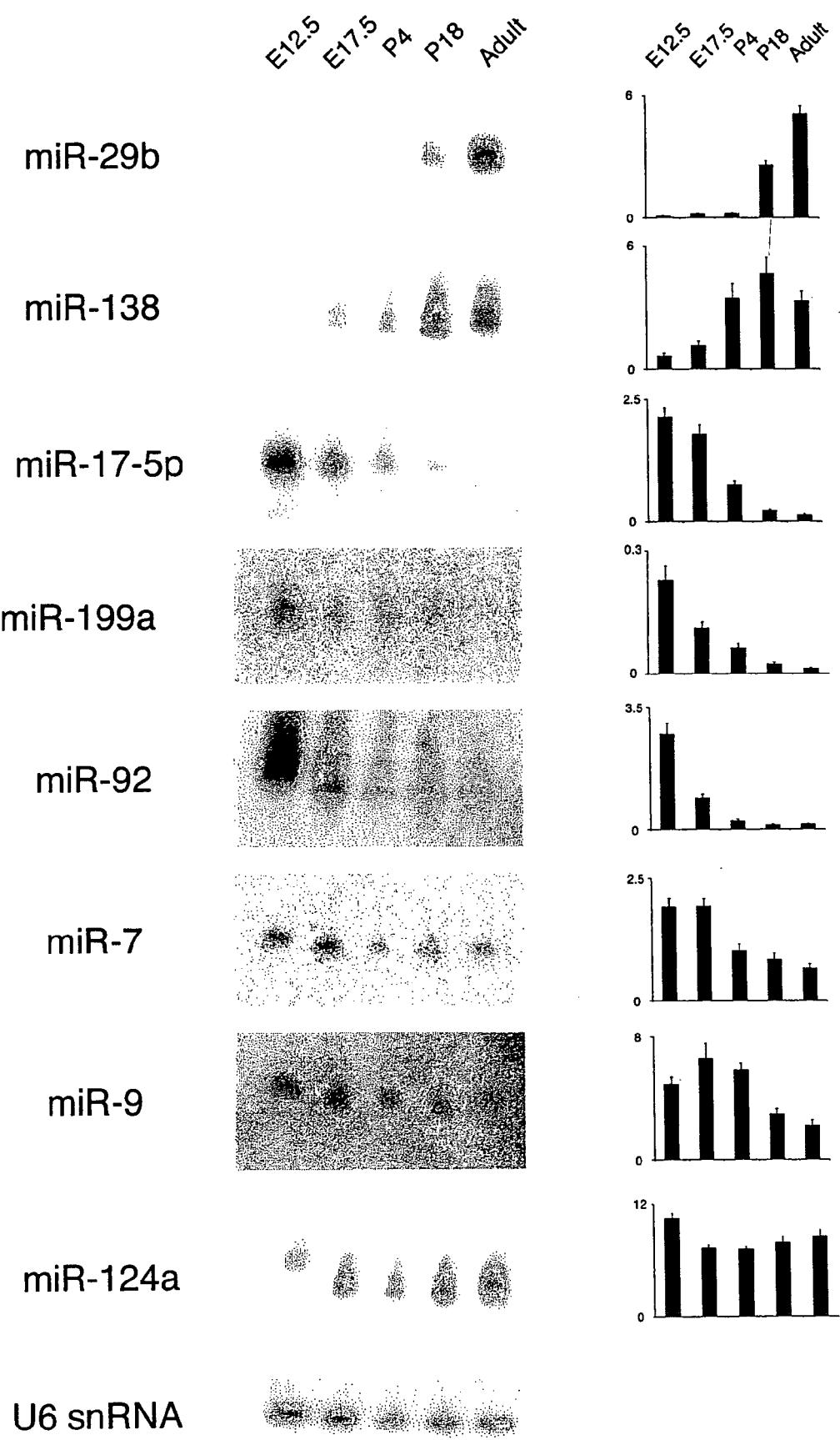
FIG. 9 shows a side-by-side comparison of microarray hybridization signal data (right panel) with representative developmental northern blots of microRNAs (left panel). Northern blots were prepared and microarray analysis was done using the same starting material. Y-axis for the microarray data refers to the averaged mean signal intensities ($\times 10^{-3}$), and error bars are standard errors of the mean. Since northern blots were exposed for different lengths of time, the intensities of the signals on northern blots cannot be directly compared to those from the microarrays. A probe against U6 snRNA was hybridized to the same blots as a control to ensure that the wells were evenly loaded.

To validate our microarry results, we performed northern blots of eight microRNAs that were robustly expressed during at least at one point during development according to our microarray data (FIG. 9). The relative change in microRNA expression as determined using microarray analysis and northern blot analysis was consistent (FIG. 9). For example, for both microarray and northern blot analysis indicated that miR-29b was almost undetectable at the embryonic and P4 stages; expression became detectable at P18, and the microRNA was strongly expressed in the adult. In only a few cases did there seem to be discrepancies between microarray and northern blot analysis; for example, there were small differences in the relative levels of expression of miR-138 at P4 and adult stages differed between northern blot and microarray analysis. Microarrays offer a high-throughput method that provides for the analysis of microRNA expression patterns.

The development of microarray technology for profiling the expression of microRNAs and other small RNAs is described herein and a working example is provided that shows the results of applying this technology to the developing mammalian brain. Recently, Krichevsky et al. described the temporal expression of 44 microRNAs during mouse brain development (Krichevsky et al., *RNA*, 9:1274-1281, 2003). The Krichevsky study used a dot-blot array approach and required the direct radioactive labeling of individual microRNAs. In contrast, our approach used a glass microarray and RT-PCR/fluorescent labeling. Despite differences in sample selection as well as in the number of microRNAs analyzed, where the two studies overlap, the data analyses typically agree. Thus, our strategy, which is demonstrably no less sensitive than that of Krichevsky, offers two significant advantages that Krichevsky's techniques does not; it is highly scalable and allows for the high-throughput analysis of even small biological samples.

As described herein, microRNA microarrays offer a new tool that provides for the analysis of microRNAs. It is likely that many of the developmentally regulated microRNAs described herein function in the control of mammalian brain development, possibly by controlling developmental timing, analogous to the roles of the lin-4 and let-7 microRNAs in *C. elegans*.

The results described above were carried out using the following methods.

microRNA Cloning

We isolated RNAs and cloned microRNAs from *R. norvegicus* and *M. mulatta* using methods described previously (Lagos-Quintana et al., *Science* 294:853-858, 2001) except that the samples were not dephosphorylated during the cloning procedure.

Microarray Printing and Hybridization

Microarray probes were oligonucleotides (identified herein as EAM followed by a number) having sequences that are complementary to microRNAs. Each probe was modified with a free amino group linked to its 5' terminus through a 6-carbon spacer (IDT) and was printed onto an amine-binding slide (CodeLink, Amersham Biosciences Little Chalfont, UK). Control probes contained two internal mismatches resulting in either C-to-G or T-to-A changes. The sequences of the control and microarray probes (SEQ ID NOS:5-219) are shown in Table 2, which also provides a summary of the microarray data. The sequences of Table 2, along with their names and sequence identifiers, are shown in Table 3.

| Oligo ID | Oligo sequence | Small RNA (Rfam 3.0) | A B C | Oligo length | Tm (NN) | E12.5 | E12.5 SEM | E17.5 | E17.5 SEM | P4 | P4 SEM | P18 | P18 SEM | Adult | Adult SEM |
|---|---|---|---|---|---|---|---|---|---|---|---|---|---|---|---|
| EAM101 | TCCATCATCAAAACAAAATGGAGT | mmu-miR-136 | --- | 23 | 67.9 | 2,566.6 | 553.8 | 3,099.4 | 492.7 | 5,478.9 | 486.3 | 5,422.4 | 438.2 | 2,195.1 | 271.8 |
| EAM102 | TCCATCATGAAAAGAAAATGGAGT | control | --- | 23 | 67.3 | 208.0 | 21.8 | 306.0 | 19.7 | 495.5 | 31.6 | 457.3 | 82.9 | 213.9 | 45.4 |
| EAM103 | TGGCATTCACCGCGTGCCTTA | mmu-miR-124a | +++ | 21 | 78.1 | 10,479.0 | 554.2 | 7,301.8 | 350.5 | 7,185.7 | 296.3 | 7,921.3 | 595.8 | 8,544.7 | 716.9 |
| EAM104 | TGGCATTCAGCGGGTGCCTTA | control | --- | 21 | 77.2 | 6,552.3 | 677.5 | 4,992.1 | 223.8 | 5,475.9 | 272.2 | 5,481.6 | 467.6 | 5,419.0 | 332.1 |
| EAM105 | TCACAAGTTAGGGTGTCAGGGA | mmu-miR-125b | +++ | 22 | 67.8 | 4,367.2 | 445.3 | 6,279.3 | 280.8 | 4,884.0 | 464.5 | 3,123.8 | 274.0 | 3,238.3 | 399.4 |
| EAM106 | TCACAAGTAAGGTGTCAGGGA | control | --- | 22 | 68.5 | 2,203.5 | 163.3 | 3,310.7 | 134.6 | 2,250.2 | 111.4 | 1,400.7 | 145.9 | 1,456.1 | 141.5 |
| EAM107 | TGTTCCTGCTGACTGAGCCA | mmu-miR-24 | --- | 21 | 70.4 | 748.7 | 104.7 | 715.9 | 87.5 | 550.8 | 92.7 | 1,061.9 | 220.2 | 1,887.1 | 239.1 |
| EAM108 | TGTTCCTGGTGAAGTGAGCCA | control | --- | 21 | 70.1 | 546.4 | 57.9 | 528.4 | 71.1 | 556.9 | 54.4 | 869.5 | 107.4 | 1,345.8 | 140.0 |
| EAM109 | AACAACAAAATCACTAGTCTTCCA | mmu-miR-7 | +++ | 24 | 64.9 | 1,917.8 | 181.4 | 1,929.6 | 162.9 | 1,020.1 | 131.5 | 837.8 | 128.0 | 666.0 | 80.7 |
| EAM110 | AACCACAAAATGAGTAGTCTTCCA | control | --- | 24 | 64.9 | 793.5 | 86.8 | 701.8 | 105.0 | 489.1 | 49.7 | 330.4 | 45.9 | 266.5 | 31.4 |
| EAM1100 | GCATGCATGCATGCATGCATG | control | --- | 21 | 76.1 | -0.5 | 0.1 | 0.0 | 0.1 | -0.3 | 0.1 | -0.1 | 0.1 | 0.3 | 0.2 |
| EAM1101 | GTGGTAGCGCAGTGCGTAGAA | control | --- | 21 | 70.5 | 0.3 | 0.1 | 0.4 | 0.1 | 0.1 | 0.1 | 0.3 | 0.1 | 1.2 | 0.4 |
| EAM1102 | GGTGATGCCCTGAATGTTGTC | control | --- | 21 | 68.9 | 0.2 | 0.2 | 0.3 | 0.1 | 0.3 | 0.1 | 0.2 | 0.1 | 0.2 | 0.1 |
| EAM1103 | TGTCATGGATGACCTTGGCCA | control | --- | 21 | 73.0 | 0.3 | 0.1 | 0.5 | 0.1 | 0.1 | 0.1 | -0.8 | 0.2 | -0.5 | 0.1 |
| EAM1104 | CTTTTGACATTGAAGGAGCT | control | --- | 21 | 65.5 | 1.0 | 0.4 | 0.4 | 0.1 | 0.4 | 0.1 | 0.3 | 0.1 | 0.3 | 0.0 |
| EAM111 | TAACTGTACAAACTACTACCTCA | mmu-let-7g | +++ | 23 | 56.4 | 1,585.3 | 124.9 | 2,631.4 | 163.8 | 2,519.8 | 324.0 | 2,208.7 | 222.5 | 2,944.3 | 244.0 |
| EAM112 | TAACTGTAGAAAGTACTACCTCA | control | --- | 23 | 55.9 | 18.6 | 3.4 | 42.2 | 8.5 | 37.5 | 7.7 | 31.6 | 8.4 | 49.2 | 7.8 |
| EAM113 | ACAGGTAAAAGGGTCTCAGGGA | mmu-miR-125a | +++ | 22 | 68.7 | 1,916.1 | 253.8 | 2,181.2 | 307.8 | 2,051.8 | 453.0 | 1,394.4 | 263.3 | 2,751.5 | 445.9 |
| EAM114 | ACAGGTAAAAGGGTGTCAGGGA | control | --- | 22 | 69.3 | 852.4 | 94.9 | 965.0 | 99.9 | 592.0 | 65.6 | 609.5 | 61.3 | 1,396.0 | 109.5 |
| EAM115 | CGCCAATATTTACGTGCTGCTA | mmu-miR-16 | +++ | 22 | 70.2 | 1,273.8 | 134.0 | 1,571.9 | 300.7 | 1,398.5 | 286.0 | 910.3 | 186.0 | 995.4 | 149.3 |
| EAM116 | CGCCAATATTAAGGTGCTGCTA | control | --- | 22 | 69.5 | 872.5 | 115.7 | 1,009.6 | 136.8 | 696.3 | 80.6 | 416.9 | 48.0 | 281.0 | 27.9 |
| EAM117 | TAACCGATTTCAAATGGTGCTA | mmu-miR-29c | +++ | 22 | 67.2 | 154.4 | 40.6 | 292.8 | 60.6 | 949.9 | 312.6 | 3,313.3 | 290.1 | 5,406.9 | 146.4 |
| EAM118 | TAACCGATTTGAAAGGTGCTA | control | --- | 22 | 66.7 | 4.8 | 0.9 | 4.5 | 0.6 | 2.2 | 0.7 | 28.5 | 8.8 | 103.3 | 31.9 |
| EAM119 | AACACTGATTTCAAATGTGCTA | mmu-miR-29b | +++ | 23 | 66.2 | 115.9 | 16.9 | 204.1 | 29.5 | 227.1 | 35.0 | 2,617.0 | 203.4 | 5,125.9 | 373.6 |

-continued

| Oligo ID | Oligo sequence | Small RNA (Rfam 3.0) | A B C | Oligo length | Tm (NN) | E12.5 | E12.5 SEM | E17.5 | E17.5 SEM | P4 | P4 SEM | P18 | P18 SEM | Adult | Adult SEM |
|---|---|---|---|---|---|---|---|---|---|---|---|---|---|---|---|
| EAM120 | AACACTGATTTGAAAAGGTGCTA | control | --- | 23 | 65.7 | 18.3 | 3.8 | 22.5 | 3.9 | 80.4 | 10.3 | 655.0 | 80.4 | 1,225.8 | 77.3 |
| EAM121 | CACAAGATCGGATCGTACGGGT | mmu-miR-99a | +++ | 21 | 68.0 | 3,074.1 | 472.8 | 4,504.2 | 497.3 | 2,168.9 | 238.9 | 1,207.4 | 131.0 | 607.1 | 88.1 |
| EAM122 | CACAAGATGGGATGTACGGGT | control | --- | 21 | 68.5 | 775.9 | 51.0 | 1,115.3 | 76.8 | 720.3 | 37.6 | 429.6 | 32.6 | 240.1 | 34.5 |
| EAM123 | AACTATGCAACTACTACCTCT | mmu-let-7d | --- | 22 | 59.4 | 4,723.1 | 330.2 | 4,694.2 | 353.2 | 4,971.2 | 500.8 | 5,081.4 | 529.3 | 6,340.0 | 327.6 |
| EAM124 | AACTATGCAACGTAGTACCTCT | control | --- | 22 | 60.1 | 500.3 | 82.7 | 1,040.7 | 93.3 | 1,438.5 | 116.9 | 1,531.2 | 131.4 | 1,650.9 | 153.2 |
| EAM125 | CGGCCTGATTCACAACACCAGCT | mmu-miR-138 | --- | 23 | 77.2 | 643.0 | 143.6 | 1,170.0 | 201.3 | 3,454.0 | 688.3 | 4,646.7 | 785.8 | 3,313.7 | 477.1 |
| EAM126 | CGGCCTGATTGAGAACACCAGCT | control | --- | 23 | 76.6 | 448.2 | 83.9 | 808.9 | 115.4 | 1,733.3 | 254.2 | 2,227.5 | 289.2 | 1,450.0 | 182.6 |
| EAM127 | TCATAGCCCTGTACAATGCTGCT | mmu-miR-103 | --- | 23 | 70.8 | 1,163.8 | 181.0 | 1,531.3 | 265.1 | 1,663.4 | 442.6 | 1,492.5 | 337.1 | 932.0 | 188.7 |
| EAM128 | TCATAGCCCTGAAGAATGCTGCT | control | --- | 23 | 72.3 | 904.3 | 155.8 | 875.6 | 126.5 | 651.2 | 88.5 | 900.0 | 119.2 | 448.3 | 84.5 |
| EAM129 | AGGCATTCACCGCGTGCCTTAT | mmu-miR-124a | --- | 22 | 76.8 | 11,594.7 | 1,000.9 | 8,352.1 | 590.8 | 10,020.2 | 561.9 | 9,323.5 | 715.1 | 10,618.3 | 1,171.4 |
| EAM130 | AGGCATTCAGCGGGTGCCTTAT | control | --- | 22 | 76.0 | 7,004.6 | 938.7 | 5,699.5 | 450.9 | 6,117.8 | 553.5 | 5,927.1 | 421.3 | 8,189.1 | 788.6 |
| EAM131 | ACAGGCCCGGACAAGTGCAATAT | mmu-miR-92 | +++ | 23 | 75.9 | 2,733.4 | 317.5 | 893.1 | 110.5 | 255.5 | 49.9 | 126.8 | 21.9 | 142.2 | 26.1 |
| EAM132 | ACAGGCCGGGAGAAGAGACAATAT | control | --- | 23 | 74.6 | 800.4 | 64.5 | 186.9 | 39.4 | 72.9 | 11.1 | 37.7 | 7.9 | 54.3 | 6.4 |
| EAM133 | ACACCAATGCCCTAGGGGATGCG | mmu-miR-324-5p | +++ | 23 | 80.0 | 286.4 | 40.8 | 222.0 | 31.5 | 161.7 | 27.1 | 114.4 | 20.6 | 101.7 | 17.3 |
| EAM134 | ACACCAATGGCGTAGGGGATGCG | control | +++ | 23 | 80.8 | 177.7 | 21.4 | 187.6 | 26.9 | 167.9 | 34.5 | 168.6 | 28.8 | 93.2 | 15.0 |
| EAM135 | CAACAAAACATTTAATGAGCC | mmu-miR-B | +++ | 21 | 64.4 | -0.6 | 0.2 | 0.9 | 0.4 | -1.4 | 0.2 | 2.1 | 1.7 | 3.4 | 1.4 |
| EAM136 | CAACAAAGATTAAATGAGCC | control | --- | 21 | 63.8 | 3.5 | 0.4 | 2.6 | 0.3 | 3.3 | 0.5 | 2.9 | 0.5 | 5.2 | 0.6 |
| EAM137 | CCGACCATGGCTGTAGACTGTTA | mmu-miR-132 | +++ | 23 | 70.9 | 16.6 | 5.0 | 54.7 | 14.7 | 102.3 | 32.7 | 280.1 | 59.4 | 808.3 | 146.9 |
| EAM138 | CCGACCATGGTGAAGACTGTTA | control | +++ | 23 | 72.8 | 14.0 | 5.0 | 43.1 | 10.1 | 31.8 | 9.7 | 193.8 | 50.2 | 438.2 | 78.8 |
| EAM139 | TAACCCATGGAATTCAGTTCTCA | mmu-miR-146 | +++ | 23 | 68.1 | 419.7 | 88.1 | 662.1 | 145.6 | 1,703.2 | 518.6 | 1,612.3 | 341.4 | 669.9 | 162.1 |
| EAM140 | TAACCCATGGAAATGAGTTCTCA | control | --- | 23 | 68.1 | 1.3 | 0.3 | 0.9 | 0.1 | 0.8 | 0.1 | 3.1 | 0.9 | 1.3 | 0.4 |
| EAM141 | TAACTATCAATCTACTACCTCA | mmu-let-7f | --- | 23 | 53.6 | 3,685.7 | 347.4 | 3,918.5 | 372.9 | 4,705.6 | 333.1 | 3,671.1 | 176.2 | 4,305.7 | 239.8 |
| EAM142 | TAACTATCAATGTAGTACCTCA | control | --- | 23 | 54.2 | 1.7 | 1.5 | 4.8 | 2.3 | 7.1 | 3.4 | 8.4 | 4.3 | 12.1 | 4.6 |
| EAM143 | TAACCATCAACCTATTACCTCA | smallRNA-9 | +-- | 23 | 61.2 | 4,624.5 | 272.5 | 6,065.4 | 573.7 | 5,549.0 | 508.8 | 5,381.2 | 456.6 | 5,382.2 | 351.1 |

-continued

| Oligo ID | Oligo sequence | Small RNA (Rfam 3.0) | A B C | Oligo length | Tm (NN) | E12.5 | E12.5 SEM | E17.5 | E17.5 SEM | P4 | P4 SEM | P18 | P18 SEM | Adult | Adult SEM |
|---|---|---|---|---|---|---|---|---|---|---|---|---|---|---|---|
| EAM144 | TAACCATAGAACGTATTACCTCA | control | - - - | 23 | 61.4 | 1.1 | 0.2 | 2.1 | 0.5 | 1.9 | 0.5 | 1.3 | 0.4 | 1.5 | 0.3 |
| EAM145 | AACCATACAACCTACTACCTCA | mmu-let-7c | +++ | 22 | 60.3 | 7,443.7 | 624.0 | 7,035.7 | 1,002.3 | 7,055.3 | 882.9 | 7,347.4 | 925.7 | 8,854.7 | 641.2 |
| EAM146 | AACCATACAACCTAGTACCTCA | control | - - - | 22 | 60.7 | 2,914.2 | 332.1 | 3,841.4 | 333.9 | 4,215.1 | 458.8 | 3,283.2 | 258.1 | 3,696.1 | 171.0 |
| EAM147 | AACCACACAACCTACTACCTCA | mmu-let-7b | +++ | 22 | 63.1 | 6,198.0 | 466.8 | 7,186.7 | 856.7 | 5,764.8 | 594.8 | 7,353.0 | 1,059.8 | 7,098.9 | 417.2 |
| EAM148 | AACCACACAAGCTAGTACCTCA | control | - - - | 22 | 63.5 | 2,334.0 | 238.0 | 3,909.2 | 307.2 | 4,671.7 | 587.2 | 4,016.0 | 371.7 | 4,336.3 | 208.3 |
| EAM149II | GCATTCACCCGCGTGCCTTA | mir-124b# | + - - | 20 | 75.4 | 11,150.9 | 1,375.8 | 6,018.1 | 1,009.9 | 7,196.2 | 1,151.7 | 6,949.5 | 1,326.9 | 7,285.2 | 1,404.3 |
| EAM150II | TCATACAGCTAGATAACCAAAGA | mmu-miR-9 | + - - | 23 | 61.4 | 4,877.7 | 482.6 | 6,556.2 | 983.2 | 5,796.1 | 459.3 | 2,967.1 | 341.2 | 2,211.1 | 354.7 |
| EAM151 | ACAAGATCGGATCTACGG | mmu-miR-99a | + - - | 18 | 58.6 | 1,886.8 | 349.5 | 2,625.7 | 292.1 | 2,289.9 | 380.0 | 1,520.5 | 294.5 | 313.5 | 41.1 |
| EAM152 | ACTTTCGGTTATCTAGCTTTAT | mmu-miR-9* | +++ | 22 | 59.7 | 687.9 | 146.6 | 651.2 | 110.6 | 1,279.9 | 168.1 | 300.0 | 45.9 | 214.3 | 40.2 |
| EAM153 | AACTATACAACCTACTACCTCA | mmu-let-7a | +++ | 22 | 55.2 | 8,098.5 | 741.1 | 6,883.1 | 447.6 | 7,513.1 | 446.0 | 7,661.8 | 535.1 | 8,165.0 | 730.7 |
| EAM154 | AAAGAGACCGGTTCACTGTGA | mmu-miR-128b | - - - | 21 | 66.0 | 2,017.8 | 395.2 | 5,627.3 | 631.1 | 6,962.5 | 253.6 | 6,732.5 | 523.4 | 7,150.9 | 570.7 |
| EAM155 | TCCATCATCAAAACAAATGGAGT | mmu-miR-136 | +++ | 23 | 67.9 | 2,428.6 | 268.3 | 3,319.0 | 191.5 | 3,849.1 | 262.1 | 4,409.4 | 231.9 | 2,022.0 | 205.2 |
| EAM156 | ACTCACCGAGAGCGTTGAATGTT | smallRNA-12 | + - - | 23 | 71.9 | 4,086.4 | 267.5 | 3,199.8 | 243.6 | 2,266.9 | 110.5 | 1,714.3 | 126.9 | 1,748.9 | 225.4 |
| EAM157 | TGGTGTCAGAAGTGGGATAC | smallRNA-2 | + - - | 20 | 61.3 | 246.6 | 46.6 | 183.7 | 30.4 | 82.1 | 13.5 | 61.2 | 12.8 | 35.8 | 6.5 |
| EAM158 | TACAGCTAAATAACCAAAGA | smallRNA-13 | + - - | 20 | 54.9 | 290.2 | 78.7 | 341.3 | 112.2 | 228.8 | 59.6 | 98.3 | 39.6 | 114.7 | 34.1 |
| EAM159 | ATGCCCTTTTAACATTGCACTG | mmu-miR-130a | +++ | 22 | 68.9 | 2,204.4 | 177.6 | 1,392.2 | 154.2 | 877.8 | 111.2 | 571.8 | 76.9 | 209.0 | 36.6 |
| EAM160 | AACCTATCCTGAATTACTTGAA | mmu-miR-26b | +++ | 22 | 60.1 | 1,452.0 | 212.1 | 2,227.8 | 311.0 | 2,037.4 | 180.4 | 2,099.7 | 139.0 | 1,033.1 | 105.2 |
| EAM161 | CTCAATAGACTGTGAGCTCCTT | mmu-miR-28 | +++ | 22 | 62.3 | 109.2 | 14.8 | 115.9 | 19.6 | 144.8 | 30.8 | 128.3 | 21.4 | 142.6 | 18.4 |
| EAM162 | ATCAAGGTCCGCTGTGAACACG | [mmu-miR-124a-as] | +++ | 22 | 73.7 | 116.5 | 25.9 | 112.0 | 22.1 | 66.1 | 12.6 | 53.9 | 16.7 | 46.2 | 12.4 |
| EAM163 | TCCATAAAGTAGGAAAACACTACA | mmu-miR-142-3p | +++ | 23 | 61.1 | 196.0 | 39.4 | 288.9 | 40.4 | 249.1 | 58.3 | 197.8 | 28.6 | 49.1 | 7.5 |
| EAM164 | GAGTGCTTGCTAGGTGCCAAG | smallRNA-3 | + - - | 21 | 69.2 | 1.6 | 0.7 | 0.1 | 0.4 | 0.9 | 0.7 | -0.7 | 0.4 | -0.2 | 0.1 |
| EAM165 | GGGAGTGAAGACACGGAGCCAGA | mmu-miR-149 | - - - | 23 | 76.4 | 489.7 | 76.4 | 387.2 | 85.9 | 386.8 | 80.9 | 222.0 | 49.6 | 115.1 | 24.8 |
| EAM166 | GCCTATCCTGGATTACTTGAA | mmu-miR-26a | +++ | 21 | 63.2 | 1,215.2 | 188.9 | 1,977.5 | 200.7 | 2,120.3 | 174.4 | 1,818.8 | 215.7 | 1,896.3 | 186.9 |
| EAM167 | GTTGTGGTCACTTACAATT | smallRNA-4 | + - - | 19 | 53.1 | 0.2 | 0.1 | 0.2 | 0.1 | 0.3 | 0.1 | 0.2 | 0.1 | 0.5 | 0.1 |

-continued

| Oligo ID | Oligo sequence | Small RNA (Rfam 3.0) | A B C | Oligo length | Tm (NN) | E12.5 | E12.5 SEM | E17.5 | E17.5 SEM | P4 | P4 SEM | P18 | P18 SEM | Adult | Adult SEM |
|---|---|---|---|---|---|---|---|---|---|---|---|---|---|---|---|
| EAM168 | CTATACAACCTCCTACCTCA | mmu-let-7e | +++ | 20 | 55.6 | 3,703.9 | 535.7 | 4,698.0 | 249.3 | 4,131.1 | 249.1 | 3,888.9 | 225.2 | 3,182.2 | 262.8 |
| EAM169 | AACAGCACAAACTACTACCTCA | mmu-let-7i | --- | 22 | 61.3 | 1,490.2 | 160.9 | 2,264.8 | 169.9 | 2,423.1 | 186.1 | 1,935.7 | 144.0 | 2,334.3 | 140.5 |
| EAM170 | TGGCATTCACCGCCGTGCCTTA | smallRNA-11 | +-- | 22 | 81.2 | 14,248.4 | 1,981.3 | 9,624.9 | 713.6 | 10,313.7 | 1,182.8 | 10,918.3 | 1,667.3 | 10,835.0 | 1,271.0 |
| EAM171 | CTACGGTATTCTTAAGCAATAA | mmu-miR-137 | +++ | 23 | 64.5 | 1,447.0 | 203.0 | 2,838.4 | 353.2 | 2,888.5 | 362.3 | 2,198.6 | 173.6 | 980.1 | 149.5 |
| EAM172 | CTCGTACTGAGCAGGATTA | smallRNA-5 | +-- | 19 | 56.9 | 44.0 | 4.5 | 46.8 | 8.0 | 12.3 | 1.7 | 3.2 | 0.7 | 14.5 | 1.7 |
| EAM173 | GTCTCGAAAAGGTAGCGTTC | smallRNA-6 | +-- | 20 | 63.4 | 0.4 | 0.1 | 0.2 | 0.1 | 0.1 | 0.1 | 0.1 | 0.1 | 0.6 | 0.2 |
| EAM174 | AGAAAACATGCTCCAGGTGA | smallRNA-1 | +-- | 20 | 64.2 | 871.5 | 197.4 | 1,340.2 | 391.0 | 916.4 | 181.3 | 583.7 | 203.8 | 47.4 | 15.6 |
| EAM175 | TCGCCCTCTCAACCCAGCTTTT | mmu-miR-320 | +++ | 22 | 76.2 | 1,486.0 | 215.2 | 699.9 | 134.9 | 600.1 | 174.5 | 456.5 | 83.1 | 184.9 | 22.5 |
| EAM176 | TACAGTACTGTGATAGCTGAA | smallRNA-10 | +-- | 21 | 54.5 | 20.2 | 2.0 | 18.8 | 1.4 | 26.3 | 2.0 | 12.3 | 1.3 | 9.6 | 0.8 |
| EAM177 | TTCAGCTATCACAGTACTGTA | mmu-miR-101b | +++ | 21 | 54.5 | 192.3 | 46.0 | 200.3 | 30.2 | 535.9 | 155.0 | 373.1 | 85.0 | 134.7 | 18.8 |
| EAM178 | TGCCAATATTTCTGTGCTGCTA | mmu-miR-195 | --- | 22 | 68.1 | 1,033.9 | 229.1 | 1,350.1 | 227.0 | 896.1 | 165.8 | 788.6 | 107.8 | 407.7 | 79.7 |
| EAM179 | ACTATGCAACCTACTACCTCT | mmu-let-7d | +++ | 21 | 57.0 | 4,055.1 | 310.6 | 4,266.3 | 260.2 | 4,631.8 | 420.4 | 4,720.1 | 316.9 | 4,959.5 | 189.5 |
| EAM180 | AACTATACAATCTACTACCTCA | mmu-let-7f | --- | 22 | 52.7 | 3,352.8 | 273.7 | 4,133.0 | 135.2 | 4,959.5 | 440.1 | 4,070.1 | 267.0 | 5,438.6 | 145.6 |
| EAM181 | AACTGTACACACTACTACCTCA | mmu-let-7f | +++ | 22 | 52.7 | 3,368.5 | 284.6 | 3,732.8 | 323.2 | 3,508.9 | 326.6 | 2,856.4 | 235.0 | 3,964.3 | 116.9 |
| EAM182 | AGCACAAAACTACTACCTCA | let-7h# | +-- | 22 | 55.5 | 501.5 | 33.4 | 1,100.7 | 111.9 | 1,427.3 | 90.8 | 1,236.7 | 138.6 | 1,493.0 | 123.4 |
| EAM183 | AGCACAAACTACTACCTCA | mmu-let-7i | +++ | 19 | 53.4 | 712.3 | 154.3 | 1,057.2 | 145.6 | 1,355.0 | 175.8 | 1,278.7 | 175.4 | 1,255.4 | 182.0 |
| EAM184 | CACAAGTTCGGATCTACGGGTT | mmu-miR-100 | +++ | 22 | 69.9 | 2,064.9 | 179.2 | 3,752.3 | 358.9 | 2,369.2 | 159.6 | 1,721.4 | 151.9 | 529.1 | 70.9 |
| EAM185 | TCATAGCCCTGTCAATGCTGCT | mmu-miR-103 | +++ | 22 | 70.8 | 678.7 | 71.9 | 726.4 | 126.1 | 930.6 | 189.4 | 700.0 | 87.1 | 348.2 | 37.1 |
| EAM186 | GCTACCTGCACTGTAAGCACTTTT | hsa-miR-106a | ++- | 24 | 69.5 | 2,295.8 | 374.7 | 1,801.8 | 258.6 | 850.3 | 131.6 | 309.4 | 29.4 | 72.0 | 13.3 |
| EAM187 | TGATAGCCCTGTACAATGCTGCT | mmu-miR-107 | +++ | 23 | 70.8 | 653.4 | 87.6 | 626.4 | 109.5 | 1,589.6 | 429.9 | 1,156.6 | 210.2 | 316.4 | 74.2 |
| EAM188 | AATGCCCCTAAAAATCTTAT | mir-108& | +-- | 21 | 64.2 | 3.2 | 0.7 | 3.2 | 0.8 | 3.7 | 1.0 | 2.7 | 0.6 | 4.3 | 1.3 |
| EAM189 | CACAAATTCGGATCTACAGGGTA | mmu-miR-10a | +++ | 23 | 68.0 | 169.3 | 28.2 | 244.4 | 25.4 | 251.9 | 72.6 | 117.0 | 13.8 | 33.7 | 3.9 |
| EAM190 | ACAAATTCGGTTCTACAGGGTA | hsa-miR-10b | ++- | 22 | 65.3 | 18.9 | 3.9 | 372.6 | 121.9 | 115.2 | 23.6 | 55.6 | 15.1 | 6.9 | 1.9 |
| EAM191 | ACAAACACCATTGTCACACTCCA | mmu-miR-122a | +++ | 23 | 69.1 | 20.6 | 3.4 | 26.7 | 3.7 | 52.5 | 9.9 | 34.3 | 5.8 | 19.3 | 3.4 |

-continued

| Oligo ID | Oligo sequence | Small RNA (Rfam 3.0) | A B C | Oligo length | Tm (NN) | E12.5 | E12.5 SEM | E17.5 | E17.5 SEM | P4 | P4 SEM | P18 | P18 SEM | Adult | Adult SEM |
|---|---|---|---|---|---|---|---|---|---|---|---|---|---|---|---|
| EAM192 | CGCGTACCAAAAGTAATAATG | mmu-miR-126* | +++ | 21 | 63.0 | 438.1 | 76.9 | 1,050.8 | 139.3 | 1,443.1 | 186.3 | 1,223.7 | 141.3 | 511.5 | 72.2 |
| EAM193 | CACAGGTTAAAGGGTCTCAGGGA | mmu-miR-125a | +++ | 23 | 71.4 | 3,668.1 | 159.5 | 3,116.3 | 211.8 | 2,407.7 | 139.4 | 2,312.6 | 157.2 | 2,991.0 | 251.2 |
| EAM194 | AAAAGAGACCGGTTCACTGTGA | mmu-miR-128a | +++ | 22 | 67.9 | 1,766.9 | 245.8 | 6,427.0 | 382.0 | 7,554.6 | 951.0 | 7,463.6 | 882.0 | 8,526.6 | 963.2 |
| EAM195 | GAAAGAGACCGGTTCACTGTGA | mmu-miR-128b | +++ | 22 | 68.2 | 1,949.8 | 146.4 | 4,456.1 | 503.4 | 5,246.5 | 596.9 | 4,917.9 | 581.0 | 6,067.3 | 385.7 |
| EAM196 | GCAGCCCAGACCGCAAAAAG | mmu-miR-129 | --- | 21 | 72.9 | 0.3 | 0.1 | 0.1 | 0.1 | 0.2 | 0.1 | 0.0 | 0.1 | 0.1 | 0.1 |
| EAM197 | GCAAGCCCAGACCGCAAAAAG | mmu-miR-129 | --- | 21 | 75.8 | 22.1 | 5.1 | 29.0 | 4.7 | 103.4 | 18.5 | 114.6 | 18.8 | 167.0 | 30.3 |
| EAM198 | GCCCTTTCATCATTGCACTG | mmu-miR-130b | +++ | 20 | 67.7 | 679.2 | 69.0 | 456.1 | 41.8 | 135.4 | 20.5 | 32.7 | 3.8 | 27.1 | 6.6 |
| EAM199 | ACGACCATGGCTGTAGACTGTT | mmu-miR-132 | --- | 23 | 68.2 | 17.9 | 4.2 | 44.5 | 8.6 | 60.7 | 8.7 | 265.0 | 45.7 | 533.7 | 83.5 |
| EAM200 | ACAGCTGGTTGAAGGGGACCAA | mmu-miR-133 | +++ | 22 | 74.5 | 4.7 | 1.1 | 11.0 | 2.3 | 10.2 | 2.4 | 23.9 | 4.6 | 55.0 | 12.1 |
| EAM201 | TAGCTGGTTGAAGGGGACCAA | miR-133b* | +-- | 21 | 71.0 | 4.9 | 1.0 | 5.4 | 0.9 | 11.0 | 1.7 | 27.0 | 4.7 | 41.4 | 9.1 |
| EAM202 | TCCCTCTGGTCAACAGTCACA | mmu-miR-134 | +++ | 22 | 71.4 | 259.7 | 46.3 | 62.1 | 7.2 | 136.8 | 22.8 | 36.0 | 5.9 | 23.0 | 4.3 |
| EAM203 | TTTCATATAGGAATAAAAAGCCATA | mmu-miR-135 | +++ | 24 | 65.7 | 816.6 | 104.5 | 885.6 | 183.3 | 530.7 | 73.4 | 263.8 | 74.7 | 159.5 | 30.9 |
| EAM204 | ATCACATAGGAATAAAAAGCCATA | mmu-miR-135 | --- | 24 | 64.9 | 1,181.3 | 167.5 | 1,086.4 | 208.4 | 759.4 | 120.7 | 239.1 | 59.2 | 141.1 | 28.8 |
| EAM205 | GATTCACAACACCAGCT | mmu-miR-138 | +++ | 17 | 52.9 | 486.9 | 79.7 | 891.1 | 137.0 | 1,702.4 | 182.5 | 3,191.6 | 317.1 | 1,836.9 | 167.5 |
| EAM206 | AGACACGTGCACTGTAGA | mmu-miR-139 | +++ | 18 | 54.0 | 55.0 | 12.3 | 19.1 | 3.0 | 56.0 | 9.3 | 189.4 | 45.4 | 313.1 | 58.1 |
| EAM207 | CTACCATAGGGTAAAACCACT | mmu-miR-140 | +++ | 21 | 60.1 | 112.9 | 22.6 | 79.0 | 12.5 | 142.3 | 29.1 | 124.5 | 22.1 | 57.5 | 8.7 |
| EAM208 | CCATCTTTACCAGACAGTGTT | mmu-miR-141 | +++ | 21 | 60.7 | 0.0 | 0.1 | -0.1 | 0.0 | 0.0 | 0.0 | 0.1 | 0.1 | 0.1 | 0.0 |
| EAM209 | GTAGTGCTTTCTACTTTATG | mmu-miR-142-5p | +++ | 20 | 51.1 | 40.8 | 8.6 | 84.4 | 15.8 | 10.0 | 2.6 | 48.1 | 11.2 | 17.2 | 4.3 |
| EAM210 | tgAGCTACAGTGCTTCATCTCA | mmu-miR-143 | +++ | 22 | 65.0 | 110.7 | 27.5 | 125.8 | 26.5 | 252.8 | 40.1 | 255.4 | 41.3 | 210.1 | 35.6 |
| EAM211 | CTAGTACATCATCTATACTGTA | mmu-miR-144 | +++ | 22 | 48.2 | 42.4 | 12.5 | 230.5 | 44.6 | 55.6 | 8.0 | 27.2 | 4.6 | 34.8 | 6.6 |
| EAM212 | AAGGGATTCCTGGGAAAACTGGAC | mmu-miR-145 | +++ | 24 | 75.1 | 164.4 | 34.3 | 196.0 | 32.2 | 121.7 | 25.1 | 186.7 | 32.3 | 324.8 | 62.4 |
| EAM213 | AAACCATGGGAATTCAGTTCTCA | mmu-miR-146 | +++ | 23 | 69.5 | 330.9 | 35.3 | 516.9 | 56.7 | 1,015.5 | 145.0 | 1,291.6 | 154.9 | 498.7 | 93.5 |
| EAM214 | ACAGTTCTGTAGTGCACTGA | mmu-miR-148a | +++ | 22 | 61.6 | 124.1 | 21.4 | 87.7 | 15.1 | 97.7 | 16.9 | 64.8 | 13.8 | 49.3 | 10.3 |
| EAM215 | ACAAAGTTCTGTGATGCACTGA | mmu-miR-148b | +++ | 22 | 64.5 | 144.9 | 24.7 | 142.6 | 18.7 | 115.2 | 15.4 | 122.7 | 28.8 | 82.9 | 14.9 |

-continued

| Oligo ID | Oligo sequence | Small RNA (Rfam 3.0) | A B C | Oligo length | Tm (NN) | E12.5 | E12.5 SEM | E17.5 | E17.5 SEM | P4 | P4 SEM | P18 | P18 SEM | Adult | Adult SEM |
|---|---|---|---|---|---|---|---|---|---|---|---|---|---|---|---|
| EAM216 | GGAGTGAAGACACGGAGCCAGA | mmu-miR-149 | +++ | 22 | 72.9 | 834.3 | 128.0 | 389.9 | 43.1 | 401.0 | 69.9 | 301.0 | 72.3 | 139.0 | 25.1 |
| EAM217 | ACACTGGTACAAGGGTTGGGAGA | mmu-miR-150 | +++ | 23 | 71.5 | 11.5 | 2.9 | 18.5 | 2.4 | 37.0 | 7.0 | 210.1 | 52.0 | 119.1 | 25.5 |
| EAM218 | CCAAGTTCTGTCATGCACTGA | mmu-miR-152 | +++ | 21 | 65.5 | 61.3 | 10.6 | 35.3 | 3.4 | 57.2 | 12.5 | 25.1 | 4.5 | 17.1 | 3.1 |
| EAM219 | TCACTTTTGTGACTATGCAA | mmu-miR-153 | +++ | 20 | 58.3 | 374.3 | 73.4 | 279.5 | 65.2 | 247.4 | 40.0 | 147.9 | 41.1 | 140.0 | 36.7 |
| EAM220 | CGAAGGCAACACGGATAACCTA | mmu-miR-154 | +++ | 22 | 71.1 | 84.3 | 45.0 | 205.9 | 63.5 | 385.0 | 63.2 | 400.0 | 90.7 | 328.0 | 79.0 |
| EAM221 | CCCCTATCACAATTAGCATTAA | mmu-miR-155 | +++ | 22 | 63.9 | 16.6 | 2.5 | 4.2 | 0.6 | 8.7 | 1.7 | 5.9 | 0.9 | 1.4 | 0.3 |
| EAM222 | CACAAAACATTATGTGCTGCTA | mmu-miR-15a | +++ | 22 | 65.8 | 942.0 | 126.5 | 932.1 | 159.8 | 484.6 | 84.8 | 276.3 | 41.2 | 202.9 | 29.0 |
| EAM223 | TGTAAACCATGATGTGCTGCTA | mmu-miR-15b | +++ | 22 | 66.0 | 1,170.9 | 162.3 | 1,266.4 | 128.1 | 414.2 | 52.1 | 246.1 | 25.0 | 250.8 | 34.9 |
| EAM224 | ACTACCTGCACTGTAAGCACTTTG | mmu-miR-17-5p | +++ | 24 | 67.8 | 2,138.3 | 185.2 | 1,787.0 | 197.1 | 742.2 | 78.9 | 226.5 | 22.9 | 131.2 | 21.5 |
| EAM225 | TATCTGCACTAGATGCACCTTA | mmu-miR-18 | +++ | 22 | 62.4 | 568.8 | 90.5 | 281.4 | 55.5 | 222.0 | 30.4 | 27.0 | 3.4 | 3.6 | 0.7 |
| EAM226 | ACTCACCGACAGCGTTGAATGTT | mmu-miR-181a | +++ | 23 | 72.6 | 6,316.3 | 471.0 | 3,108.6 | 187.9 | 2,126.0 | 193.9 | 1,769.8 | 204.9 | 1,459.2 | 175.2 |
| EAM227 | AACCCACCGACAGCAATGAATGTT | mmu-miR-181b | +++ | 24 | 75.8 | 6,484.5 | 383.1 | 2,798.8 | 281.0 | 2,081.8 | 221.8 | 1,613.1 | 196.0 | 1,137.5 | 128.1 |
| EAM228 | ACTCACCGACAGGTTGAATGTT | mmu-miR-181c | +++ | 22 | 67.6 | 3,725.6 | 443.9 | 2,234.8 | 149.4 | 1,144.0 | 181.6 | 1,084.7 | 148.7 | 924.0 | 124.3 |
| EAM229 | TGTGAGTTCTACCATTGCAAA | mmu-miR-182 | +++ | 22 | 67.4 | 34.2 | 8.4 | 11.8 | 2.1 | 18.5 | 3.6 | 53.5 | 14.5 | 61.8 | 14.8 |
| EAM230 | CAGTGAATTCTACCAGTGCCATA | mmu-miR-183 | +++ | 23 | 66.5 | 71.3 | 20.2 | 30.7 | 3.5 | 81.7 | 23.1 | 83.1 | 14.9 | 91.3 | 19.7 |
| EAM231 | CGGCTGCAACACAAGACACGA | mmu-miR-187 | +++ | 21 | 74.1 | 37.2 | 7.0 | 29.9 | 3.5 | 57.7 | 8.8 | 136.4 | 27.6 | 48.0 | 8.4 |
| EAM232 | GGCTGTCAATTCATAGGTCAG | mmu-miR-192 | +++ | 21 | 63.7 | 8.1 | 2.3 | 16.7 | 4.0 | 10.1 | 2.5 | 8.1 | 1.8 | 16.8 | 3.4 |
| EAM233 | CCCAACAACATGAAAACTACCTA | mmu-miR-196 | +++ | 22 | 64.0 | 0.9 | 0.1 | 0.3 | 0.1 | 0.3 | 0.0 | 0.3 | 0.1 | 0.2 | 0.1 |
| EAM234 | GAACAGGTAGTCTGAACACTGGG | mmu-miR-199a | +++ | 23 | 67.1 | 181.6 | 37.6 | 123.4 | 23.9 | 84.6 | 18.5 | 35.3 | 7.6 | 12.3 | 3.0 |
| EAM235 | GAACAGATAGTCTAAACACTGGG | hsa-miR-199b | ++- | 23 | 62.2 | 98.3 | 24.1 | 41.8 | 6.8 | 62.3 | 7.7 | 27.1 | 3.4 | 3.8 | 0.8 |
| EAM236 | TCAGTTTTGCATAGATTTGCACA | mmu-miR-19a | +++ | 23 | 68.0 | 1,062.4 | 192.3 | 953.5 | 170.6 | 442.8 | 73.0 | 110.1 | 16.8 | 41.5 | 10.2 |
| EAM237 | TCAGTTTTGCATGGATTTGCACA | mmu-miR-19b | +++ | 23 | 72.9 | 1,345.4 | 273.7 | 1,068.5 | 230.3 | 631.6 | 91.3 | 147.6 | 24.3 | 34.7 | 6.3 |
| EAM238 | ATACATACTTCTTTACATTCCA | mmu-miR-1 | +++ | 22 | 56.0 | 36.0 | 13.0 | 95.8 | 18.4 | 171.8 | 54.0 | 159.4 | 22.7 | 50.2 | 10.6 |
| EAM239 | ATACATACTTCTTTACATTCCA | mmu-miR-1 | --- | 22 | 56.0 | 21.5 | 6.0 | 77.8 | 20.6 | 136.2 | 40.8 | 189.5 | 34.6 | 44.8 | 7.4 |
| EAM240 | CTACCTGCACTATAAGCACTTTA | mmu-miR-20 | +++ | 23 | 61.7 | 2,300.0 | 254.6 | 831.7 | 74.1 | 446.0 | 71.4 | 107.3 | 21.7 | 54.3 | 11.3 |

-continued

| Oligo ID | Oligo sequence | Small RNA (Rfam 3.0) | A B C | Oligo length | Tm (NN) | E12.5 | E12.5 SEM | E17.5 | E17.5 SEM | P4 | P4 SEM | P18 | P18 SEM | Adult | Adult SEM |
|---|---|---|---|---|---|---|---|---|---|---|---|---|---|---|---|
| EAM241 | CTAGTGGTCCTAAACATTTCAC | mmu-miR-203 | +++ | 22 | 60.5 | 20.2 | 4.5 | 17.5 | 2.4 | 21.8 | 4.9 | 10.7 | 2.2 | 3.9 | 0.5 |
| EAM242 | AGGCATAGGATGACAAAGGGAA | mmu-miR-204 | +++ | 22 | 69.6 | 160.6 | 38.5 | 187.1 | 33.0 | 310.1 | 56.6 | 349.2 | 64.2 | 188.7 | 40.1 |
| EAM243 | CAGACTCCGGTGGAATGAAGGA | mmu-miR-205 | +++ | 22 | 72.7 | 16.1 | 3.5 | 4.4 | 0.7 | 3.9 | 0.9 | 2.7 | 0.3 | 1.5 | 0.2 |
| EAM244 | TCAACATCAGTCTGATAAGCTA | mmu-miR-21 | +++ | 22 | 59.4 | 317.1 | 73.9 | 211.1 | 48.5 | 250.8 | 32.0 | 183.6 | 32.2 | 140.4 | 34.6 |
| EAM245 | CAGCCGCTGTCACACGCACAG | mmu-miR-210 | ++- | 21 | 77.0 | 331.4 | 53.8 | 193.3 | 34.6 | 97.2 | 13.0 | 49.9 | 5.7 | 44.9 | 8.9 |
| EAM246 | AGGCGAAGGATGACAAAGGGAA | hsa-miR-211 | +++ | 22 | 73.9 | 78.1 | 21.8 | 142.6 | 26.3 | 140.1 | 21.9 | 189.3 | 45.0 | 105.7 | 24.4 |
| EAM247 | GGCCGTGACTGGAGACTGTTA | mmu-miR-212 | ++- | 21 | 68.9 | 4.9 | 0.9 | 6.4 | 1.5 | 7.9 | 1.3 | 49.0 | 11.5 | 70.3 | 17.1 |
| EAM248 | GGTACAATCAACGTCGATGGT | mmu-miR-213 | +++ | 22 | 70.3 | 280.5 | 63.2 | 181.0 | 38.4 | 244.3 | 67.7 | 100.0 | 18.6 | 33.1 | 5.2 |
| EAM249 | CTGCCTGTCGTGCCTGTGT | mmu-miR-214 | ++- | 21 | 72.4 | 231.8 | 39.5 | 27.1 | 2.6 | 7.5 | 0.6 | 5.7 | 0.8 | 2.4 | 0.3 |
| EAM250 | GTCTGTCAATTCATAGGTCAT | hsa-miR-215 | ++- | 21 | 57.6 | 12.8 | 2.7 | 9.3 | 1.1 | 14.5 | 3.5 | 14.5 | 2.7 | 9.0 | 1.4 |
| EAM251 | CACAGTTGCCAGTGAGATTA | mmu-miR-216 | ++- | 21 | 65.4 | 37.9 | 7.0 | 16.6 | 2.3 | 13.2 | 1.7 | 12.2 | 2.6 | 3.1 | 0.3 |
| EAM252 | ATCCAATCAGTTCCTGATGCAGTA | hsa-miR-217 | ++- | 24 | 69.7 | 14.5 | 3.3 | 5.1 | 0.6 | 12.9 | 2.2 | 10.4 | 2.2 | 0.3 | 0.1 |
| EAM253 | ACATGGTTAGATCAAGCACAA | mmu-miR-218 | +++ | 21 | 62.1 | 156.6 | 35.7 | 201.8 | 46.4 | 174.8 | 31.6 | 251.0 | 61.0 | 256.5 | 56.7 |
| EAM254 | AGAATTGCGTTTGGACAATCA | mmu-miR-219 | +++ | 21 | 67.3 | 808.0 | 131.8 | 374.5 | 65.2 | 259.9 | 44.2 | 1,626.7 | 187.8 | 378.0 | 76.4 |
| EAM255 | ACAGTTCTTCAACTGGCAGCTT | mmu-miR-22 | +++ | 22 | 67.6 | 187.2 | 48.4 | 187.7 | 35.4 | 489.7 | 61.1 | 528.5 | 112.3 | 567.0 | 117.9 |
| EAM256 | AAAGTGTCAGATACGGTGTGG | hsa-miR-220 | ++- | 21 | 63.9 | 0.9 | 0.2 | 0.8 | 0.2 | 0.4 | 0.2 | 0.4 | 0.0 | 0.5 | 0.1 |
| EAM257 | GAAACCCAGCAGACAATGTAGCT | mmu-miR-221 | +++ | 23 | 69.5 | 167.9 | 42.7 | 165.1 | 29.9 | 548.1 | 118.1 | 436.5 | 57.5 | 321.8 | 65.6 |
| EAM258 | GAGACCCAGTAGCCAGATGTAGCT | mmu-miR-222 | +++ | 24 | 70.3 | 12.2 | 1.6 | 14.3 | 1.2 | 63.0 | 5.8 | 128.0 | 19.5 | 43.3 | 8.4 |
| EAM259 | GGGGTATTTGACAAACTGACA | mmu-miR-223 | +++ | 21 | 64.0 | 22.7 | 4.8 | 26.4 | 5.0 | 27.0 | 3.9 | 18.7 | 3.8 | 7.2 | 1.9 |
| EAM260 | GGAAATCCCTGGCAATGTGAT | mmu-miR-23a | +++ | 21 | 70.2 | 728.6 | 185.5 | 407.2 | 76.8 | 451.0 | 101.0 | 742.4 | 117.1 | 799.5 | 118.5 |
| EAM261 | GTGGTAATCCCTGGCAATGTGAT | mmu-miR-23b | +++ | 23 | 71.8 | 383.9 | 67.5 | 377.2 | 64.9 | 286.6 | 49.7 | 730.2 | 178.5 | 780.1 | 64.6 |
| EAM262 | CTGTTCCTGCTGAACTGAGCCA | mmu-miR-24 | +++ | 22 | 71.8 | 884.8 | 169.5 | 505.3 | 74.4 | 538.2 | 94.0 | 1,248.9 | 236.4 | 1,379.9 | 246.6 |
| EAM263 | AGCCTATCCTGGATTACTTGAA | mmu-miR-26a | +++ | 22 | 64.7 | 1,684.2 | 121.7 | 1,926.5 | 151.5 | 1,894.7 | 83.0 | 1,903.1 | 204.2 | 2,120.1 | 206.0 |
| EAM264 | CAGAACTTAGCCACTGTGAA | mmu-miR-27b | +++ | 20 | 59.8 | 190.9 | 36.1 | 144.2 | 26.2 | 237.1 | 38.3 | 246.7 | 58.3 | 472.7 | 96.6 |

| Oligo ID | Oligo sequence | Small RNA (Rfam 3.0) | A B C | Oligo length | Tm (NN) | E12.5 | E12.5 SEM | E17.5 | E17.5 SEM | P4 | P4 SEM | P18 | P18 SEM | Adult | Adult SEM |
|---|---|---|---|---|---|---|---|---|---|---|---|---|---|---|---|
| EAM265 | AACCGATTTCAGATGGTGCTAG | mmu-miR-29a | - - - | 22 | 67.9 | 151.0 | 29.1 | 287.7 | 40.1 | 554.9 | 66.4 | 2,232.4 | 213.9 | 3,477.8 | 188.2 |
| EAM266 | AACACTGATTTCAAATGGTGCTA | mmu-miR-29b | - - - | 23 | 66.2 | 103.7 | 18.3 | 95.4 | 11.4 | 333.1 | 70.3 | 3,050.7 | 267.3 | 4,065.9 | 504.7 |
| EAM267 | AACACTGATTTCAAATGGTGCTA | mmu-miR-29b | - - - | 23 | 66.2 | 72.6 | 14.9 | 98.1 | 15.0 | 385.3 | 71.5 | 2,762.9 | 345.3 | 3,533.7 | 372.0 |
| EAM268 | AACCGATTTCAGATGGTGCTAG | mmu-miR-29a | +++ | 22 | 67.9 | 88.4 | 15.9 | 129.6 | 13.2 | 318.4 | 62.8 | 1,923.0 | 222.4 | 2,658.1 | 385.3 |
| EAM269 | GCTGCAAACATCCGACTGAAAG | mmu-miR-30a | - - - | 22 | 71.4 | 223.0 | 43.0 | 242.0 | 37.9 | 214.0 | 25.5 | 303.8 | 56.5 | 146.7 | 23.5 |
| EAM270 | GCTGAGTGTAGGATGTTTACA | mmu-miR-30b | +++ | 21 | 59.2 | 889.3 | 112.0 | 877.1 | 122.9 | 626.9 | 67.2 | 840.1 | 108.9 | 781.5 | 156.8 |
| EAM271 | GCTGAGAGTGTAGGATGTTTACA | mmu-miR-30c | +++ | 23 | 63.3 | 899.5 | 177.8 | 1,225.9 | 201.3 | 988.4 | 125.5 | 887.5 | 103.1 | 881.8 | 134.2 |
| EAM272 | CTTCCAGTCGGGATGTTTACA | mmu-miR-30d | +++ | 22 | 70.6 | 1,704.5 | 259.1 | 1,140.1 | 144.7 | 959.6 | 171.7 | 1,062.6 | 150.7 | 1,274.8 | 174.9 |
| EAM273 | CAATGCAACTACAATGCAC | mmu-miR-33 | +++ | 19 | 58.7 | 1,055.8 | 126.7 | 2,245.2 | 338.3 | 2,627.0 | 96.2 | 1,951.9 | 255.9 | 518.7 | 51.9 |
| EAM274 | CAATGCACAGCAATGCAC | miR-33b* | + - - | 19 | 65.0 | 59.6 | 9.7 | 125.4 | 22.9 | 193.2 | 27.2 | 61.7 | 9.7 | 58.9 | 8.2 |
| EAM275 | ACAACCAGCTAAGACACTGCCA | mmu-miR-34a | +++ | 22 | 69.0 | 319.3 | 40.8 | 289.8 | 45.6 | 320.7 | 24.2 | 258.5 | 46.1 | 404.1 | 82.3 |
| EAM276 | TCATACAGCTAGATAACCAAAGA | mmu-miR-9 | +++ | 23 | 61.4 | 6,168.0 | 683.6 | 4,628.0 | 272.5 | 3,281.3 | 413.8 | 2,797.7 | 447.1 | 2,336.5 | 462.2 |
| EAM277 | GCAAAAATGCTAGTGCCAAA | mmu-miR-96 | +++ | 22 | 70.0 | 12.1 | 2.9 | 10.3 | 2.5 | 14.0 | 2.8 | 23.1 | 6.0 | 10.0 | 10.0 |
| EAM278 | AACAATACAACTTACTACCTCA | mmu-miR-98 | +++ | 22 | 55.9 | 318.4 | 30.7 | 514.7 | 90.4 | 653.3 | 103.1 | 526.8 | 74.3 | 410.8 | 71.0 |
| EAM279 | TAACCGATTTCAAATGGTGCTA | mmu-miR-29c | +++ | 22 | 67.2 | 131.8 | 30.4 | 198.4 | 41.0 | 504.3 | 49.7 | 2,582.6 | 317.8 | 3,964.0 | 178.6 |
| EAM280 | GCTGCAAACATCCGACTGAAAG | mmu-miR-30a | +++ | 22 | 71.4 | 262.3 | 52.0 | 209.7 | 30.8 | 188.2 | 37.9 | 391.7 | 65.2 | 139.1 | 26.6 |
| EAM281 | ATCCAGTCAGTTCCTGATGCAGTA | mmu-miR-217 | + - - | 24 | 70.3 | 14.7 | 3.1 | 8.1 | 1.3 | 18.1 | 2.8 | 7.7 | 1.3 | 0.8 | 0.2 |
| EAM282 | GAACAGGTAGTCTAAACACTGGG | mmu-miR-199b | +++ | 23 | 64.5 | 193.5 | 47.1 | 87.9 | 18.1 | 62.8 | 9.2 | 30.9 | 6.0 | 3.7 | 0.9 |
| EAM283 | AGGCAAAGGATGACAAAGGGAA | mmu-miR-211 | +++ | 22 | 72.5 | 138.4 | 29.7 | 325.1 | 61.1 | 466.0 | 60.7 | 303.6 | 57.7 | 192.8 | 33.8 |
| EAM284 | AGAAAACATGCTCCAGGTGA | smallRNA-1 | - - - | 20 | 64.2 | 910.9 | 229.1 | 793.5 | 160.3 | 905.0 | 269.5 | 476.7 | 75.5 | 40.9 | 6.8 |
| EAM285 | ACTGGAGACACGTGCACTGAGA | miR-139# | + - - | 23 | 68.8 | 68.4 | 13.5 | 56.3 | 10.9 | 54.3 | 7.9 | 374.6 | 91.2 | 376.3 | 46.2 |
| EAM286 | TTAAATTAACCGGCGAATTCGC | smallRNA-7 | + - - | 22 | 69.4 | 4.5 | 1.2 | 3.0 | 0.5 | 3.5 | 0.7 | 1.3 | 0.2 | 2.4 | 0.5 |
| EAM287 | AAGACGGTGCTTACCTGTTCC | smallRNA-8 | + - - | 21 | 67.6 | 13.5 | 2.8 | 9.7 | 1.5 | 22.4 | 2.9 | 8.8 | 1.1 | 6.4 | 1.0 |
| EAM288 | ACACAAATTCGGTTCTACAGGG | mmu-miR-10b | +++ | 22 | 67.7 | 9.5 | 1.4 | 184.8 | 31.5 | 106.7 | 17.1 | 48.6 | 6.5 | 6.3 | 0.9 |
| EAM289 | AACAAGCCCAGACCGCAAAAG | mmu-miR-129 | +++ | 22 | 74.6 | 18.5 | 3.5 | 23.7 | 2.3 | 70.5 | 15.8 | 73.6 | 13.4 | 95.8 | 15.7 |

-continued

| Oligo ID | Oligo sequence | Small RNA (Rfam 3.0) | A B C | Oligo length | Tm (NN) | E12.5 | E12.5 SEM | E17.5 | E17.5 SEM | P4 | P4 SEM | P18 | P18 SEM | Adult | Adult SEM |
|---|---|---|---|---|---|---|---|---|---|---|---|---|---|---|---|
| EAM290 | ACCCTTATCAGTTCTCCGTCCA | mmu-miR-184 | +++ | 22 | 69.4 | 2.7 | 0.5 | 1.6 | 0.1 | 1.9 | 0.6 | 3.0 | 0.9 | 2.7 | 0.8 |
| EAM291 | GAACTGCCTTTCTCTCCA | mmu-miR-185 | +++ | 18 | 58.6 | 664.4 | 130.9 | 493.0 | 111.3 | 428.3 | 67.3 | 963.1 | 123.9 | 447.2 | 69.7 |
| EAM292 | AAGCCCAAAAGGAGAATTCTTTG | mmu-miR-186 | +++ | 23 | 70.5 | 178.6 | 35.5 | 101.7 | 16.5 | 102.6 | 11.6 | 101.3 | 14.7 | 59.9 | 12.0 |
| EAM293 | ACCCTCCACCATGCAAGGATG | mmu-miR-188 | +++ | 22 | 76.7 | 26.5 | 3.9 | 35.6 | 7.7 | 94.3 | 25.3 | 21.4 | 5.0 | 8.5 | 1.4 |
| EAM294 | ACTGATGTCAGCTCAGTAGGCAC | mmu-miR-189 | +++ | 23 | 67.7 | 12.0 | 2.2 | 9.8 | 1.8 | 20.2 | 5.1 | 20.1 | 3.5 | 14.5 | 3.4 |
| EAM295 | ACCTAATATATCAAACATATCA | mmu-miR-190 | +++ | 22 | 53.7 | 41.5 | 9.1 | 37.6 | 6.0 | 63.7 | 13.5 | 41.3 | 5.4 | 39.7 | 7.1 |
| EAM296 | AGTGTGCTTTTGGGATTCCGTTG | mmu-miR-191 | +++ | 22 | 74.5 | 2,769.9 | 200.2 | 2,792.5 | 302.4 | 2,650.5 | 114.3 | 2,470.8 | 297.4 | 2,153.6 | 184.4 |
| EAM297 | CTGGGACTTGTGTAGGCCAGTT | mmu-miR-193 | +++ | 21 | 67.6 | 397.2 | 54.3 | 562.8 | 49.3 | 388.2 | 44.6 | 512.0 | 64.7 | 294.4 | 32.9 |
| EAM298 | TCCACATGGAGTTGCTGTTACA | mmu-miR-194 | +++ | 22 | 67.9 | 16.4 | 4.6 | 20.2 | 4.4 | 15.4 | 2.6 | 28.1 | 6.2 | 11.2 | 3.4 |
| EAM299 | GCCAATATTTCTGTGCTGCTA | mmu-miR-195 | +++ | 21 | 65.2 | 768.1 | 124.8 | 820.3 | 125.9 | 479.0 | 48.8 | 472.3 | 75.1 | 534.4 | 73.2 |
| EAM300 | GCTGGGTGGAGAAGGTGGTGAA | hsa-miR-197 | +-- | 22 | 74.9 | 3.2 | 0.5 | 2.1 | 0.3 | 1.0 | 0.2 | 1.2 | 0.2 | 1.8 | 0.3 |
| EAM301 | CCTATCTCCCCTCTGGACC | hsa-miR-198 | ++- | 19 | 64.5 | 0.8 | 0.3 | 0.2 | 0.1 | 3.0 | 0.9 | 0.3 | 0.1 | 1.1 | 0.2 |
| EAM302 | AACAGGTAGTCTGAACACTGGG | mmu-miR-199a | --- | 22 | 65.0 | 228.3 | 35.3 | 111.4 | 15.8 | 62.9 | 10.0 | 23.0 | 4.7 | 12.1 | 2.3 |
| EAM303 | AACCAATGTGCAGACTACTGTA | mmu-miR-199a* | +++ | 22 | 61.7 | 203.0 | 29.9 | 111.5 | 12.4 | 76.3 | 12.2 | 19.6 | 2.1 | 11.0 | 1.5 |
| EAM304 | CATCGTTACCAGACAGTGTTA | mmu-miR-200a | +++ | 21 | 59.9 | 19.0 | 7.0 | 60.4 | 11.4 | 295.4 | 39.7 | 515.8 | 83.6 | 242.9 | 66.7 |
| EAM305 | GTCATCATTACCAGGCAGTATTA | mmu-miR-200b | +++ | 23 | 63.5 | 19.2 | 4.0 | 14.8 | 1.7 | 97.3 | 20.5 | 110.9 | 22.8 | 87.8 | 13.7 |
| EAM306 | AGAACAATGCCTTACTGAGTA | mmu-miR-201 | +++ | 21 | 58.6 | 0.1 | 0.2 | 0.5 | 0.4 | 0.0 | 0.1 | -0.2 | 0.2 | -0.3 | 0.2 |
| EAM307 | TCTTCCCATGCGCTATACCTCT | mmu-miR-202 | +++ | 22 | 69.9 | 0.2 | 0.1 | 0.3 | 0.1 | 0.2 | 0.1 | 0.4 | 0.1 | 0.2 | 0.0 |
| EAM308 | CCCACACACTTCCTTACATTCCA | mmu-miR-206 | +++ | 22 | 66.6 | 59.4 | 15.1 | 118.9 | 27.5 | 300.4 | 48.1 | 672.6 | 118.0 | 310.3 | 40.3 |
| EAM309 | GAGGGAGGAGAGCCAGGAGAAGC | mmu-miR-207 | +++ | 23 | 76.0 | 3.4 | 1.0 | 1.2 | 0.3 | 0.9 | 0.2 | 0.7 | 0.1 | 1.6 | 0.3 |
| EAM310 | ACAAGCTTTTTGCTCGTCTTAT | mmu-miR-208 | +++ | 22 | 65.3 | -0.1 | 0.2 | 1.3 | 0.5 | 1.0 | 0.5 | 0.7 | 0.2 | 0.4 | 0.2 |

TABLE 3

| Oligo ID | Oligo sequence | SEQ ID NO: |
|---|---|---|
| EAM101 | TCCATCATCAAAACAAATGGAGT | 5 |
| EAM102 | TCCATCATGAAAAGAAATGGAGT | 6 |
| EAM103 | TGGCATTCACCGCGTGCCTTA | 7 |
| EAM104 | TGGCATTCAGCGGGTGCCTTA | 8 |
| EAM105 | TCACAAGTTAGGGTCTCAGGGA | 9 |
| EAM106 | TCACAAGTAAGGGTGTCAGGGA | 10 |
| EAM107 | TGTTCCTGCTGAACTGAGCCA | 11 |
| EAM108 | TGTTCCTGGTGAAGTGAGCCA | 12 |
| EAM109 | AACAACAAAATCACTAGTCTTCCA | 13 |
| EAM110 | AACAACAAAATGAGTAGTCTTCCA | 14 |
| EAM1100 | GCATGCATGCATGCATGCATG | 15 |
| EAM1101 | GTGGTAGCGCAGTGCGTAGAA | 16 |
| EAM1102 | GGTGATGCCCTGAATGTTGTC | 17 |
| EAM1103 | TGTCATGGATGACCTTGGCCA | 18 |
| EAM1104 | CTTTTGACATTGAAGGGAGCT | 19 |
| EAM111 | TAACTGTACAAACTACTACCTCA | 20 |
| EAM112 | TAACTGTAGAAAGTACTACCTCA | 21 |
| EAM113 | ACAGGTTAAAGGGTCTCAGGGA | 22 |
| EAM114 | ACAGGTAAAAGGGTGTCAGGGA | 23 |
| EAM115 | CGCCAATATTTACGTGCTGCTA | 24 |
| EAM116 | CGCCAAATATTAAGGTGCTGCTA | 25 |
| EAM117 | TAACCGATTTCAAATGGTGCTA | 26 |
| EAM118 | TAACCGATTTGAAAAGGTGCTA | 27 |
| EAM119 | AACACTGATTTCAAATGGTGCTA | 28 |
| EAM120 | AACACTGATTTGAAAAGGTGCTA | 29 |
| EAM121 | CACAAGATCGGATCTACGGGT | 30 |
| EAM122 | CACAAGATGGGATGTACGGGT | 31 |
| EAM123 | AACTATGCAACCTACTACCTCT | 32 |
| EAM124 | AACTATGCAACGTAGTACCTCT | 33 |
| EAM125 | CGGCCTGATTCACAACACCAGCT | 34 |
| EAM126 | CGGCCTGATTGAGAACACCAGCT | 35 |
| EAM127 | TCATAGCCCTGTACAATGCTGCT | 36 |
| EAM128 | TCATAGCCCTGAAGAATGCTGCT | 37 |
| EAM129 | AGGCATTCACCGCGTGCCTTAT | 38 |
| EAM130 | AGGCATTCAGCGGGTGCCTTAT | 39 |
| EAM131 | ACAGGCCGGGACAAGTGCAATAT | 40 |
| EAM132 | ACAGGCCGGGAGAAGAGCAATAT | 41 |
| EAM133 | ACACCAATGCCCTAGGGGATGCG | 42 |
| EAM134 | ACACCAATGCCGTAGGGGATGCG | 43 |
| EAM135 | CAACAAACATTTAATGAGGCC | 44 |
| EAM136 | CAACAAAGATTAAATGAGGCC | 45 |
| EAM137 | CCGACCATGGCTGTAGACTGTTA | 46 |
| EAM138 | CCGACCATGGGTGAAGACTGTTA | 47 |
| EAM139 | TAACCCATGGAATTCAGTTCTCA | 48 |
| EAM140 | TAACCCATGGAAATGAGTTCTCA | 49 |
| EAM141 | TAACTATACAATCTACTACCTCA | 50 |
| EAM142 | TAACTATACAATGTAGTACCTCA | 51 |
| EAM143 | TAACCATACAACCTATTACCTCA | 52 |
| EAM144 | TAACCATAGAACGTATTACCTCA | 53 |
| EAM145 | AACCATACAACCTACTACCTCA | 54 |
| EAM146 | AACCATACAAGCTAGTACCTCA | 55 |
| EAM147 | AACCACACAACCTACTACCTCA | 56 |
| EAM148 | AACCACACAAGCTAGTACCTCA | 57 |
| EAM149II | GCATTCACCCGCGTGCCTTA | 58 |
| EAM150II | TCATACAGCTAGATAACCAAAGA | 59 |
| EAM151 | ACAAGATCGGATCTACGG | 60 |
| EAM152 | ACTTTCGGTTATCTAGCTTTAT | 61 |
| EAM153 | AACTATACAACCTACTACCTCA | 62 |
| EAM154 | AAAGAGACCGGTTCACTGTGA | 63 |
| EAM155 | TCCATCATCAAAACAAATGGAGT | 64 |
| EAM156 | ACTCACCGAGAGAGCGTTGAATGTT | 65 |
| EAM157 | TGGTGTCAGAAGTGGGATAC | 66 |
| EAM158 | TACAGCTAAATAACCAAAGA | 67 |
| EAM159 | ATGCCCTTTTAACATTGCACTG | 68 |
| EAM160 | AACCTATCCTGAATTACTTGAA | 69 |
| EAM161 | CTCAATAGACTGTGAGCTCCTT | 70 |
| EAM162 | ATCAAGGTCCGCTGTGAACACG | 71 |
| EAM163 | TCCATAAAGTAGGAAACACTACA | 72 |
| EAM164 | GAGTGCTTGCTAGGTGCCAAG | 73 |
| EAM165 | GGGAGTGAAGACACGGAGCCAGA | 74 |
| EAM166 | GCCTATCCTGGATTACTTGAA | 75 |
| EAM167 | GTTGTGGTCACTTACAATT | 76 |
| EAM168 | CTATACAACCTCCTACCTCA | 77 |
| EAM169 | AACAGCACAAACTACTACCTCA | 78 |
| EAM170 | TGGCATTCACCGCCGTGCCTTA | 79 |
| EAM171 | CTACGCGTATTCTTAAGCAATAA | 80 |
| EAM172 | CTCGTACTGAGCAGGATTA | 81 |
| EAM173 | GTCTCGAAAAGGTAGCGTTC | 82 |
| EAM174 | AGAAAACATGCTCCAGGTGA | 83 |
| EAM175 | TCGCCCTCTCAACCCAGCTTTT | 84 |
| EAM176 | TACAGTACTGTGATAGCTGAA | 85 |
| EAM177 | TTCAGCTATCACAGTACTGTA | 86 |
| EAM178 | TGCCAATATTTCTGTGCTGCTA | 87 |
| EAM179 | ACTATGCAACCTACTACCTCT | 88 |
| EAM180 | AACTATAGAATCTACTACCTCA | 89 |
| EAM181 | AACTATACAATCTACTACCTCA | 90 |
| EAM182 | AACTGTACACTACTACCTCA | 91 |
| EAM183 | AGCACAAACTACTACCTCA | 92 |
| EAM184 | CACAAGTTCGGATCTACGGGTT | 93 |
| EAM185 | TCATAGCCCTGTACAATGCTGCT | 94 |
| EAM186 | GCTACCTGCACTGTAAGCACTTTT | 95 |
| EAM187 | TGATAGCCCTGTACAATGCTGCT | 96 |
| EAM188 | AATGCCCTAAAAAATCCTTAT | 97 |
| EAM189 | CACAAATTCGGATCTACAGGGTA | 98 |
| EAM190 | ACAAATTCGGTTCTACAGGGTA | 99 |
| EAM191 | ACAAACACCATTGTCACACTCCA | 100 |
| EAM192 | CGCGTACCAAAAGTAATAATG | 101 |
| EAM193 | CACAGGTTAAAGGGTCTCAGGGA | 102 |
| EAM194 | AAAAGAGACCGGTTCACTGTGA | 103 |
| EAM195 | GAAAGAGACCGGTTCACTGTGA | 104 |
| EAM196 | GCAAGCCCAGACCGAAAAAAG | 105 |
| EAM197 | GCAAGCCCAGACCGCAAAAAG | 106 |
| EAM198 | GCCCTTTCATCATTGCACTG | 107 |
| EAM199 | ACGACCATGGCTGTAGACTGTTA | 108 |
| EAM200 | ACAGCTGGTTGAAGGGGACCAA | 109 |
| EAM201 | TAGGTGGTTGAAGGGGACCAA | 110 |
| EAM202 | TCCCTCTGGTCAACCAGTCACA | 111 |
| EAM203 | TTCACATAGGAATAAAAAGCCATA | 112 |
| EAM204 | ATCACATAGGAATAAAAAGCCATA | 113 |
| EAM205 | GATTCACAACACCAGCT | 114 |
| EAM206 | AGACACGTGCACTGTAGA | 115 |
| EAM207 | CTACCATAGGGTAAAACCACT | 116 |
| EAM208 | CCATCTTTACCAGACAGTGTT | 117 |
| EAM209 | GTAGTGCTTTCTACTTTATG | 118 |
| EAM210 | tgAGCTACAGTGCTTCATCTCA | 119 |
| EAM211 | CTAGTACATCATCTATACTGTA | 120 |
| EAM212 | AAGGGATTCCTGGGAAAACTGGAC | 121 |
| EAM213 | AAACCCATGGAATTCAGTTCTCA | 122 |
| EAM214 | ACAAAGTTCTGTAGTGCACTGA | 123 |
| EAM215 | ACAAAGTTCTGTGATGCACTGA | 124 |
| EAM216 | GGAGTGAAGACACGGAGCCAGA | 125 |
| EAM217 | ACACTGGTACAAGGGTTGGGAGA | 126 |
| EAM218 | CCAAGTTCTGTCATGCACTGA | 127 |
| EAM219 | TCACTTTTGTGACTATGCAA | 128 |
| EAM220 | CGAAGGCAACACGGATAACCTA | 129 |
| EAM221 | CCCCTATCACAATTAGCATTAA | 130 |
| EAM222 | CACAAACCATTATGTGCTGCTA | 131 |
| EAM223 | TGTAAACCATGATGTGCTGCTA | 132 |
| EAM224 | ACTACCTGCACTGTAAGCACTTTG | 133 |
| EAM225 | TATCTGCACTAGATGCACCTTA | 134 |
| EAM226 | ACTCACCGACAGCGTTGAATGTT | 135 |
| EAM227 | AACCCACCGACAGCAATGAATGTT | 136 |
| EAM228 | ACTCACCGACAGGTTGAATGTT | 137 |
| EAM229 | TGTGAGTTCTACCATTGCCAAA | 138 |
| EAM230 | CAGTGAATTCTACCAGTGCCATA | 139 |
| EAM231 | CGGCTGCAACACAAGACACGA | 140 |
| EAM232 | GGCTGTCAATTCATAGGTCAG | 141 |
| EAM233 | CCCAACAACATGAAACTACCTA | 142 |
| EAM234 | GAACAGGTAGTCTGAACACTGGG | 143 |
| EAM235 | GAACAGATAGTCTAAACACTGGG | 144 |
| EAM236 | TCAGTTTTGCATAGATTTGCACA | 145 |
| EAM237 | TCAGTTTTGCATGCATTTGCACA | 146 |
| EAM238 | ATACATACTTCTTTACATTCCA | 147 |
| EAM239 | ATACATACTTCTTTACATTCCA | 148 |
| EAM240 | CTACCTGCACTATAAGCACTTTA | 149 |
| EAM241 | CTAGTGGTCCTAAACATTTCAC | 150 |
| EAM242 | AGGCATAGGATGACAAAGGGAA | 151 |
| EAM243 | CAGACTCCGGTGGAATGAAGGA | 152 |
| EAM244 | TCAACATCAGTCTGATAAGCTA | 153 |
| EAM245 | CAGCCGCTGTCACACGCACAG | 154 |
| EAM246 | AGGCGAAGGATGACAAAGGGAA | 155 |
| EAM247 | GGCCGTGACTGGAGACTGTTA | 156 |

TABLE 3-continued

| Oligo ID | Oligo sequence | SEQ ID NO: |
|---|---|---|
| EAM248 | GGTACAATCAACGGTCGATGGT | 157 |
| EAM249 | CTGCCTGTCTGTGCCTGCTGT | 158 |
| EAM250 | GTCTGTCAATTCATAGGTCAT | 159 |
| EAM251 | CACAGTTGCCAGCTGAGATTA | 160 |
| EAM252 | ATCCAATCAGTTCCTGATGCAGTA | 161 |
| EAM253 | ACATGGTTAGATCAAGCACAA | 162 |
| EAM254 | AGAATTGCGTTTGGACAATCA | 163 |
| EAM255 | ACAGTTCTTCAACTGGCAGCTT | 164 |
| EAM256 | AAAGTGTCAGATACGGTGTGG | 165 |
| EAM257 | GAAACCCAGCAGACAATGTAGCT | 166 |
| EAM258 | GAGACCCAGTAGCCAGATGTAGCT | 167 |
| EAM259 | GGGGTATTTGACAAACTGACA | 168 |
| EAM260 | GGAAATCCCTGGCAATGTGAT | 169 |
| EAM261 | GTGGTAATCCCTGGCAATGTGAT | 170 |
| EAM262 | CTGTTCCTGCTGAACTGAGCCA | 171 |
| EAM263 | AGCCTATCCTGGATTACTTGAA | 172 |
| EAM264 | CAGAACTTAGCCACTGTGAA | 173 |
| EAM265 | AACCGATTTCAGATGGTGCTAG | 174 |
| EAM266 | AACACTGATTTCAAATGGTGCTA | 175 |
| EAM267 | AACACTGATTTCAAATGGTGCTA | 176 |
| EAM268 | AACCGATTTCAGATGGTGCTAG | 177 |
| EAM269 | GCTGCAAACATCCGACTGAAAG | 178 |
| EAM270 | GCTGAGTGTAGGATGTTTACA | 179 |
| EAM271 | GCTGAGAGTGTAGGATGTTTACA | 180 |
| EAM272 | CTTCCAGTCGGGGATGTTTACA | 181 |
| EAM273 | CAATGCAACTACAATGCAC | 182 |
| EAM274 | CAATGCAACAGCAATGCAC | 183 |
| EAM275 | ACAACCAGCTAAGACACTGCCA | 184 |
| EAM276 | TCATACAGCTAGATAACCAAAGA | 185 |
| EAM277 | GCAAAAATGTGCTAGTGCCAAA | 186 |
| EAM278 | AACAATACAACTTACTACCTCA | 187 |
| EAM279 | TAACCGATTTCAAATGGTGCTA | 188 |
| EAM280 | GCTGCAAACATCCGACTGAAAG | 189 |
| EAM281 | ATCCAGTCAGTTCCTGATGCAGTA | 190 |
| EAM282 | GAACAGGTAGTCTAAACACTGGG | 191 |
| EAM283 | AGGCAAAGGATGACAAAGGGAA | 192 |
| EAM284 | AGAAAACATGCTCCAGGTGA | 193 |
| EAM285 | ACTGGAGCACGTGCACTGTAGA | 194 |
| EAM286 | TTAAATTAACCGCGAATTCGC | 195 |
| EAM287 | AAGACGGTGCTTACCTGTTCC | 196 |
| EAM288 | ACACAAATTCGGTTCTACAGGG | 197 |
| EAM289 | AACAAGCCCAGACCGCAAAAAG | 198 |
| EAM290 | ACCCTTATCAGTTCTCCGTCCA | 199 |
| EAM291 | GAACTGCCTTTCTCTCCA | 200 |
| EAM292 | AAGCCCAAAAGGAGAATTCTTTG | 201 |
| EAM293 | ACCCTCCACCATGCAAGGGATG | 202 |
| EAM294 | ACTGATGTCAGCTCAGTAGGCAC | 203 |
| EAM295 | ACCTAATATATCAAACATATCA | 204 |
| EAM296 | AGCTGCTTTTGGGATTCCGTTG | 205 |
| EAM297 | CTGGGACTTTGTAGGCCAGTT | 206 |
| EAM298 | TCCACATGGAGTTGCTGTTACA | 207 |
| EAM299 | GCCAATATTTCTGTGCTGCTA | 208 |
| EAM300 | GCTGGGTGGAGAAGGTGGTGAA | 209 |
| EAM301 | CCTATCTCCCCTCTGGACC | 210 |
| EAM302 | AACAGGTAGTCTGAACACTGGG | 211 |
| EAM303 | AACCAATGTGCAGACTACTGTA | 212 |
| EAM304 | CATCGTTACCAGACAGTGTTA | 213 |
| EAM305 | GTCATCATTACCAGGCAGTATTA | 214 |
| EAM306 | AGAACAATGCCTTACTGAGTA | 215 |
| EAM307 | TCTTCCCATGCGCTATACCTCT | 216 |
| EAM308 | CCACACACTTCCTTACATTCCA | 217 |
| EAM309 | GAGGGAGGAGAGCCAGGAGAAGC | 218 |
| EAM310 | ACAAGCTTTTGCTCGTCTTAT | 219 |

A summary of the microarray data is presented in Table 2. Oligonucleotide sequences correspond to probes on the array. MicroRNA names were obtained from the January 2004 release of the Rfam database or if these were not available, then microarray names were obtained from NCBI. Probes named smallRNA-1 through -13 correspond to unique small RNAs that we cloned. The small RNAs did not correspond to known microRNAs and did not have perfect matches in the current release of the rat genome sequence. Column A indicates whether the probe is complementary to a microRNA or to one of the small RNAs we cloned ("−"=no, "+"=yes). Column B indicates whether the probe is complementary to a mouse microRNA. Oligonucleotides with a "−" in column A were either controls or were sequences that while submitted to public databases as microRNAs were later found not to encode microRNAs. In a few cases we printed probes that represented the same microRNA twice, but we analyzed the data from only one of these probes. The probes we did not analyze have no labels in columns A, B, and C. Melting temperatures were calculated using the nearest neighbors method (Breslauer et al., *Proc Natl Acad Sci USA* 1986, 83:3746-3750). Data for the five time points of mouse brain development (E12.5, E17.5, P4, P18 and adult) are shown. Microarray data was derived as described in more detail below. Briefly, data corresponding to mean spot intensities were averaged over quadruplicates (on each array) and four independent hybridizations. SEM refers to the standard error of the mean. microRNAs labeled with % are not in the current release of Rfam, but are deposited in NCBI and are described elsewhere (Lim et al., *Science* 299:1540, 2003; Lagos-Quintana et al., *Curr Biol* 12:735-739, 2002; Dostie *RNA* 9:180-186, 2003).

Printing and hybridization were done using the protocols from the slides manufacturer with the following modifications: the oligonucleotide concentration for printing was 20 μM in 150 mM sodium phosphate, pH 8.5, and hybridization was at 50° C. for 6 hours. Printing was done using a Micro-Grid TAS II arrayer (BIOROBOTICS, Cambridge, UK) at 50% humidity.

Sample and Probe Preparation

Whole brains from three to eight C57BL/6 mice were pooled. Starting with 250 μg of total RNA for each timepoint, 18-26 nucleotide RNA was purified using denaturing polyacrylamide gel electrophoresis. The samples were divided, and the following cloning steps were done twice independently for each timepoint.

3' and 5' adaptor oligonucleotides were ligated to 18-26 nucleotide RNA followed by reverse transcription, essentially as described for microRNA cloning (Lagos-Quintana et al., *Curr Biol* 12:735-739, 2002). Briefly, an RNA-DNA hybrid 5'-pUUUaaccgcgaattccagt-idT-3' (SEQ ID NO:220) (DHARMACON, Lafayette, Colo.) (X=RNA, x=DNA, p=phosphate, idT=inverted [3'-3' bond] deoxythymidine) was ligated to the 3' end and 5'-acggaattcctcactAAA-3' (SEQ ID NO:221) (DHARMACON, Lafayette, Colo.) was ligated to the 5' end. The ligation products were divided into two aliquots, and the following steps were done twice independently for each time point. Ligation products were reverse transcribed and amplified by ten rounds of PCR (40 seconds at 94° C., 30 seconds at 50° C., 30 seconds at 72° C.). For PCR, the oligonucleotides used were: oligo1: 5'-Cy3-acggaat-tcctcactaaa-3' (SEQ ID NO:386) and oligo2: 5'-tactggaat-tcgcggttaa-3' (SEQ ID NO:387). The PCR product was precipitated, washed and resuspended in hybridization buffer (5×SSC, 0.1% SDS, 0.1 mg/ml sheared denatured salmon sperm DNA).

Data Acquisition and Analysis

Microarray slides were scanned using an arrayWoRx$^e$ biochip reader (APPLIED PRECISION, Issaquah, Wash.), and primary data were analyzed using the Digital Genome System suite (Molecularware, Cambridge, Mass.) and the Spotfire Decision Site (Spotfire, Somerville, Mass.). Cluster analysis was performed using the CLUSTER/TreeView software (Eisen et al., *Proc Natl Acad Sci USA* 95:14863-14868, 1998).

Samples/Hybridizations

Figure 10:
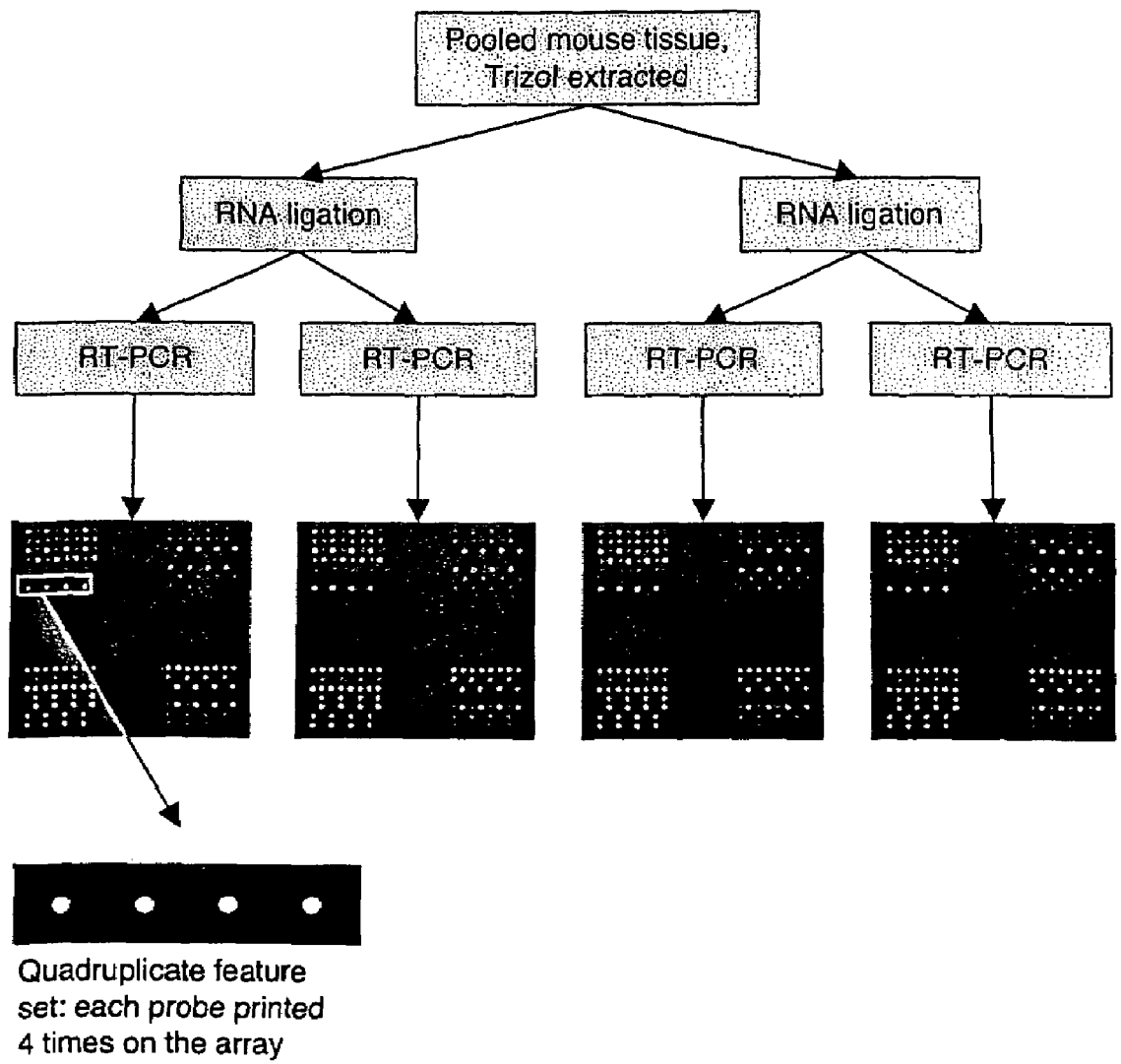
FIG. 10 is a schematic diagram illustrating the methods used for microarray design and data analysis.

Samples were processed as depicted in FIG. 10. For each sample, two independent ligations were performed. The products of the two ligations were split, and two independent reverse transcription/amplifications/hybridizations were performed. Thus, for each sample data were collected from four independent array hybridizations.

Arrays/Normalization

Figure 11:
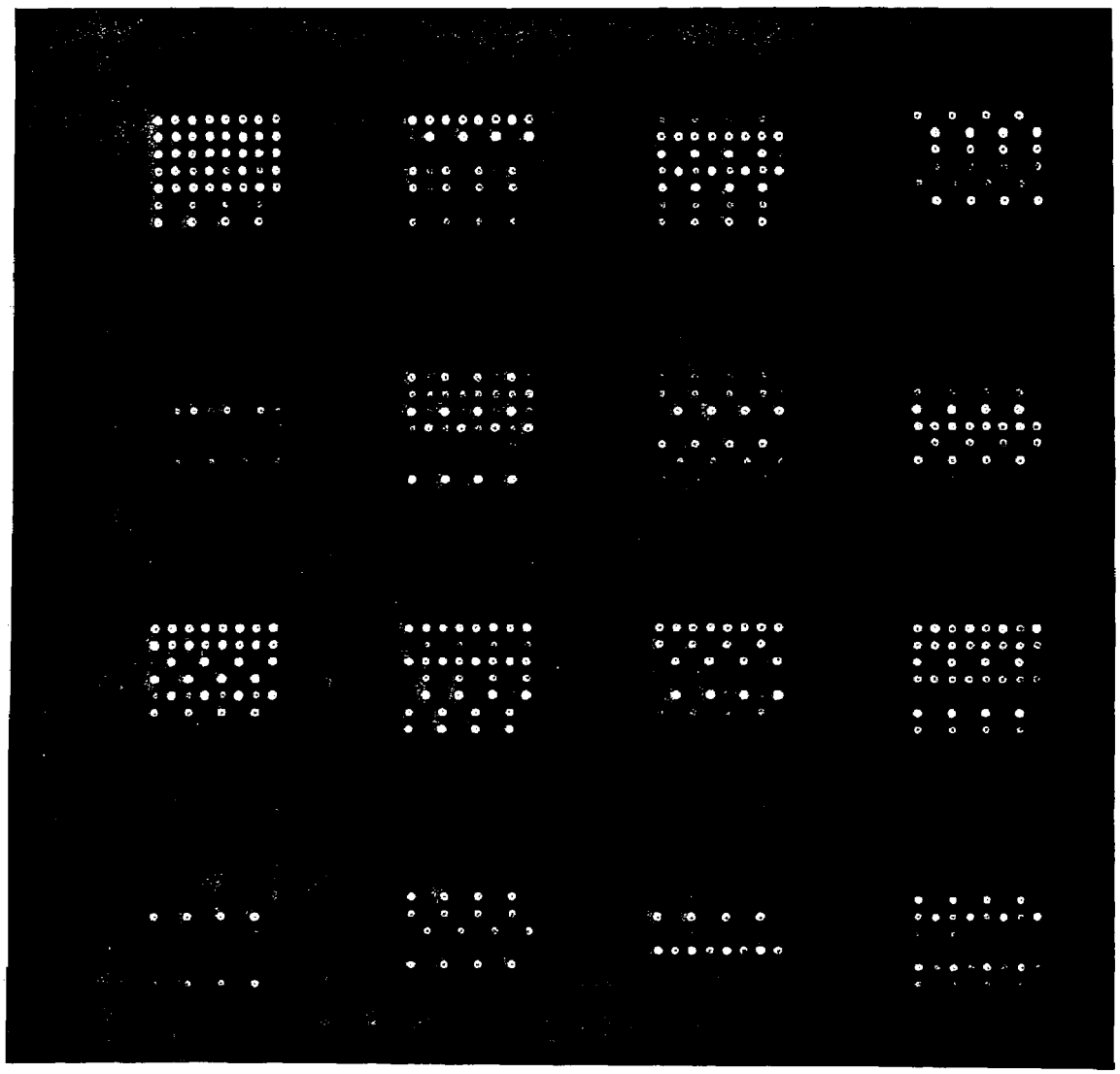
FIG. 11 shows an exemplary microarray scan.
Figure 12:
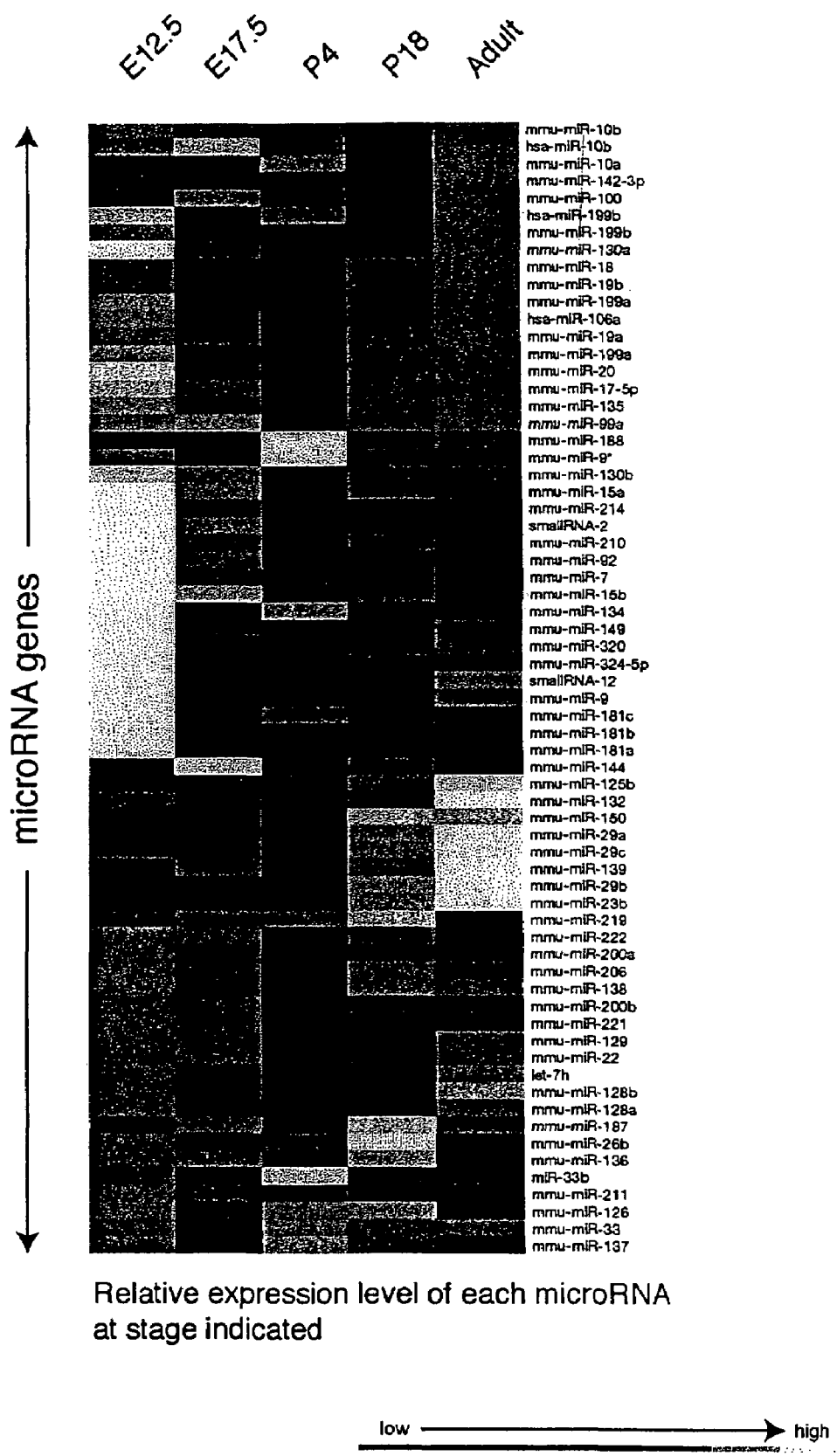
FIG. 12 shows the relative expression level of each of the indicated microRNAs at the indicated developmental stages.

Glass slides were arrayed using quadruplicate spots for each of the 138 microRNA probes, 19 small RNA probes, and control probes (FIG. 10 and Table 2). A sample microarray scan is shown in FIG. 11. The microarray consists of 16 squares of eight by seven spots each. Quadruplicates are identified as rows of four spots (every other spot) in the individual squares. A TIFF file of the scanned array is used for subsequent array analysis (DIGITAL GENOME SYSTEM SUITE, MOLECULARWARE, Cambridge, Mass.). Normalized spot intensities were used for all data analysis. For inter-array comparisons, all data were scaled based on total array intensities (scaling factors ranged from 0.4 to 2.6), and data for each sample and each gene were averaged and the standard error of the mean (SEM) was calculated. Total array intensity was calculated as the sum of the normalized spot intensity for all spots in the microarray. A variance analysis (ANOVA) was performed using Spotfire DecisionSite (Spotfire). Hierarchical clustering was performed using CLUSTER 3.0/TreeView software (Hoon et al., *Bioinformatics* 20: 1453-1454, 2004). For CLUSTER 3.0/TreeView output see FIG. 11, which shows a profile of microRNA expression in the developing mouse brain. The gray scale arrows indicate relative signal intensities. The microRNA expression profile was sorted using a hierarchical clustering method (see above). Only data from 66 probes that changed at least two-fold over the developmental time course (ANOVA, P<0.001) are shown. The data used for the analysis are present in Table 2.

Control Probes

Control probes were either negative controls or mismatch controls. The negative controls were either a synthetic $(GCAT)_n$ oligonucleotide (EAM100) or sequences derived from mouse mRNA sequences (EAM1101-1104).

| oligo ID | oligo sequence | mRNA |
|---|---|---|
| EAM1100 | GCATGCATGCATGCATGCATG | Synthetic (SEQ ID NO:222) |
| EAM1101 | GTGGTAGCGCAGTGCGTAGAA | beta-tubulin (SEQ ID NO:223) |
| EAM1102 | GGTGATGCCCTGAATGTTGTC | histone H4 (SEQ ID NO:224) |
| EAM1103 | TGTCATGGATGACCTTGGCCA | glyceraldehyde dehydrogenase (SEQ ID NO:225) |
| EAM1104 | CTTTTGACATTGAAGGGAGCT | laminin alpha 4 (SEQ ID NO:226) |

The mismatch controls were probes with two mismatches to a specific microRNA probe. For each mismatch control probe, two central Cs were replaced by two Gs; if this change was not possible, one C was replaced with a G and one T with an A. Averaged, normalized spot intensities for these negative controls ranged from −0.8 to 1.2, as compared with 90 to 14,250 for microRNA probes that were scored as signals. Negative values resulted from the subtraction of the local background signal surrounding each spot on the arrays.

Expression Levels and Microarray Correlations

Figure 13:
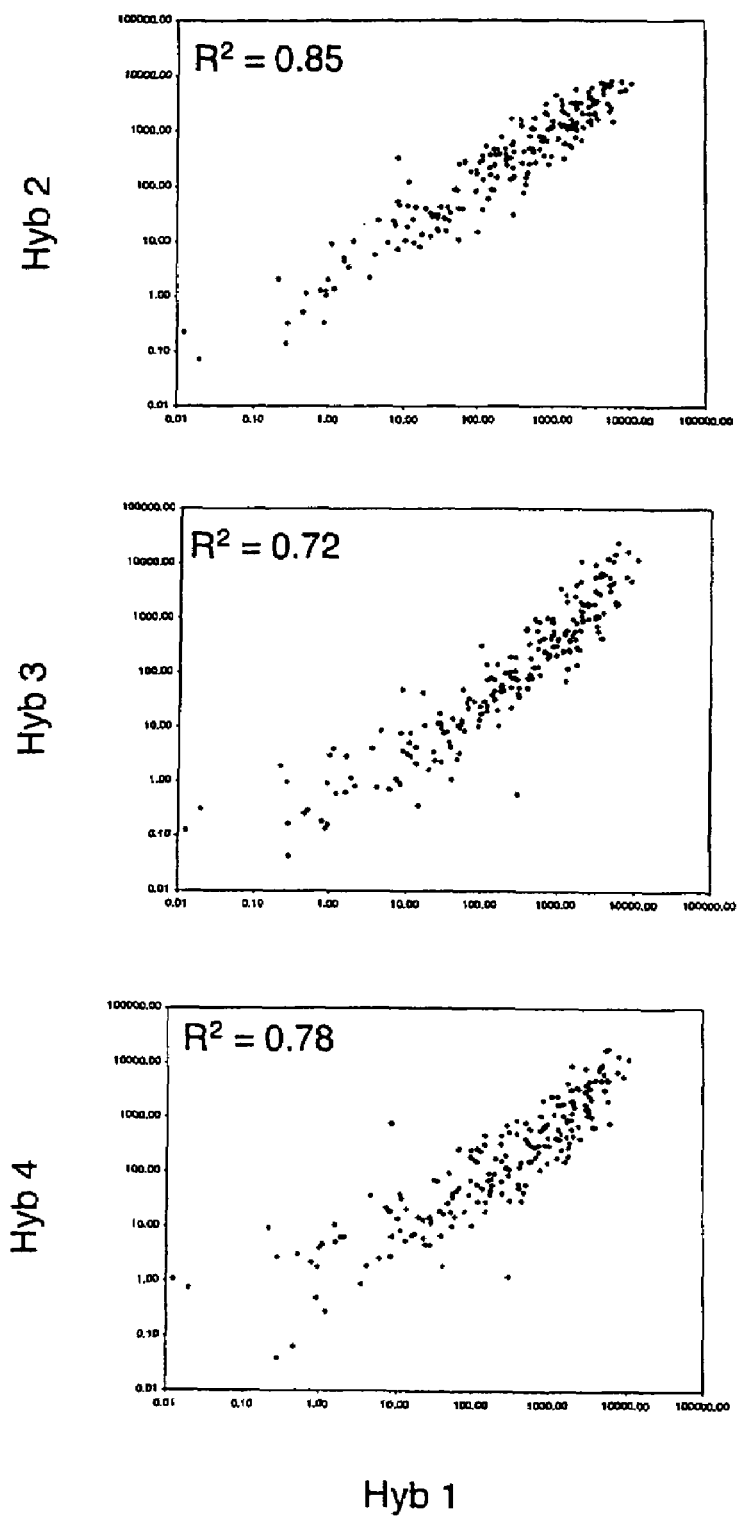
FIG. 13 shows three scatter plots depicting the correlations of four hybridizations at time point E12.5. For each graph, the axes show averaged mean spot intensities for all probes from a given data set, as indicated.
Figure 14:
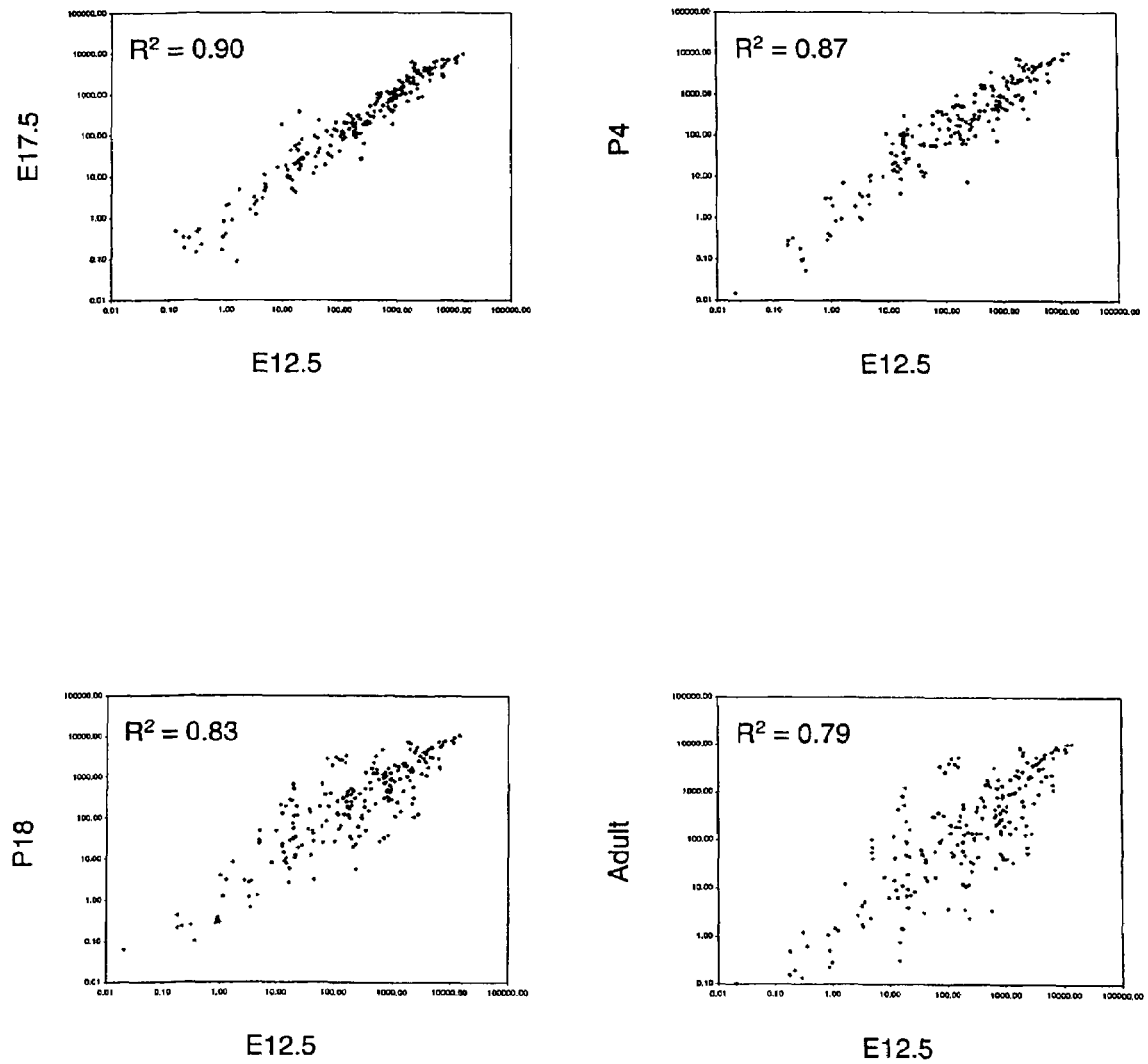
FIG. 14 shows four scatter plots that depict the correlations of the hybridization data obtained at E12.5 with the data from the other indicated timepoints (each set of data is averaged over four hybridizations).

Two methods were used to distinguish signal versus noise. First, we used correlation analysis among the four hybridizations for a given time point to assess reproducibility. Second, we used a set of negative control probes (see above) to measure noise. As an example, FIG. 13 shows the correlations (scatter plots) among the four hybridizations for time point E12.5. For each graph the axes show averaged mean spot intensities for all probes from a given data set, as indicated. Arbitrarily, we chose a cutoff of 90 for our analysis. Expressed relative to background values, a microRNA was identified as being present only if the signal was at least 75-fold over that of the negative controls for at least one timepoint. FIG. 14 shows the correlations (scatter plots) of the data for E12.5 with the data from each other timepoint (each averaged over four hybridizations). As expected, the correlation between E12.5 and E17.5 is highest, and the correlation decreases with samples from more distant developmental stages.

Specificity Index

To assess probe specificity, we compared the signal from oligonucleotides (probes) complementary to microRNAs (matched probe) and oligonucleotides with mismatches (mismatched probe, see above). Mismatched oligonucleotides were printed for the first 24 probes (EAM101, EAM103, . . . EAM147) and were named EAM102, EAM104, . . . EAM148. Mismatched oligonucleotides were spotted as nearest neighbors to microRNA oligonucleotides. To calculate the specificity index (FIG. 6A) we used datasets from two samples of each of the five time points from this study (5 time points×2 independent samples=10 hybridizations total). Calculations were based on cumulative signals from all experiments. EAM141, EAM143, EAM145 and EAM147 are let-7 family members and have very similar sequences. EAM117, EAM119 and EAM107 and EAM109 are also closely related. Therefore, there might be cross-reactivity within each of these groups. The matched/mismatched probe pair EAM135/ EAM136 was excluded from FIG. 6A as EAM136 did not give a signal above background at any of the five time points.

Summary of Features on the Microarray (Probe Set)

| | |
|---|---|
| Mouse microRNAs (Rfam 3.0) | 129 |
| Other mammalian microRNAs (Rfam 3.0, rat and human) | 9 |
| Other unique small RNAs | 18 |
| Total | 156 |

Of the 156 unique small RNA probes, we found that 116 (74%) showed robust signals for at least one of the five time points. Of these, 83 changed significantly (ANOVA, P<0.001) and 66 changed by more than two-fold.

The predicted stem-loop RNA structures were generated using the mfold (version 3.1) software (Zuker *Nucleic Acids Res*, 31:3406-3415, 2003).

Northern Blots

Northern blots were performed as described (Lau et al., *Science* 294:858-862, 2001). 25 µg of total RNA was loaded per lane. A probe for the mouse U6 snRNA (5'-tgtgctgc-cgaagcgagcac-3') was used as a loading control. The probe for each northern blots had the same sequences as the corresponding EAM# oligonucleotides printed on the microarray as shown in Table 2. Each blot was stripped by boiling for 5 minutes in distilled water and was reprobed up to four times. The probes used were as follows: EAM119 (miR-29b), EAM125 (miR-138), EAM224 (miR-17-5p), EAM234 (miR-199a), EAM131 (miR-92), EAM109 (miR-7), EAM150 (miR-9) and EAM103 (miR-124a).

Detectably Labeled microRNA

First, small RNAs (e.g., 18-26 nucleotides) are size-selected from total RNA, for example, by using denaturing polyacrylamide gel electrophoresis. Oligonucleotide linkers (e.g., DNA, RNA, RNA/DNA hybrid, or having a block at the 3' end to inhibit self ligation) are attached to the 5' and 3' ends of the small RNAs. These linkers are at least 5, 10, 12, 15, 18, 20, or 25 nucleotides in length. Such linkers optionally include sites that facilitate subsequent cloning (e.g., restriction sites), sites that promote transcription (e.g., T7 site), or sites that facilitate the purification of the microRNA (e.g., a biotin).

Diagnostics

MicroRNAs or small noncoding RNAs are likely to be differentially expressed in a variety of pathologies. The methods of the invention are useful for the identification of microRNAs whose differential expression in associated with pathology. The identification of one or more microRNAs that are differentially expressed in a subject having a pathology, relative to their expression in a normal control subject, indicates that the pathology is a microRNA-related condition, disease, or disorder.

A set of two or more differentially expressed microRNAs defines a microRNA expression profile. A specific microRNA expression profile may correlate with a particular disease state. Methods of the invention may be used for the analysis of a microRNA expression profile in a biological sample derived from a subject. The identification of a microRNA profile in a biological sample from a subject may indicate that the subject has a microRNA-related condition, disease, of disorder.

In one example, microRNAs are isolated from a neoplasm, and their expression is compared to the expression of microRNAs isolated from corresponding normal control tissue. One or more microRNAs that are differentially expressed in a neoplasm defines the microRNA expression profile of the neoplasm. The identification of an altered microRNA expression profile in a neoplastic tissues is useful in the diagnosis of a microRNA-related neoplasm. Such a neoplasm is treated with a therapeutic molecule that modulates microRNA expression. The treatment regimen is monitored by assaying for an alteration in the microRNA expression profile. A therapeutic molecule that normalizes the microRNA expression profile is useful in the methods of the invention.

Mutations in microRNAs and small noncoding RNAs, which normally function in hematopoietic development, are associated with cell cycle dysfunction and leukemia in humans. Similarly, mutations in the disclosed microRNAs and small noncoding RNAs (e.g., those listed in Table 1 or 2), which normally function in development, are likely to be associated with a microRNA-related disease, such as a neoplastic disease. The differential expression of at least one of the nucleic acids listed in Table 2 in a subject diagnosed as having a particular condition, disease, or disorder, relative to a normal control patient, indicates that the pathology is a microRNA-related condition, disease, or disorder.

In one example, oligonucleotides or longer fragments derived from any of the nucleic acid sequences described herein (e.g., those listed in Table 1 or Table 2) may be used as targets in a microarray. The microarray is used to assay the expression level of large numbers of microRNAs or small noncoding RNAs simultaneously and to identify genetic variants, mutations, and polymorphisms. Such information can be used to diagnose a microRNA-related condition, disease, or disorder.

In yet another example, hybridization with PCR probes that are capable of detecting at least one of the polynucleotide sequences listed in Table 1 or 2, including microRNA precursors, or closely related molecules, may be used to hybridize to a nucleic acid sequence derived from a patient having a microRNA-related condition, disease, or disorder. The specificity of the probe and the stringency of the hybridization or amplification (maximal, high, intermediate, or low), determines whether the probe hybridizes to a naturally occurring sequence, allelic variants, or other related sequences. Hybridization techniques may be used to identify mutations indicative of a microRNA-related condition, disease, or disorder in a nucleic acid sequence listed in Table 1 or 2, or may be used to monitor expression levels of these nucleic acid molecules.

In yet another example, humans may be diagnosed for a propensity to develop a microRNA-related condition, disease, or disorder by direct analysis of the sequence of at least one of the nucleic acids listed in Table 1 or 2.

Microarrays

The nucleic acid molecules described herein (e.g., detectably labeled microRNAs that are amplified from a sample or that include a linker, or a nucleic acid molecule listed in Tables 1 or 2), or fragments thereof, are useful as hybridizable array elements in a microarray. The array elements are organized in an ordered fashion such that each element is present at a specified location on the substrate. Useful substrate materials include membranes, composed of paper, nylon or other materials, filters, chips, beads, glass slides, and other solid supports. The ordered arrangement of the array elements allows hybridization patterns and intensities to be interpreted as expression levels of particular genes or proteins.

Alternatively, an array element is identified not by its geographical location, but because it is linked to an identifiable substrate. The substrate would necessarily have a characteristic (e.g., size, color, fluorescent label, charge, or any other identifiable signal) that allows the substrate and its linked nucleic acid molecule to be distinguished from other substrates with linked nucleic acid molecules. The association of the array element with an identifiable substrate allows hybridization patterns and intensities to be interpreted as expression levels of particular genes. In one example, a nucleic acid molecule is affixed to a bead that fluoresces at a particular wave length. Binding of a detectably labeled microRNA to the oligonucleotide alters the fluorescence of the bead. Such binding can be detected using standard methods.

Methods for making nucleic acid microarrays are known to the skilled artisan and are described, for example, in U.S. Pat. No. 5,837,832, Lockhart, et al. (*Nat Biotech* 14:1675-1680, 1996), and Schena, et al. (*Proc Natl Acad Sci USA* 93:10614-10619, 1996), herein incorporated by reference. Methods for making polypeptide microarrays are described, for example, by Ge (*Nucleic Acids Res* 28:e3.i-e3.vii, 2000), MacBeath et al., (*Science* 289:1760-1763, 2000), Zhu et al. (*Nat Genet* 26:283-289), and in U.S. Pat. No. 6,436,665, hereby incorporated by reference.

Nucleic Acid Microarrays

To produce a nucleic acid microarray oligonucleotides may be synthesized or bound to the surface of a substrate using a chemical coupling procedure and an ink jet application apparatus, as described in PCT application WO95/251116 (Baldeschweiler et al.), incorporated herein by reference. Alternatively, a gridded array may be used to arrange and link cDNA fragments or oligonucleotides to the surface of a substrate using a vacuum system, thermal, UV, mechanical or chemical bonding procedure.

A nucleic acid molecule (e.g., RNA or DNA) derived from a biological sample may be used to produce a hybridization probe as described herein. The biological samples are generally derived from a patient, preferably as a bodily fluid (such as blood, cerebrospinal fluid, phlegm, saliva, or urine) or tissue sample (e.g., a tissue sample obtained by biopsy). For some applications, cultured cells (e.g., lymphocytes) or other tissue preparations may be used. The mRNA is isolated according to standard methods, and cDNA is produced and used as a template to make complementary RNA suitable for hybridization. Such methods are described herein. The RNA is amplified in the presence of fluorescent nucleotides, and the labeled probes are then incubated with the microarray to allow the probe sequence to hybridize to complementary oligonucleotides bound to the microarray. Such hybridization methods are described herein. A detection system may be used to measure the absence, presence, and amount of hybridization for all of the distinct sequences simultaneously (e.g., Heller et al., Proc Natl Acad Sci USA 94:2150-2155, 1997). Preferably, a scanner is used to determine the levels and patterns of fluorescence.

Screening Assays

The invention described herein also provides screening methods for the identification of therapeutic molecules for the treatment or prevention of a microRNA-related condition, disease, or disorder.

In addition, the microRNA sequences described herein are useful as therapeutic targets for the treatment of a microRNA-related pathology. These compositions of the invention are useful for the high-throughput, low-cost screening of candidate compounds to identify those that modulate the expression of a microRNA whose expression is altered in a patient having a microRNA-related condition, disease, or disorder. In one embodiment, the effects of known therapeutic drugs on the expression of a microRNA can be assayed using the methods of the invention. Tissues or cells treated with these drugs are compared to untreated corresponding control samples to produce expression profiles of known therapeutic agents. Knowing the identity of sequences that are differentially regulated in the presence and absence of a therapeutic agent is useful in understanding the mechanisms of drug action.

Any number of methods are available for carrying out screening assays to identify new candidate compounds that modulates the expression of a microRNA. In one working example, candidate compounds are added at varying concentrations to the culture medium of cultured cells expressing one of the nucleic acid sequences of the invention. MicroRNA expression is then measured, for example, by microRNA microarray analysis, Northern blot analysis (Ausubel et al., supra), reverse transcriptase PCR, or quantitative real-time PCR using any appropriate fragment prepared from the nucleic acid molecule as a hybridization probe. The level of gene expression in the presence of the candidate compound is compared to the level measured in a control culture medium lacking the candidate molecule. A compound that modulates the expression of a microRNA, or a functional equivalent thereof, is considered useful in the invention; such a molecule may be used, for example, as a therapeutic to treat a microRNA-related condition, disease, or disorder in a human patient.

In yet another working example, candidate compounds may be screened for those that specifically bind to a microRNA (e.g., a microRNA listed in Table 1 or 2) or a microRNA precursor. The efficacy of a candidate compound is dependent upon its ability to interact with such a microRNA or with a microRNA precursor. Such an interaction can be readily assayed using any number of standard binding techniques and functional assays (e.g., those described in Ausubel et al., supra). In one embodiment, a candidate compound may be tested in vitro for its ability to specifically bind a microRNA or a microRNA precursor of the invention. In another embodiment, a candidate compound is tested for its ability to enhance the biological activity of a microRNA or a microRNA precursor described herein. The biological activity of a microRNA or a microRNA precursor may be assayed using any standard method, for example, by assaying the expression of a genetic target of the microRNA.

In another working example, a nucleic acid described herein (e.g., a nucleic acid listed in Table 1 or 2) is expressed as a transcriptional or translational fusion with a detectable reporter, and expressed in an isolated cell (e.g., mammalian or insect cell) under the control of a promoter, such as the microRNA's own promoter or a heterologous promoter, such as an inducible promoter. The cell expressing the fusion protein is then contacted with a candidate compound, and the expression of the detectable reporter in that cell is compared to the expression of the detectable reporter in an untreated control cell. A candidate compound that alters (e.g., increases or decreases) the expression of the detectable reporter is a compound that is useful for the treatment of a microRNA-related disease or disorder.

Candidate compounds include organic molecules, peptides, peptide mimetics, polypeptides, nucleic acids, and antibodies that bind to a nucleic acid sequence of the invention (e.g., those listed in Table 1 or 2). For those nucleic acid sequences or polypeptides whose expression is decreased in a patient having a microRNA-related condition, disease, or disorder, agonists would be particularly useful in the methods of the invention. For those nucleic acid molecules or polypeptides whose expression is increased in a patient having a microRNA-related condition, disease, or disorder, antagonists would be particularly useful in the methods of the invention.

Small molecules of the invention preferably have a molecular weight below 2,000 daltons, more preferably between 300 and 1,000 daltons, and most preferably between 400 and 700 daltons. It is preferred that these small molecules are organic molecules.

Test Compounds and Extracts

In general, compounds capable of altering the expression or activity of a microRNA are identified from large libraries of both natural product or synthetic (or semi-synthetic) extracts or chemical libraries or from polypeptide or nucleic acid libraries (e.g., a library containing nucleic acid molecules listed in Table 1 or 2), according to methods known in the art. Those skilled in the field of drug discovery and development will understand that the precise source of test extracts or compounds is not critical to the screening procedure(s) of the invention. Compounds used in screens may include known compounds (for example, known therapeutics used for other diseases or disorders). Alternatively, virtually any number of unknown chemical extracts or compounds can be screened using the methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their molt-disrupting activity should be employed whenever possible.

When a crude extract is found to alter the expression or activity of a microRNA, or found to bind a microRNA, further fractionation of the positive lead extract is necessary to isolate chemical constituents responsible for the observed effect. Thus, the goal of the extraction, fractionation, and purification process is the careful characterization and identification of a chemical entity within the crude extract that alters the expression or activity of a microRNA, or that binds a microRNA. Methods of fractionation and purification of such heterogenous extracts are known in the art. If desired, compounds shown to be useful as therapeutics for the treatment of a microRNA related disorder are chemically modified according to methods known in the art.

OTHER EMBODIMENTS

From the foregoing description, it will be apparent that variations and modifications may be made to the invention described herein to adapt it to various usages and conditions. Such embodiments are also within the scope of the following claims.

All publications mentioned in this specification are herein incorporated by reference to the same extent as if each independent publication was specifically and individually indicated to be incorporated by reference.

What is claimed is:

1. A method for identifying microRNA expression in a sample, said method comprising:
   (a) providing RNA from said sample, wherein said RNA comprises a microRNA;
   (b) appending at least two linkers to said microRNA;
   (c) detectably labeling said microRNA of step (b);
   (d) contacting a microarray comprising at least 2 oligonucleotides with said detectably labeled microRNA; and
   (e) detecting binding of said detectably labeled microRNA to said microarray.

2. The method of claim 1, wherein said RNA is isolated microRNA.

3. The method of claim 1, wherein said linker comprises an oligonucleotide.

4. The method of claim 3, wherein said linker is an RNA/DNA hybrid.

5. The method of claim 1, wherein said linker is appended in a ligation reaction.

6. The method of claim 1, wherein said microRNA is useful as a template for a reverse transcriptase polymerase chain reaction (RT-PCR).

7. The method of claim 1, wherein said microRNA is detectably labeled during the performance of the polymerase chain reaction (PCR).

8. The method of claim 1, wherein at least one of said linkers comprises at least one restriction site.

9. The method of claim 1, wherein said sample is a tissue sample.

10. A method for identifying microRNA expression, said method comprising:
    (a) providing a microRNA isolated from a sample;
    (b) amplifying said microRNA to produce a detectably labeled microRNA;
    (c) contacting a microarray comprising at least 2 oligonucleotides with said detectably labeled microRNA; and
    (d) detecting binding of said detectably labeled microRNA to said microarray.

11. The method of claim 10, wherein said microRNA is detectably labeled during the performance of PCR.

12. The method of claim 10, wherein said detectable label is a fluorophore.

13. The method of claim 10, wherein said detectable label is detected by analyzing enzyme activity, by direct immunoassay, or by a radiometric assay.

14. The method of claim 10, wherein said sample is a tissue sample.

15. The method of claim 1 or 10, wherein said sample is a neoplastic tissue sample.

16. The method of claim 1 or 10, wherein said microarray comprises at least 10 oligonucleotides.

17. The method of claim 16, wherein said microarray comprises at least 25 oligonucleotides.

18. The method of claim 17, wherein said microarray comprises at least 50 oligonucleotides.

19. The method of claim 18, wherein said microarray comprises at least 100 oligonucleotides.

20. A method for identifying microRNA expression in a sample, said method comprising:
    (a) providing RNA from said sample, wherein said RNA comprises a microRNA;
    (b) appending at least one linker to said microRNA, wherein said linker comprises a T7 promoter;
    (c) detectably labeling said microRNA of step (b);
    (d) contacting a microarray comprising at least 2 oligonucleotides with said detectably labeled microRNA; and
    (e) detecting binding of said detectably labeled microRNA to said microarray.

21. A method for identifying differential expression of a microRNA in a test sample, said method comprising:
    (a) providing a microRNA isolated from a test sample;
    (b) amplifying said microRNA to produce a detectably labeled microRNA;
    (c) contacting a microarray comprising at least 2 oligonucleotides with said detectably labeled microRNA; and
    (d) detecting differential binding of said detectably labeled microRNA to said microarray, relative to the binding of a corresponding detectably labeled microRNA isolated from a control.

22. The method of claim 21, wherein said test sample is a tissue sample from a subject having a disease, condition, or disorder selected from the group consisting of autoinflammatory disorders, proliferative diseases, cardiovascular diseases, obesity, or an obesity related diseases.

23. The method of claim 22, wherein said proliferative disorder is selected from the group consisting of leukemias, lymphomas, sarcomas and carcinomas.

24. The method of claim 22, wherein said autoinflammatory disorder is selected from the group consisting of asthma, allergic intraocular inflammatory diseases, arthritis, atopic dermatitis, atopic eczema, diabetes, haemolytic anaemia, inflammatory dermatoses, inflammatory bowel or gastrointestinal disorders, multiple sclerosis, myasthenia gravis, pruritis/inflammation, psoriasis, rheumatoid arthritis, and systemic lupus erythematosus.

25. The method of claim 22, wherein said cardiovascular disease is atherosclerosis, hypertension, cardiac artery disease, myocardial infarction, or congestive heart failure.

26. The method of claim 22, wherein said obesity-related disease is diabetes.

27. A method for producing a microRNA microarray, said method comprising:
(a) providing a microRNA;
(b) amplifying said microRNA; and
(c) affixing said microRNA to a solid support.

28. A method for identifying microRNA expression in a cell, said method comprising:
(a) amplifying a microRNA from a sample;
(b) detectably labeling said microRNA;
(c) contacting a microarray with said labeled microRNA; and
(d) measuring binding of said labeled microRNA to said microarray, wherein binding identifies said microRNA as being a microRNA expressed in said cell.

29. The method of claim 28, wherein said detectable label is a fluorophore.

30. The method of claim 29, wherein said binding alters the fluorescence of said fluorophore.

31. A method for identifying microRNA expression in a sample, said method comprising:
(a) providing RNA from said sample, wherein said RNA comprises a microRNA;
(b) appending at least one linker to said microRNA;
(c) detectably labeling said microRNA of step (b) during the performance of PCR;
(d) contacting a microarray comprising at least 2 oligonucleotides with said detectably labeled microRNA; and
(e) detecting binding of said detectably labeled microRNA to said microarray.

32. A method of labeling a microRNA, said method comprising:
(a) appending at least one linker to said microRNA;
(b) detectably labeling said microRNA of step (b) during the performance of PCR; thereby labeling said microRNA.

33. The method of claim 32, wherein said linker is an RNA/DNA hybrid.

34. The method of claim 32, wherein reverse transcription of said microRNA is performed prior to step (b).

35. The method of claim 32, wherein step (b) includes appending at least two linkers to said microRNA.

36. A method for identifying microRNA expression, said method comprising:
(a) attaching to a microRNA a linker bound to a detectable label;
(b) contacting a microarray comprising at least 2 oligonucleotides with said detectably labeled microRNA; and
(c) detecting binding of said detectably labeled microRNA to said microarray.

37. The method of claim 36, wherein said microRNA is isolated microRNA.

38. The method of claim 36, wherein said linker comprises an oligonucleotide.

39. The method of claim 36, wherein said detectable label is a fluorophore.

40. The method of claim 36, wherein said detectable label is detected by analyzing enzyme activity, by direct inimunoassay, or by a radiometric assay.

41. The method of claim 36, wherein said microRNA is from a tissue sample.

42. The method of claim 36, wherein said microarray comprises at least 10 oligonucleotides.

43. The method of claim 42, wherein said microarray comprises at least 50 oligonucleotides.

44. A method for identifying microRNA expression in a sample, said method comprising:
(a) providing RNA from said sample, wherein said RNA comprises a microRNA;
(b) appending at least one linker to a microRNA;
(c) detectably labeling said microRNA of step (b);
(d) contacting a microarray comprising at least 2 oligonucleotides with said detectably labeled microRNA; and
(e) detecting binding of said detectably labeled microRNA to said microarray.

45. The method of claim 44, wherein said RNA is isolated microRNA.

46. The method of claim 44, wherein said linker comprises an oligonucleotide.

47. The method of claim 46, wherein said linker is an RNA/DNA hybrid.

48. The method of claim 44, wherein said linker is appended in a ligation reaction.

49. The method of claim 44, wherein said sample is a tissue sample.

50. The method of claim 44, wherein said microarray comprises at least 10 oligonucleotides.

51. The method of claim 50, wherein said microarray comprises at least 50 oligonucleotides.

* * * * *

UNITED STATES PATENT AND TRADEMARK OFFICE
CERTIFICATE OF CORRECTION

PATENT NO. : 7,635,563 B2  Page 1 of 1
APPLICATION NO. : 11/171175
DATED : December 22, 2009
INVENTOR(S) : Horvitz et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 478 days.

Signed and Sealed this

Ninth Day of November, 2010

David J. Kappos
*Director of the United States Patent and Trademark Office*